United States Patent
Miller et al.

(10) Patent No.: US 10,973,545 B2
(45) Date of Patent: Apr. 13, 2021

(54) POWERED DRIVERS, INTRAOSSEOUS DEVICES AND METHODS TO ACCESS BONE MARROW

(71) Applicant: TELEFLEX LIFE SCIENCES LIMITED, Valletta (MT)

(72) Inventors: Larry J. Miller, Spring Branch, TX (US); David S. Bolleter, San Antonio, TX (US); Robert W. Titkemeyer, San Antonio, TX (US); Charles M. Schwimmer, Los Gatos, CA (US)

(73) Assignee: TELEFLEX LIFE SCIENCES LIMITED, Valletta (MT)

( * ) Notice: Subject to any disclaimer, the term of this patent is extended or adjusted under 35 U.S.C. 154(b) by 0 days.

(21) Appl. No.: 17/029,326

(22) Filed: Sep. 23, 2020

(65) Prior Publication Data
US 2021/0045753 A1    Feb. 18, 2021

Related U.S. Application Data

(60) Continuation-in-part of application No. 16/725,939, filed on Dec. 23, 2019, which is a continuation of
(Continued)

(51) Int. Cl.
*A61B 17/34* (2006.01)
*A61B 17/16* (2006.01)
(Continued)

(52) U.S. Cl.
CPC ........ *A61B 17/3472* (2013.01); *A61B 10/025* (2013.01); *A61B 17/1624* (2013.01);
(Continued)

(58) Field of Classification Search
CPC .............. A61B 17/1628; A61B 10/025; A61B 17/3474; A61B 17/3472
See application file for complete search history.

(56) References Cited

U.S. PATENT DOCUMENTS

| 1,539,637 A | 5/1925 | Bronner |
| 2,219,605 A * | 10/1940 | Turkel .................. A61B 10/025 |
| | | 600/566 |

(Continued)

FOREIGN PATENT DOCUMENTS

| CA | 2138842 A1 | 6/1996 |
| CA | 2366676 A1 | 9/2000 |

(Continued)

OTHER PUBLICATIONS

International Preliminary Report on Patentability, PCT/US2007/072217, 11 pages, dated Feb. 12, 2009.
(Continued)

*Primary Examiner* — Christian A Sevilla
(74) *Attorney, Agent, or Firm* — BakerHostetler

(57) ABSTRACT

An apparatus for penetrating bone and accessing bone marrow is provided. The apparatus may include a penetrator assembly and a powered drill. The penetrator assembly may include a trocar having a stylet. The penetrator assembly may also include an outer penetrator having a hollow cannula and a luer lock attachment. The powered drill may include a housing enclosing a motor and a power supply and associated circuitry. The powered drill may also include a connector receptacle for receiving a penetrator assembly connector of the penetrator assembly. The connector receptacle may releasably lock the penetrator assembly connector into place with the powered drill. The power supply may include a rechargeable battery within the housing for supplying power to the motor. A battery indicator may be provided to indicate a level of the battery.

17 Claims, 28 Drawing Sheets

Related U.S. Application Data application No. 15/272,647, filed on Sep. 22, 2016, now Pat. No. 10,512,474, which is a continuation of application No. 12/061,944, filed on Apr. 3, 2008, now Pat. No. 9,451,968, and a continuation-in-part of application No. 11/253,959, filed on Oct. 19, 2005, now Pat. No. 8,506,568, and a continuation-in-part of application No. 11/253,467, filed on Oct. 19, 2005, now Pat. No. 8,876,826, and a continuation-in-part of application No. 10/449,476, filed on May 30, 2003, now Pat. No. 7,699,850, application No. 17/029,326, filed on Sep. 23, 2020, which is a continuation-in-part of application No. 15/854,406, filed on Dec. 26, 2017, now Pat. No. 10,806,491, which is a division of application No. 14/791,654, filed on Jul. 6, 2015, now Pat. No. 9,872,703, which is a continuation of application No. 11/380,340, filed on Apr. 26, 2006, now Pat. No. 9,072,543, which is a continuation-in-part of application No. 10/449,503, filed on May 30, 2003, now Pat. No. 7,670,328.

(60) Provisional application No. 60/910,122, filed on Apr. 4, 2007, provisional application No. 60/384,756, filed on May 31, 2002, provisional application No. 60/675,246, filed on Apr. 27, 2005, provisional application No. 60/384,756, filed on May 31, 2002.

(51) Int. Cl.
| | | |
|---|---|---|
| *A61B 17/32* | (2006.01) | |
| *A61M 5/158* | (2006.01) | |
| *A61B 90/30* | (2016.01) | |
| *A61B 10/02* | (2006.01) | |
| *A61B 17/3205* | (2006.01) | |
| *A61B 17/00* | (2006.01) | |
| *A61B 90/11* | (2016.01) | |
| *A61B 90/00* | (2016.01) | |

(52) U.S. Cl.
CPC .... *A61B 17/1628* (2013.01); *A61B 17/32002* (2013.01); *A61B 17/3474* (2013.01); *A61B 17/3476* (2013.01); *A61B 90/30* (2016.02); *A61M 5/158* (2013.01); *A61B 17/1637* (2013.01); *A61B 17/32053* (2013.01); *A61B 90/11* (2016.02); *A61B 2010/0258* (2013.01); *A61B 2017/0046* (2013.01); *A61B 2017/00398* (2013.01); *A61B 2017/00734* (2013.01); *A61B 2090/0813* (2016.02); *A61M 2005/1581* (2013.01); *A61M 2005/1585* (2013.01); *A61M 2205/587* (2013.01); *A61M 2210/02* (2013.01)

(56) References Cited

U.S. PATENT DOCUMENTS

| | | | |
|---|---|---|---|
| 2,317,648 A | | 4/1943 | Siqveland |
| 2,419,045 A | | 4/1947 | Whittaker |
| 2,426,535 A | * | 8/1947 | Turkel ............. A61B 10/025 600/567 |
| 2,525,588 A | * | 10/1950 | Cameron .......... B23Q 17/2404 362/119 |
| 2,773,501 A | | 12/1956 | Young |
| 2,817,648 A | | 12/1957 | Gould |
| 2,860,635 A | | 11/1958 | Wilburn |
| 3,022,596 A | | 2/1962 | Cannon |
| 3,104,448 A | | 9/1963 | Morrow |
| 3,120,845 A | | 2/1964 | Horner |
| 3,173,417 A | | 3/1965 | Horner |
| 3,175,554 A | | 3/1965 | Stewart |
| 3,507,276 A | | 4/1970 | Burgess |
| 3,529,580 A | | 9/1970 | Stevens |
| 3,543,966 A | | 12/1970 | Ryan |
| 3,697,223 A | | 10/1972 | Kovalcik |
| 3,734,207 A | | 5/1973 | Fishbein |
| 3,750,667 A | | 8/1973 | Pshenichny et al. |
| 3,802,555 A | | 4/1974 | Grasty et al. |
| 3,815,605 A | | 6/1974 | Schmidt et al. |
| 3,835,860 A | | 9/1974 | Garretson |
| 3,893,445 A | * | 7/1975 | Hofsess ............. A61B 10/025 600/567 |
| 3,893,455 A | | 7/1975 | McNally |
| 3,935,909 A | | 2/1976 | Mabuchi et al. |
| 3,981,398 A | | 9/1976 | Boshoff |
| 3,991,765 A | | 11/1976 | Cohen |
| 3,999,110 A | | 12/1976 | Ramstrom et al. |
| 4,021,920 A | | 5/1977 | Kirschner et al. |
| 4,046,254 A | | 9/1977 | Kramer |
| 4,099,518 A | | 7/1978 | Baylis et al. |
| 4,124,026 A | | 11/1978 | Berner et al. |
| 4,142,517 A | | 3/1979 | Contreras Guerrero de Stavropoulos et al. |
| 4,170,993 A | | 10/1979 | Alvarez |
| 4,185,619 A | | 1/1980 | Reiss |
| 4,194,505 A | | 3/1980 | Schmitz |
| 4,258,722 A | | 3/1981 | Sessions et al. |
| 4,262,676 A | | 4/1981 | Jamshidi |
| 4,266,555 A | | 5/1981 | Jamshidi |
| 4,306,570 A | | 12/1981 | Matthews |
| 4,333,459 A | | 6/1982 | Becker |
| 4,359,052 A | | 11/1982 | Staub |
| 4,381,777 A | | 5/1983 | Garnier |
| 4,399,723 A | | 8/1983 | Marleau |
| 4,420,085 A | | 12/1983 | Wilson et al. |
| 4,441,563 A | | 4/1984 | Walton, II |
| 4,469,109 A | | 9/1984 | Mehl |
| 4,484,577 A | | 11/1984 | Sackner et al. |
| 4,487,209 A | | 12/1984 | Mehl |
| 4,543,966 A | | 10/1985 | Islam et al. |
| 4,553,539 A | | 11/1985 | Morris |
| 4,578,064 A | | 3/1986 | Sarnoff et al. |
| 4,605,011 A | | 8/1986 | Naslund |
| 4,620,539 A | | 11/1986 | Andrews et al. |
| 4,630,616 A | | 12/1986 | Tretinyak |
| 4,646,731 A | | 3/1987 | Brower |
| 4,654,492 A | | 3/1987 | Koerner et al. |
| 4,655,226 A | | 4/1987 | Lee |
| 4,659,329 A | | 4/1987 | Annis |
| 4,692,073 A | | 9/1987 | Martindell |
| 4,702,261 A | | 10/1987 | Cornell et al. |
| 4,711,636 A | | 12/1987 | Bierman |
| 4,713,061 A | | 12/1987 | Tarello et al. |
| 4,716,901 A | | 1/1988 | Jackson et al. |
| 4,720,881 A | | 1/1988 | Meyers |
| 4,723,945 A | | 2/1988 | Theiling |
| 4,736,850 A | | 4/1988 | Bowman et al. |
| 4,758,225 A | | 7/1988 | Cox et al. |
| 4,762,118 A | | 8/1988 | Lia et al. |
| 4,772,261 A | | 9/1988 | Von Hoff et al. |
| 4,787,893 A | | 11/1988 | Villette |
| 4,793,363 A | | 12/1988 | Ausherman et al. |
| 4,810,248 A | | 3/1989 | Masters et al. |
| 4,838,282 A | | 6/1989 | Strasser et al. |
| 4,844,259 A | | 7/1989 | Glowczewskie, Jr. et al. |
| 4,867,158 A | | 9/1989 | Sugg |
| 4,919,146 A | | 4/1990 | Rhinehart et al. |
| 4,921,013 A | | 5/1990 | Spalink et al. |
| 4,922,602 A | | 5/1990 | Mehl |
| 4,935,010 A | | 6/1990 | Cox et al. |
| 4,940,459 A | | 7/1990 | Noce |
| 4,944,677 A | | 7/1990 | Alexandre |
| 4,969,870 A | | 11/1990 | Kramer et al. |
| 4,986,279 A | | 1/1991 | ONeill |
| 5,002,546 A | | 3/1991 | Romano |
| 5,025,797 A | | 6/1991 | Baran |
| 5,036,860 A | | 8/1991 | Leigh et al. |
| 5,057,085 A | | 10/1991 | Kopans |
| 5,064,426 A | | 11/1991 | Huebsch |
| 5,074,311 A | | 12/1991 | Hasson |
| 5,116,324 A | | 5/1992 | Brierley et al. |

(56) References Cited

U.S. PATENT DOCUMENTS

| | | | |
|---|---|---|---|
| 5,120,312 | A | 6/1992 | Wigness et al. |
| 5,122,114 | A | 6/1992 | Miller et al. |
| 5,133,359 | A | 7/1992 | Kedem |
| 5,137,518 | A | 8/1992 | Mersch |
| 5,139,500 | A | 8/1992 | Schwartz |
| RE34,056 | E | 9/1992 | Lindgren et al. |
| 5,145,369 | A | 9/1992 | Lustig et al. |
| 5,172,701 | A | 12/1992 | Leigh |
| 5,172,702 | A | 12/1992 | Leigh et al. |
| 5,176,415 | A | 1/1993 | Choksi |
| 5,176,643 | A | 1/1993 | Kramer et al. |
| 5,187,422 | A | 2/1993 | Izenbaard et al. |
| 5,195,985 | A | 3/1993 | Hall |
| 5,203,056 | A | 4/1993 | Funk et al. |
| 5,207,303 | A | 5/1993 | Oswalt et al. |
| 5,207,697 | A * | 5/1993 | Carusillo .......... A61B 17/1626 320/115 |
| 5,217,478 | A | 6/1993 | Rexroth |
| 5,244,619 | A | 9/1993 | Burnham |
| 5,249,583 | A | 10/1993 | Mallaby |
| 5,257,632 | A | 11/1993 | Turkel et al. |
| 5,261,877 | A | 11/1993 | Fine et al. |
| 5,269,785 | A | 12/1993 | Bonutti |
| 5,271,414 | A | 12/1993 | Partika et al. |
| 5,279,306 | A | 1/1994 | Mehl |
| 5,300,070 | A | 4/1994 | Gentelia et al. |
| 5,312,351 | A | 5/1994 | Gerrone |
| 5,312,364 | A | 5/1994 | Jacobs |
| 5,312,408 | A | 5/1994 | Brown |
| 5,315,737 | A | 5/1994 | Ouimet |
| 5,324,300 | A | 6/1994 | Elias et al. |
| 5,332,398 | A | 7/1994 | Miller et al. |
| 5,333,790 | A | 8/1994 | Christopher |
| 5,334,169 | A | 8/1994 | Brown et al. |
| 5,339,831 | A | 8/1994 | Thompson |
| 5,341,816 | A | 8/1994 | Allen |
| 5,341,823 | A | 8/1994 | Manosalva et al. |
| 5,348,022 | A | 9/1994 | Leigh et al. |
| 5,356,006 | A | 10/1994 | Alpern et al. |
| 5,357,974 | A | 10/1994 | Baldridge |
| 5,361,853 | A | 11/1994 | Takamura et al. |
| 5,368,046 | A | 11/1994 | Scarfone et al. |
| 5,372,583 | A | 12/1994 | Roberts et al. |
| 5,383,859 | A | 1/1995 | Sewell, Jr. |
| 5,385,151 | A | 1/1995 | Scarfone et al. |
| 5,385,553 | A | 1/1995 | Hart et al. |
| 5,389,553 | A | 2/1995 | Grubisich et al. |
| 5,400,798 | A | 3/1995 | Baran |
| 5,405,348 | A | 4/1995 | Anspach, Jr. et al. |
| 5,405,362 | A | 4/1995 | Kramer et al. |
| 5,423,824 | A | 6/1995 | Akerfeldt et al. |
| 5,431,655 | A | 7/1995 | Melker et al. |
| 5,451,210 | A | 9/1995 | Kramer et al. |
| 5,484,442 | A | 1/1996 | Melker et al. |
| 5,497,787 | A | 3/1996 | Nemesdy et al. |
| D369,858 | S | 5/1996 | Baker et al. |
| 5,514,097 | A | 5/1996 | Knauer |
| 5,526,821 | A | 6/1996 | Jamshidi |
| 5,529,580 | A | 6/1996 | Kusunoki et al. |
| 5,549,565 | A | 8/1996 | Ryan et al. |
| 5,554,154 | A | 9/1996 | Rosenberg |
| 5,556,399 | A | 9/1996 | Huebner |
| 5,558,737 | A | 9/1996 | Brown et al. |
| 5,571,133 | A | 11/1996 | Yoon |
| 5,586,847 | A | 12/1996 | Mattern, Jr. et al. |
| 5,591,188 | A | 1/1997 | Waisman |
| 5,595,186 | A | 1/1997 | Rubinstein et al. |
| 5,601,559 | A | 2/1997 | Melker et al. |
| 5,632,747 | A | 5/1997 | Scarborough et al. |
| 5,651,419 | A | 7/1997 | Holzer et al. |
| 5,672,155 | A | 9/1997 | Riley et al. |
| 5,713,368 | A | 2/1998 | Leigh |
| 5,724,873 | A | 3/1998 | Hillinger |
| 5,733,262 | A | 3/1998 | Paul |
| 5,752,923 | A | 5/1998 | Terwilliger |
| 5,762,639 | A | 6/1998 | Gibbs |
| 5,766,221 | A | 6/1998 | Benderev et al. |
| 5,769,086 | A | 6/1998 | Ritchart et al. |
| 5,779,708 | A | 7/1998 | Wu |
| 5,800,389 | A | 9/1998 | Burney et al. |
| 5,801,454 | A | 9/1998 | Leininger |
| 5,807,275 | A | 9/1998 | Jamshidi |
| 5,807,277 | A | 9/1998 | Swaim |
| 5,809,653 | A | 9/1998 | Everts et al. |
| 5,810,826 | A | 9/1998 | Åkerfeldt et al. |
| 5,817,052 | A | 10/1998 | Johnson et al. |
| 5,823,970 | A | 10/1998 | Terwilliger |
| D403,405 | S | 12/1998 | Terwilliger |
| 5,858,005 | A | 1/1999 | Kriesel |
| 5,865,711 | A | 2/1999 | Chen |
| 5,868,711 | A | 2/1999 | Kramer et al. |
| 5,868,750 | A | 2/1999 | Schultz |
| 5,873,499 | A | 2/1999 | Leschinsky et al. |
| 5,873,510 | A | 2/1999 | Hirai et al. |
| 5,885,226 | A | 3/1999 | Rubinstein et al. |
| 5,891,085 | A | 4/1999 | Lilley et al. |
| 5,906,797 | A | 5/1999 | Orihara et al. |
| 5,911,701 | A | 6/1999 | Miller et al. |
| 5,911,708 | A | 6/1999 | Teirstein |
| 5,916,229 | A | 6/1999 | Evans |
| 5,919,172 | A | 7/1999 | Golba, Jr. |
| 5,921,987 | A | 7/1999 | Stone |
| 5,924,864 | A | 7/1999 | Loge et al. |
| 5,926,989 | A | 7/1999 | Oliver, Sr. |
| 5,927,976 | A | 7/1999 | Wu |
| 5,928,238 | A | 7/1999 | Scarborough et al. |
| 5,928,241 | A | 7/1999 | Menut et al. |
| 5,938,636 | A | 8/1999 | Kramer et al. |
| 5,941,706 | A | 8/1999 | Ura |
| 5,941,851 | A | 8/1999 | Coffey et al. |
| 5,951,026 | A | 9/1999 | Harman, Jr. et al. |
| 5,960,797 | A | 10/1999 | Kramer et al. |
| 5,980,545 | A | 11/1999 | Pacala et al. |
| 5,984,020 | A | 11/1999 | Meyer et al. |
| 5,993,417 | A | 11/1999 | Yerfino et al. |
| 5,993,454 | A | 11/1999 | Longo |
| 6,007,496 | A | 12/1999 | Brannon |
| 6,017,348 | A | 1/2000 | Hart et al. |
| 6,018,094 | A | 1/2000 | Fox |
| 6,018,230 | A | 1/2000 | Casey |
| 6,022,324 | A | 2/2000 | Skinner |
| 6,025,683 | A | 2/2000 | Philipp |
| 6,027,458 | A | 2/2000 | Janssens |
| 6,033,369 | A | 3/2000 | Goldenberg |
| 6,033,408 | A * | 3/2000 | Gage ................. A61B 17/162 173/218 |
| 6,033,411 | A | 3/2000 | Preissman |
| 6,042,585 | A | 3/2000 | Norman |
| 6,049,725 | A | 4/2000 | Emmert et al. |
| 6,059,806 | A * | 5/2000 | Hoegerle .......... A61B 17/1628 606/180 |
| 6,063,037 | A | 5/2000 | Mittermeier et al. |
| 6,066,938 | A | 5/2000 | Hyodo et al. |
| 6,071,284 | A | 6/2000 | Fox |
| 6,080,115 | A | 6/2000 | Rubinstein |
| 6,083,176 | A | 7/2000 | Terwilliger |
| 6,086,543 | A | 7/2000 | Anderson et al. |
| 6,086,544 | A | 7/2000 | Hibner et al. |
| 6,092,355 | A | 7/2000 | Ishmael |
| 6,096,042 | A | 8/2000 | Herbert |
| 6,102,915 | A | 8/2000 | Bresler et al. |
| 6,106,484 | A | 8/2000 | Terwilliger |
| 6,110,128 | A | 8/2000 | Andelin et al. |
| 6,110,129 | A | 8/2000 | Terwilliger |
| 6,110,174 | A | 8/2000 | Nichter |
| 6,120,462 | A | 9/2000 | Hibner et al. |
| 6,126,670 | A | 10/2000 | Walker et al. |
| 6,135,769 | A | 10/2000 | Kwan |
| 6,152,918 | A | 11/2000 | Padilla et al. |
| 6,159,163 | A | 12/2000 | Strauss et al. |
| 6,162,203 | A | 12/2000 | Haaga |
| 6,183,442 | B1 | 2/2001 | Athanasiou et al. |
| 6,187,768 | B1 | 2/2001 | Welle et al. |
| 6,210,376 | B1 | 4/2001 | Grayson |

(56) References Cited

U.S. PATENT DOCUMENTS

| | | |
|---|---|---|
| 6,217,561 B1 | 4/2001 | Gibbs |
| 6,221,029 B1 | 4/2001 | Mathis et al. |
| 6,228,049 B1 | 5/2001 | Schroeder et al. |
| 6,228,088 B1 | 5/2001 | Miller et al. |
| 6,238,355 B1 | 5/2001 | Daum |
| 6,247,928 B1 | 6/2001 | Meller et al. |
| 6,248,110 B1 | 6/2001 | Reiley et al. |
| 6,257,351 B1 | 7/2001 | Ark et al. |
| 6,267,763 B1 | 7/2001 | Castro |
| 6,273,715 B1 | 8/2001 | Meller et al. |
| 6,273,862 B1 | 8/2001 | Privitera et al. |
| 6,283,925 B1 | 9/2001 | Terwilliger |
| 6,283,970 B1 | 9/2001 | Lubinus |
| 6,287,114 B1 | 9/2001 | Meller et al. |
| 6,302,852 B1 | 10/2001 | Fleming, III et al. |
| 6,309,358 B1 | 10/2001 | Okubo |
| 6,312,394 B1 | 11/2001 | Fleming, III |
| 6,315,737 B1 | 11/2001 | Skinner |
| 6,325,806 B1 | 12/2001 | Fox |
| 6,328,701 B1 | 12/2001 | Terwilliger |
| 6,328,744 B1 | 12/2001 | Harari et al. |
| 6,358,252 B1 | 3/2002 | Shapira |
| 6,382,212 B1 | 5/2002 | Borchard |
| 6,402,701 B1 | 6/2002 | Kaplan et al. |
| 6,419,490 B1 | 7/2002 | Kitchings Weathers, Jr. |
| 6,425,888 B1 | 7/2002 | Embleton et al. |
| 6,428,487 B1 | 8/2002 | Burdorff et al. |
| 6,443,910 B1 | 9/2002 | Krueger et al. |
| 6,458,117 B1 | 10/2002 | Pollins, Sr. |
| 6,468,248 B1 | 10/2002 | Gibbs |
| 6,478,751 B1 | 11/2002 | Krueger et al. |
| 6,488,636 B2 | 12/2002 | Bryan et al. |
| 6,494,590 B1 | 12/2002 | Paganini et al. |
| 6,523,698 B1 | 2/2003 | Dennehey et al. |
| 6,527,736 B1 | 3/2003 | Attinger et al. |
| 6,527,778 B2 | 3/2003 | Athanasiou et al. |
| 6,540,694 B1 | 4/2003 | Van Bladel et al. |
| 6,547,511 B1 | 4/2003 | Adams |
| 6,547,561 B2 | 4/2003 | Meller et al. |
| 6,550,786 B2 | 4/2003 | Gifford et al. |
| 6,554,779 B2 | 4/2003 | Viola et al. |
| 6,555,212 B2 | 4/2003 | Boiocchi et al. |
| 6,572,563 B2 | 6/2003 | Ouchi |
| 6,575,919 B1 | 6/2003 | Reiley et al. |
| 6,582,399 B1 | 6/2003 | Smith et al. |
| 6,585,622 B1 | 7/2003 | Shum et al. |
| 6,595,362 B2 | 7/2003 | Penney et al. |
| 6,595,911 B2 | 7/2003 | LoVuolo |
| 6,595,979 B1 | 7/2003 | Epstein et al. |
| 6,613,054 B2 | 9/2003 | Scribner et al. |
| 6,616,632 B2 | 9/2003 | Sharp et al. |
| 6,620,111 B2 | 9/2003 | Stephens et al. |
| 6,626,173 B2 | 9/2003 | Genova et al. |
| 6,626,848 B2 | 9/2003 | Neuenfeldt |
| 6,626,887 B1 | 9/2003 | Wu |
| 6,638,235 B2 | 10/2003 | Miller et al. |
| 6,656,133 B2 | 12/2003 | Voegele et al. |
| 6,689,072 B2 | 2/2004 | Kaplan et al. |
| 6,690,308 B2 | 2/2004 | Hayami |
| 6,702,760 B2 | 3/2004 | Krause et al. |
| 6,702,761 B1 | 3/2004 | Damadian et al. |
| 6,706,016 B2 | 3/2004 | Cory et al. |
| 6,716,192 B1 | 4/2004 | Orosz, Jr. |
| 6,716,215 B1 | 4/2004 | David et al. |
| 6,716,216 B1 | 4/2004 | Boucher et al. |
| 6,730,043 B2 | 5/2004 | Krueger et al. |
| 6,730,044 B2 | 5/2004 | Stephens et al. |
| 6,749,576 B2 | 6/2004 | Bauer |
| 6,752,768 B2 | 6/2004 | Burdorff et al. |
| 6,752,816 B2 | 6/2004 | Culp et al. |
| 6,758,824 B1 | 7/2004 | Miller et al. |
| 6,761,726 B1 | 7/2004 | Findlay et al. |
| 6,796,957 B2 | 9/2004 | Carpenter et al. |
| 6,846,314 B2 | 1/2005 | Shapira |
| 6,849,051 B2 | 2/2005 | Sramek et al. |
| 6,855,148 B2 | 2/2005 | Foley et al. |
| 6,860,860 B2 | 3/2005 | Viola |
| 6,875,183 B2 | 4/2005 | Cervi |
| 6,875,219 B2 | 4/2005 | Arramon et al. |
| 6,884,245 B2 | 4/2005 | Spranza, III |
| 6,887,209 B2 | 5/2005 | Kadziauskas et al. |
| 6,890,308 B2 | 5/2005 | Islam |
| 6,896,141 B2 | 5/2005 | McMichael et al. |
| 6,905,486 B2 | 6/2005 | Gibbs |
| 6,930,461 B2 | 8/2005 | Rutkowski |
| 6,942,669 B2 | 9/2005 | Kurc |
| 6,969,373 B2 | 11/2005 | Schwartz et al. |
| 7,001,342 B2 | 2/2006 | Faciszewski |
| 7,008,381 B2 | 3/2006 | Janssens |
| 7,008,383 B1 | 3/2006 | Damadian et al. |
| 7,008,394 B2 | 3/2006 | Geise et al. |
| 7,018,343 B2 | 3/2006 | Plishka |
| 7,025,732 B2 | 4/2006 | Thompson et al. |
| 7,063,672 B2 | 6/2006 | Schramm |
| 7,063,703 B2 | 6/2006 | Reo |
| 7,137,985 B2 | 11/2006 | Jahng |
| 7,186,257 B2 | 3/2007 | Kim |
| 7,207,949 B2 | 4/2007 | Miles et al. |
| 7,226,450 B2 | 6/2007 | Athanasiou et al. |
| 7,229,401 B2 | 6/2007 | Kindlein |
| 7,278,972 B2 | 10/2007 | Lamoureux et al. |
| 7,331,462 B2 | 2/2008 | Steppe |
| 7,331,930 B2 | 2/2008 | Faciszewski |
| 7,513,722 B2 | 4/2009 | Greenberg et al. |
| 7,565,935 B1 | 7/2009 | Phillips |
| 7,615,043 B2 | 11/2009 | Zhou |
| 7,670,328 B2 | 3/2010 | Miller |
| 7,699,850 B2 | 4/2010 | Miller |
| 7,811,260 B2 | 10/2010 | Miller et al. |
| 7,815,642 B2 | 10/2010 | Miller |
| 7,850,620 B2 | 12/2010 | Miller et al. |
| 7,951,089 B2 | 5/2011 | Miller |
| 7,988,643 B2 | 8/2011 | Hoffmann et al. |
| 8,038,664 B2 | 10/2011 | Miller et al. |
| 8,142,365 B2 | 3/2012 | Miller |
| 8,217,561 B2 | 7/2012 | Fukuzawa et al. |
| 8,308,693 B2 | 11/2012 | Miller et al. |
| 8,419,683 B2 | 4/2013 | Miller et al. |
| 8,480,632 B2 | 7/2013 | Miller et al. |
| 8,506,568 B2 | 8/2013 | Miller |
| 8,641,715 B2 | 2/2014 | Miller |
| 8,656,929 B2 | 2/2014 | Miller et al. |
| 8,668,698 B2 | 3/2014 | Miller et al. |
| 8,684,978 B2 | 4/2014 | Miller et al. |
| 8,690,791 B2 | 4/2014 | Miller |
| 8,715,287 B2 | 5/2014 | Miller |
| 8,870,872 B2 | 10/2014 | Miller |
| 8,876,826 B2 | 11/2014 | Miller |
| 8,944,069 B2 | 2/2015 | Miller et al. |
| 8,974,410 B2 | 3/2015 | Miller et al. |
| 8,998,848 B2 | 4/2015 | Miller et al. |
| 9,072,543 B2 | 7/2015 | Miller et al. |
| 9,078,637 B2 | 7/2015 | Miller |
| 9,439,667 B2 | 9/2016 | Miller |
| 9,451,968 B2 | 9/2016 | Miller et al. |
| 9,504,477 B2 | 11/2016 | Miller et al. |
| 9,662,160 B2 | 5/2017 | Beale et al. |
| 9,826,984 B2 | 11/2017 | McGinley et al. |
| 9,872,703 B2 | 1/2018 | Miller et al. |
| 10,052,111 B2 | 8/2018 | Miller et al. |
| 10,245,010 B2 | 4/2019 | Miller et al. |
| 10,258,783 B2 | 4/2019 | Miller et al. |
| 10,512,474 B2 | 12/2019 | Miller et al. |
| 10,806,491 B2 | 10/2020 | Miller et al. |
| 2001/0005778 A1 | 6/2001 | Ouchi |
| 2001/0014439 A1 | 8/2001 | Meller et al. |
| 2001/0047183 A1 | 11/2001 | Privitera et al. |
| 2001/0053888 A1 | 12/2001 | Athanasiou et al. |
| 2002/0042581 A1 | 4/2002 | Cervi |
| 2002/0050364 A1 | 5/2002 | Suzuki et al. |
| 2002/0055713 A1 | 5/2002 | Gibbs |
| 2002/0091039 A1 | 7/2002 | Reinbold et al. |
| 2002/0120212 A1 | 8/2002 | Ritchart et al. |
| 2002/0133148 A1 | 9/2002 | Daniel et al. |

(56) References Cited

U.S. PATENT DOCUMENTS

| | | |
|---|---|---|
| 2002/0138021 A1 | 9/2002 | Pflueger |
| 2002/0143269 A1 | 10/2002 | Neuenfeldt |
| 2002/0151821 A1 | 10/2002 | Castellacci |
| 2002/0151902 A1 | 10/2002 | Riedel et al. |
| 2002/0158102 A1 | 10/2002 | Patton et al. |
| 2003/0028146 A1 | 2/2003 | Ayes |
| 2003/0032939 A1 | 2/2003 | Gibbs |
| 2003/0036747 A1 | 2/2003 | Ie et al. |
| 2003/0050574 A1 | 3/2003 | Krueger |
| 2003/0078586 A1 | 4/2003 | Shapira |
| 2003/0114858 A1 | 6/2003 | Athanasiou et al. |
| 2003/0125639 A1 | 7/2003 | Fisher et al. |
| 2003/0153842 A1 | 8/2003 | Lamoureux et al. |
| 2003/0191414 A1 | 10/2003 | Reiley et al. |
| 2003/0195436 A1 | 10/2003 | Van Bladel et al. |
| 2003/0195524 A1 | 10/2003 | Barner |
| 2003/0199787 A1 | 10/2003 | Schwindt |
| 2003/0199879 A1 | 10/2003 | Spranza |
| 2003/0216667 A1 | 11/2003 | Viola |
| 2003/0225344 A1 | 12/2003 | Miller |
| 2003/0225364 A1 | 12/2003 | Kraft et al. |
| 2003/0225411 A1 | 12/2003 | Miller |
| 2004/0019297 A1 | 1/2004 | Angel |
| 2004/0019299 A1 | 1/2004 | Ritchart et al. |
| 2004/0034280 A1 | 2/2004 | Privitera et al. |
| 2004/0049128 A1 | 3/2004 | Miller et al. |
| 2004/0049205 A1 | 3/2004 | Lee et al. |
| 2004/0064136 A1 | 4/2004 | Papineau et al. |
| 2004/0073139 A1 | 4/2004 | Hirsch et al. |
| 2004/0092946 A1 | 5/2004 | Bagga et al. |
| 2004/0127814 A1 | 7/2004 | Negroni |
| 2004/0153003 A1 | 8/2004 | Cicenas et al. |
| 2004/0158172 A1 | 8/2004 | Hancock |
| 2004/0158173 A1 | 8/2004 | Voegele et al. |
| 2004/0162505 A1 | 8/2004 | Kaplan et al. |
| 2004/0191897 A1 | 9/2004 | Muschler |
| 2004/0210161 A1 | 10/2004 | Burdorff et al. |
| 2004/0210198 A1 | 10/2004 | Shih |
| 2004/0215102 A1 | 10/2004 | Ikehara et al. |
| 2004/0220497 A1 | 11/2004 | Findlay et al. |
| 2005/0027210 A1 | 2/2005 | Miller |
| 2005/0033275 A1 | 2/2005 | Hoegerle et al. |
| 2005/0040060 A1 | 2/2005 | Andersen et al. |
| 2005/0075581 A1 | 4/2005 | Schwindt |
| 2005/0085838 A1 | 4/2005 | Thompson et al. |
| 2005/0101880 A1 | 5/2005 | Cicenas et al. |
| 2005/0113716 A1 | 5/2005 | Mueller, Jr. et al. |
| 2005/0116673 A1 | 6/2005 | Carl et al. |
| 2005/0119660 A1 | 6/2005 | Bourlion et al. |
| 2005/0124915 A1 | 6/2005 | Eggers et al. |
| 2005/0131345 A1 | 6/2005 | Miller |
| 2005/0148940 A1 | 7/2005 | Miller |
| 2005/0165328 A1 | 7/2005 | Heske et al. |
| 2005/0165403 A1 | 7/2005 | Miller |
| 2005/0165404 A1 | 7/2005 | Miller |
| 2005/0171504 A1 | 8/2005 | Miller |
| 2005/0182394 A1 | 8/2005 | Spero et al. |
| 2005/0200087 A1 | 9/2005 | Vasudeva et al. |
| 2005/0203439 A1 | 9/2005 | Heske et al. |
| 2005/0209530 A1 | 9/2005 | Pflueger |
| 2005/0215921 A1 | 9/2005 | Hibner et al. |
| 2005/0228309 A1 | 10/2005 | Fisher et al. |
| 2005/0236940 A1 | 10/2005 | Rockoff |
| 2005/0261693 A1 | 11/2005 | Miller et al. |
| 2006/0011506 A1 | 1/2006 | Riley |
| 2006/0015066 A1 | 1/2006 | Turieo et al. |
| 2006/0036212 A1 | 2/2006 | Miller |
| 2006/0052790 A1 | 3/2006 | Miller |
| 2006/0074345 A1 | 4/2006 | Hibner |
| 2006/0079774 A1 | 4/2006 | Anderson |
| 2006/0089565 A1 | 4/2006 | Schramm |
| 2006/0115066 A1 | 6/2006 | Levien et al. |
| 2006/0122535 A1 | 6/2006 | Daum |
| 2006/0129082 A1 | 6/2006 | Rozga |
| 2006/0144548 A1 | 7/2006 | Beckman et al. |
| 2006/0149163 A1 | 7/2006 | Hibner et al. |
| 2006/0151188 A1 | 7/2006 | Bodine et al. |
| 2006/0167377 A1 | 7/2006 | Ritchart et al. |
| 2006/0167378 A1 | 7/2006 | Miller |
| 2006/0167379 A1 | 7/2006 | Miller |
| 2006/0184063 A1 | 8/2006 | Miller |
| 2006/0189940 A1 | 8/2006 | Kirsch |
| 2006/0206132 A1 | 9/2006 | Conquergood et al. |
| 2007/0016100 A1 | 1/2007 | Miller |
| 2007/0049945 A1 | 3/2007 | Miller |
| 2007/0149920 A1 | 6/2007 | Michels et al. |
| 2007/0213735 A1 | 9/2007 | Saadat et al. |
| 2007/0270775 A1 | 11/2007 | Miller et al. |
| 2008/0015467 A1 | 1/2008 | Miller |
| 2008/0015468 A1 | 1/2008 | Miller |
| 2008/0015623 A1 | 1/2008 | Deck |
| 2008/0045857 A1 | 2/2008 | Miller et al. |
| 2008/0045860 A1 | 2/2008 | Miller et al. |
| 2008/0045861 A1 | 2/2008 | Miller et al. |
| 2008/0045965 A1 | 2/2008 | Miller et al. |
| 2008/0087448 A1 | 4/2008 | Happ |
| 2008/0140014 A1 | 6/2008 | Miller et al. |
| 2008/0177200 A1 | 7/2008 | Ikehara et al. |
| 2008/0215056 A1 | 9/2008 | Miller et al. |
| 2008/0221580 A1 | 9/2008 | Miller et al. |
| 2009/0069716 A1 | 3/2009 | Freeman et al. |
| 2009/0093677 A1 | 4/2009 | Smith |
| 2009/0194446 A1 | 8/2009 | Miller et al. |
| 2010/0204611 A1 | 8/2010 | Zambelli |
| 2011/0046507 A1 | 2/2011 | Herndon |
| 2011/0082387 A1 | 4/2011 | Miller et al. |
| 2011/0186456 A1 | 8/2011 | Bertazzoni et al. |
| 2011/0306841 A1 | 12/2011 | Lozman et al. |
| 2012/0165832 A1 | 6/2012 | Oostman, Jr. et al. |
| 2014/0262408 A1 | 9/2014 | Woodard |
| 2016/0081732 A1* | 3/2016 | Baroud ............... A61M 5/142 623/23.62 |
| 2018/0056095 A1 | 3/2018 | Messerly et al. |

FOREIGN PATENT DOCUMENTS

| | | |
|---|---|---|
| CA | 2454600 A1 | 2/2003 |
| CN | 2320209 Y | 5/1999 |
| CN | 2664675 Y | 12/2004 |
| DE | 10057931 A1 | 8/2002 |
| EP | 1447050 A2 | 8/2004 |
| FR | 2457105 A1 | 12/1980 |
| FR | 2516386 A1 | 5/1983 |
| GB | 629 824 A | 9/1949 |
| GB | 2130890 A | 6/1984 |
| JP | S59-119808 | 7/1984 |
| JP | S61-32663 A | 2/1986 |
| JP | 2001505076 A | 4/2001 |
| WO | 92/08410 A1 | 5/1992 |
| WO | 93/07819 A2 | 4/1993 |
| WO | 96/31164 A1 | 10/1996 |
| WO | 98/06337 A1 | 2/1998 |
| WO | 98/52638 A2 | 11/1998 |
| WO | 99/18866 A1 | 4/1999 |
| WO | 9952444 A1 | 10/1999 |
| WO | 00/09024 A1 | 2/2000 |
| WO | 00/056220 A1 | 9/2000 |
| WO | 01/078590 A1 | 10/2001 |
| WO | 02/041791 A | 5/2002 |
| WO | 02/041792 A1 | 5/2002 |
| WO | 02/096497 A1 | 12/2002 |
| WO | 2003/015637 A1 | 2/2003 |
| WO | 2005/072625 A2 | 8/2005 |
| WO | 05/110259 A1 | 11/2005 |
| WO | 2005/112800 A2 | 12/2005 |
| WO | 2008/033874 A2 | 3/2008 |
| WO | 08/081438 A1 | 7/2008 |
| WO | 2011/123703 A1 | 10/2011 |

OTHER PUBLICATIONS

International Preliminary Report, PCT/US2005/002484, 9 pages, dated Aug. 3, 2006.

(56) References Cited

OTHER PUBLICATIONS

International Search Report and Written Opinion for International Application No. PCT/US2006/025201 (18 pages), dated Jan. 29, 2007.
International Search Report and Written Opinion, PCT/US08/50346, 12 pages, dated May 22, 2008.
International Search Report and Written Opinion, PCT/US08/52943, 8 pages, dated Sep. 26, 2008.
International Search Report and Written Opinion, PCT/US2007/072202, 17 pages, dated Mar. 25, 2008.
International Search Report and Written Opinion, PCT/US2007/078203, 15 pages, dated May 13, 2008.
International Search Report and Written Opinion, PCT/US2007/078204, 14 pages, dated May 15, 2008.
International Search Report and Written Opinion, PCT/US2007/078205, 13 pages, dated Apr. 7, 2008.
International Search Report and Written Opinion, PCT/US2007/078207, 13 pages, dated Apr. 7, 2008.
International Search Report, PCT/US2006/025201, 12 pages, dated Feb. 7, 2008.
International Search Report, PCT/US2007/072209, 18 pages, dated Apr. 25, 2008.
International Search Report, PCT/US2007/072209, 9 pages, dated Mar. 12, 2007.
International Search Report, PCT/US2007/072217, 20 pages, dated Mar. 31, 2008.
International Search Report, PCT/US2007/072217, 9 pages, dated Mar. 12, 2007.
Interview Summary dated Jul. 13, 2009 and Response to Interview Summary and Amendment filed Aug. 12, 2009, U.S. Appl. No. 11/190,331, 17 pages.
Japanese Office Action with English Translation; Application No. 2004-508,670; PCT/US03/17203; p. 7, dated Jan. 20, 2011.
Japanese Office Action, Application No. 2004-508,669, (with English summary), (9 pgs), dated Aug. 3, 2009.
Japanese Office Action, Application No. 2004-508,670, (with English summary), (13 pgs), dated Apr. 21, 2009.
Liakat A. Parapia, Trepanning or trephines: a history of bone marrow biopsy, British Journal of Haematoloay, pp. 14-19, 2007.
Michael Trotty, "Technology (A Special Report)—The Wall Street Journal 2008 Technology Innovation Awards—This years winners include: an IV alternative, a better way to make solar panels, a cheap, fuel efficient car and a better way to see in the dark", The Wall Street Journal, Factiva, 5 pages, 2008.
Non-Final Office Action dated Apr. 1, 2009 and Response to Office Action filed Jul. 1, 2009, U.S. Appl. No. 10/449,503, 19 pages.
Non-Final Office Action dated Mar. 23, 2009 and Response to Office Action filed Jun. 22, 2009, U.S. Appl. No. 11/190,331, 61 pages.
Non-Final Office Action dated May 13, 2009 and Response to Office Action filed Jul. 1, 2009, U.S. Appl. No. 11/427,501, 23 pages.
Non-Final Office Action, U.S. Appl. No. 10/449,476, 6 pages, dated May 29, 2009.
Non-Final Office Action, U.S. Appl. No. 10/449,476, 8 pages, dated Oct. 29, 2008.
Non-Final Office Action, U.S. Appl. No. 10/987,051, 9 pages, dated Nov. 10, 2009.
Non-Final Office Action, U.S. Appl. No. 11/042,912, 8 pages, dated Jul. 23, 2009.
Non-Final Office Action, U.S. Appl. No. 12/259,745,11 pages, dated Jul. 17, 2009.
Notice of Allowance dated Mar. 4, 2014 in U.S. Appl. No. 11/253,467.
Notice of Allowance in U.S. Appl. No. 11/042,912, dated Sep. 24, 2013.
Notice of Allowance in U.S. Appl. No. 11/619,390 dated Jul. 3, 2014.
Notice of Allowance in U.S. Appl. No. 11/620,927 dated Jun. 3, 2014.
Notice of Allowance in U.S. Appl. No. 11/853,678 dated Jul. 11, 2013.
Notice of Allowance in U.S. Appl. No. 11/853,678, dated Nov. 8, 2013.
Notice of Allowance in U.S. Appl. No. 12/331,979, dated Dec. 23, 2013.
Notice of Allowance in U.S. Appl. No. 12/407,651 dated Jun. 11, 2014.
Notice of Allowance in U.S. Appl. No. 12/427,310, dated Nov. 29, 2013.
Notice of Allowance in U.S. Appl. No. 12/899,696 dated Jul. 18, 2013.
Notice of Allowance in U.S. Appl. No. 12/899,696, dated Nov. 12, 2013.
Notice of Allowance issued in U.S. Appl. No. 11/042,912, dated Mar. 27, 2013.
Notice of Allowance issued in U.S. Appl. No. 11/042,912, dated Oct. 5, 2012.
Notice of Allowance issued in U.S. Appl. No. 11/253,467, dated Mar. 29, 2013.
Notice of Allowance issued in U.S. Appl. No. 11/253,959, dated May 20, 2013.
Notice of Allowance issued in U.S. Appl. No. 11/253,959, dated Mar. 14, 2013.
Notice of Allowance issued in U.S. Appl. No. 11/853,678, dated Mar. 27, 2013.
Notice of Allowance issued in U.S. Appl. No. 11/853,701, dated Mar. 14, 2013.
Notice of Allowance issued in U.S. Appl. No. 12/427,310, dated Jun. 5, 2013.
Notice of Allowance issued in U.S. Appl. No. 12/718,606, dated Mar. 6, 2013.
Notice of Allowance issued in U.S. Appl. No. 12/718,606, dated Oct. 11. 2012.
Notice of Allowance dated Jul. 11, 2012 in U.S. Appl. No. 12/554,708.
Notice of Allowance dated Jul. 20, 2012 in U.S. Appl. No. 12/554,664.
Notice of Allowance dated Jun. 22, 2012 in U.S. Appl. No. 11/042,912.
Notice of Allowance dated Mar. 14, 2013 in U.S. Appl. No. 11/253,959.
Notice of Allowance dated Mar. 14, 2013 in U.S. Appl. No. 11/853,701.
Notice of Allowance dated Mar. 27, 2013 in U.S. Appl. No. 11/042,912.
Notice of Allowance dated Mar. 27, 2013 in U.S. Appl. No. 11/853,678.
Notice of Allowance dated Mar. 29, 2013 in U.S. Appl. No. 11/253,467.
Notice of Allowance dated Mar. 6, 2013 in U.S. Appl. No. 12/718,606.
Notice of Allowance dated Oct. 11, 2012 in U.S. Appl. No. 12/718,606.
Notice of Allowance dated Oct. 5, 2012 in U.S. Appl. No. 11/042,912.
Notification of the First Chinese Office Action, Application No. 200580003261.8, 3 pages, dated Mar. 21, 2008.
Office Action (and Search Report) for European application 09150973.7. dated Oct. 23, 2009.
Office Action for Chinese application 200880000182.5 (English translation). dated Jun. 27, 2013.
Office Action for Chinese application 201210169456.0 with English translation. dated Aug. 28, 2013.
Office Action for European application 08021732.6. dated Oct. 2, 2013.
Office Action for Japanese application 2004-508,670 (English summary). dated Apr. 21, 2009.
Office Action for U.S. Appl. No. 11/042,912, dated Mar. 19, 2010.
Office Action for U.S. Appl. No. 11/253,467, dated Apr. 28, 2011.
Office Action for U.S. Appl. No. 11/253,467, dated Jul. 22, 2010.
Office Action for U.S. Appl. No. 11/253,959, dated Mar. 30, 2011.
Office Action for U.S. Appl. No. 12/905,659, dated Mar. 21, 2011.
Office Action for U.S. Appl. No. 12/905,659, dated May 13, 2011.
Office Action issued in Chinese Application No. 200910006631.3, dated Mar. 22, 2011.
Office Communication in European Application No. 08021732.6, dated Jun. 20, 2013.

(56) References Cited

OTHER PUBLICATIONS

Office Communication issued in Chinese Patent Application No. 200910138130.0, dated Oct. 10, 2011.
Office Communication issued in European Patent Application No. 09150973.7, dated Dec. 22, 2011.
Official Action for European Application No. 03756317.8 (4 pages), dated Dec. 28, 2006.
PCT Invitation to Pay Additional Fees, PCT/US2007/072209, 9 pages, dated Dec. 3, 2007.
PCT Preliminary Report on Patentability, PCT/US/2008/050346, (8 pgs.), dated Jul. 23, 2009.
Pediatric Emergency, Intraosseous Infusion for Administration of Fluids and Drugs, www.cookgroup.com, 1 pg., 2000.
Pediatrics, "2005 American Heart Association Guidelines for Cardiopulmonary Resuscitation and Emergency cardiovascular Care of Pediatric and Neonatal Patients: Pediatric Advanced Life Support," www.pediatrics.org, Official Journal of the American Academy of Pediatrics (26 pages), Feb. 21, 2007.
R.S. Riley et al.; "A Pathologists Perspective on Bone Marrow Aspiration and Biopsy: I. Performing a Bone Marrow Examination"; Journal of Clinical Laboratory Analysis, vol. 18; pp. 70-90, 2004.
Request for Continued Examination and Amendment, U.S. Appl. No. 11/064,156, 22 pages, dated Nov. 19, 2009.
Request for Continued Examination and Amendment, U.S. Appl. No. 11/781,568, (9 pgs.), dated Sep. 17, 2009.
Response to May 29, 2009 Office Action filed Aug. 12, 2009, U.S. Appl. No. 10/449,476, 14 pages.
Response to Non-Final Office Action, U.S. Appl. No. 11/042,912, (11 pgs.), dated Oct. 23, 2009.
Riley et al., "A Pathologists Perspective on Bone Marrow Aspiration Biopsy: I Performing a Bone Marrow Examination," Journal of Clinical Laboratory Analysis 18, pp. 70-90, 2004.
State Intellectual Property Office of the Peoples Republic of China, First Office Action issued for Chinese Patent Application No. 200880000182.5, dated Sep. 10, 2010.
State Intellectual Property Office of the PeopleS Republic of China, Reexamination Decision Issued for Chinese Patent Application No. 200880000182.5, dated Nov. 20, 2013.
State Intellectual Property Office of the PeopleS Republic of China, Rejection Decision issued for Chinese Patent Application No. 200880000182.5, dated Jun. 27, 2013.
State Intellectual Property Office of the Peoples Republic of China, Second Office Action issued for Chinese Patent Application No. 200880000182.5, dated Mar. 12, 2012.
State Intellectual Property Office of the PeopleS Republic of China, Third Office Action issued for Chinese Patent Application No. 200880000182.5, dated Dec. 13, 2012.
Taiwan Office Action, Application No. 94102179 (with English translation); 12 pages, dated May 13, 2010.
Non-Final Office Action for U.S. Appl. No. 11/427,501, 14 pages, dated Aug. 7, 2008.
Vidacare Corporation Comments to Intraosseous Vascular Access Position Paper, Infusion Nurses Society, 6 pages, May 4, 2009.
"Proven reliability for quality bone marrow samples", Special Procedures, Cardinal Health, 6 pages, 2003.
Astrom, K. Gunnar O., "CT-guided Transstemal Core Biopsy of Anterior Mediastinal Masses," Radiology 1996; 199:564-567, May 1996.
Astrom, K.G., "Automatic Biopsy Instruments Used Through a Coaxial Bone Biopsy System with an Eccentric Drill Tip," Acta Radiologica, 1995; 36:237-242, May 1995.
Australian Exam Report on Patent Application No. 2003240970, 2 pages, dated Oct. 15, 2007.
BioAccess.com, Single Use Small Bone Power Tool—How It Works, 1 pg, printed Jun. 9, 2008.
Buckley et al., "CT-guided bone biopsy: initial experience with commercially available hand held Black and Decker kill," European Journal of Radiology 61:176-180. 2007.
Chinese Office Action with English translation; Application No. 2007800011983; p. 13, dated Apr. 27, 2010.
Chinese Office Action with English translation; Application No. 200880000182.5; 12 pages, dated Sep. 10, 2010.
Chinese Office Action with English translation; Application No. 200910006631.3; 12 pages, dated Mar. 11, 2010.
Chinese Office Action, Application No. 2005800003261, (with English translation), (9 pgs.), dated Jan. 16, 2009.
Chinese Office Action, Application No. 200780000590.6, (with English translation), 13 pages, dated Aug. 21, 2009.
Communication Pursuant to Article 94(3) EPC, Application No. 05 712 091.7-1265, 4 pages, dated Apr. 8, 2008.
Communication relating to the results of the partial International Search Report for PCT/US2005/002484, 6 pages, dated May 19, 2005.
Cummins, Richard O., et al., "ACLS-Principles and Practice", ACLS—The Reference Textbook, American Heart Association, pp. 214-218, 2003.
European Extended Search Report, Application No. EP08021732.6, 7 pages, dated Nov. 13, 2009.
European Extended Search Report, Application No. EP10153350.3, 5 pages, dated Mar. 11, 2010.
European Office Action and Search Report, Application No. 09150973. 7, 8 pages, dated Oct. 23, 2009.
European Office Action Communication, Application No. 08158699. 2-1265/1967142, 10 pages, dated Nov. 4, 2008.
European Office Action EP03731475.4, 4 pages, dated Oct. 11, 2007.
European Office Action dated Dec. 22, 2011 and Response sent Jun. 29, 2012, EP Application No. 09150973.7.
European Office Action dated Jan. 19, 2011 and Response sent Jul. 21, 2011, EP Application No. 09150973.7.
European Office Action; Application No. 09 155 111.0-2310; 3 pages, dated Nov. 25, 2009.
European Patent Office, Communication from Examining Division for European Patent Application No. 08799753.2, dated Apr. 10, 2014.
European Patent Office, Communication from Examining Division for European Patent Application No. 08799753.2, dated May 18, 2015.
European Patent Office, Communication from Examining Division for European Patent Application No. 08799753.2, dated Sep. 29, 2014.
European Patent Office, European Search Report for European Patent Application No. 08799753.2, dated May 23, 2013.
European Search Report 08158699.2-1265, 4 pages, dated Aug. 2008.
European Search Report issued in European Patent Application No. 17198059.2 dated Jan. 29, 2018.
F.A.S.T. 1 Intraosseous Infusion System with Depth-Control Mechanism Brochure, 6 pages, 2000.
Final Office Action, U.S. Appl. No. 11/064,156, 12 pages, dated Jun. 19, 2009.
Final Office Action, U.S. Appl. No. 11/427,501, (10 pgs.), dated Oct. 21, 2009.
Final Office Action, U.S. Appl. No. 11/781,568, 19 pages, dated Jun. 17, 2009.
Final Office Action, U.S. Appl. No. 11/781,597, 14 pages, dated Nov. 17, 2009.
Final Office Action, U.S. Appl. No. 11/853,685, 21 pages, dated Jun. 24, 2009.
Gunal et al., Compartment Syndrome After Intraosseous Infusion: an Experimental Study in Dogs, Journal of Pediatric Surgery, vol. 31, No. 11, pp. 1491-1493, Nov. 1996.
Hakan et al., CT-guided Bone Biopsy Performed by Means of Coaxial Biopsy System with an Eccentric Drill, Radiology, pp. 549-552, Aug. 1993.
International PCT Search Report and Written Opinion PCT/US2004/ 037753, 16 pages, dated Jul. 8, 2005.
International PCT Search Report and Written Opinion PCT/US2005/ 002484, 15 pages, dated Jul. 22, 2005.
International PCT Search Report PCT/US03/17167, 8 pages, dated Sep. 16, 2003.

(56) References Cited

OTHER PUBLICATIONS

International PCT Search Report PCT/US03/17203, 8 pages, dated Sep. 16, 2003.
International PCT Search Report PCT/US2004/037753, 6 pages, dated Apr. 19, 2005.
International Preliminary Report on Patentability for international application PCT/US20071072202. dated Jan. 15, 2009.
International Preliminary Report on Patentability PCT/US2005/002484, 9 pages, dated Aug. 3, 2006.
International Preliminary Report on Patentability, PCT/US/2007/072209, 10 pages, dated May 14, 2009.
International Preliminary Report on Patentability, PCT/US/2007/078203, 13 pages, dated Mar. 26, 2009.
International Preliminary Report on Patentability, PCT/US/2007/078204, 11 pages, dated Apr. 2, 2009.
International Preliminary Report on Patentability, PCT/US/2007/078205, 10 pages, dated Mar. 26, 2009.
International Preliminary Report on Patentability, PCT/US/2007/078207, 10 pages, dated Mar. 26, 2009.
International Preliminary Report on Patentability, PCT/US08152943, 7 pages, dated Oct. 15, 2009.
International Preliminary Report on Patentability, PCT/US2007/072202, 10 pages, dated Jan. 15, 2009.

* cited by examiner

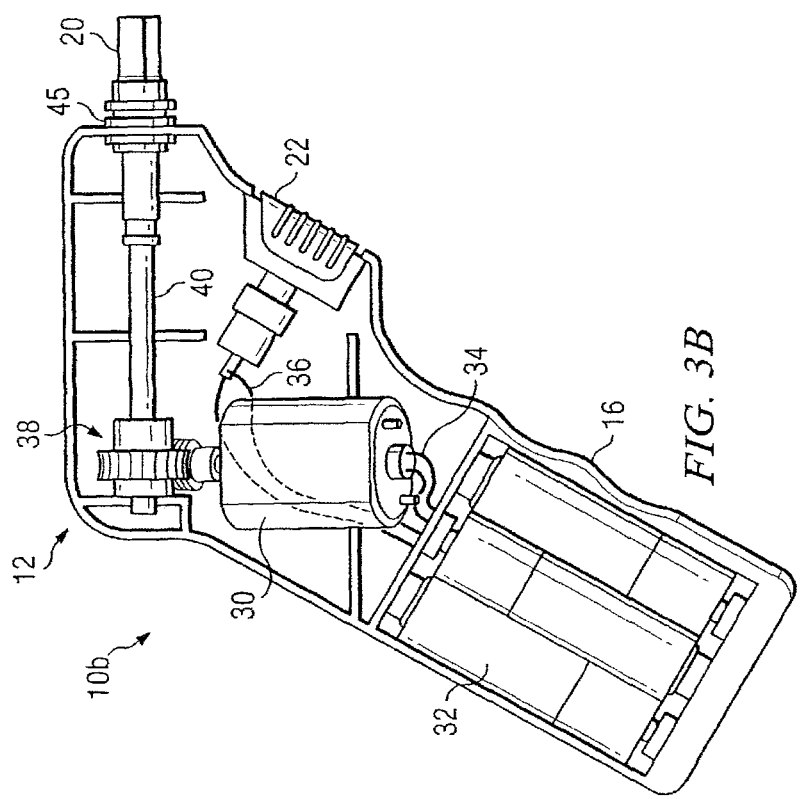
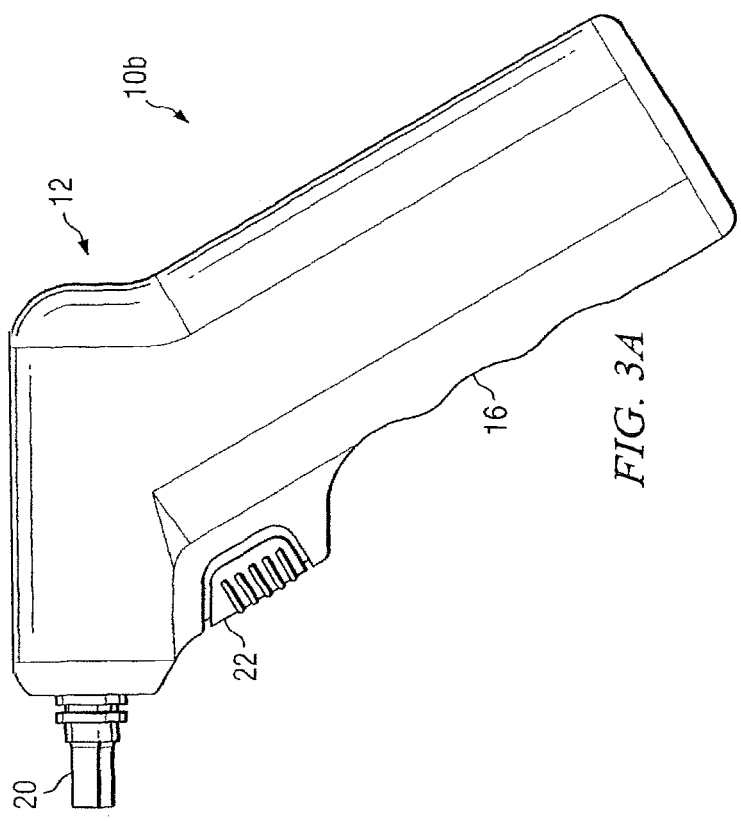
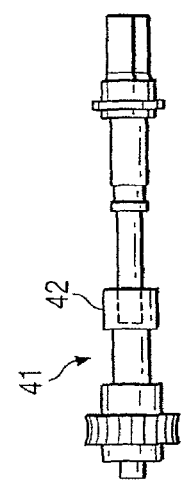
FIG. 3B
FIG. 3A
FIG. 3C

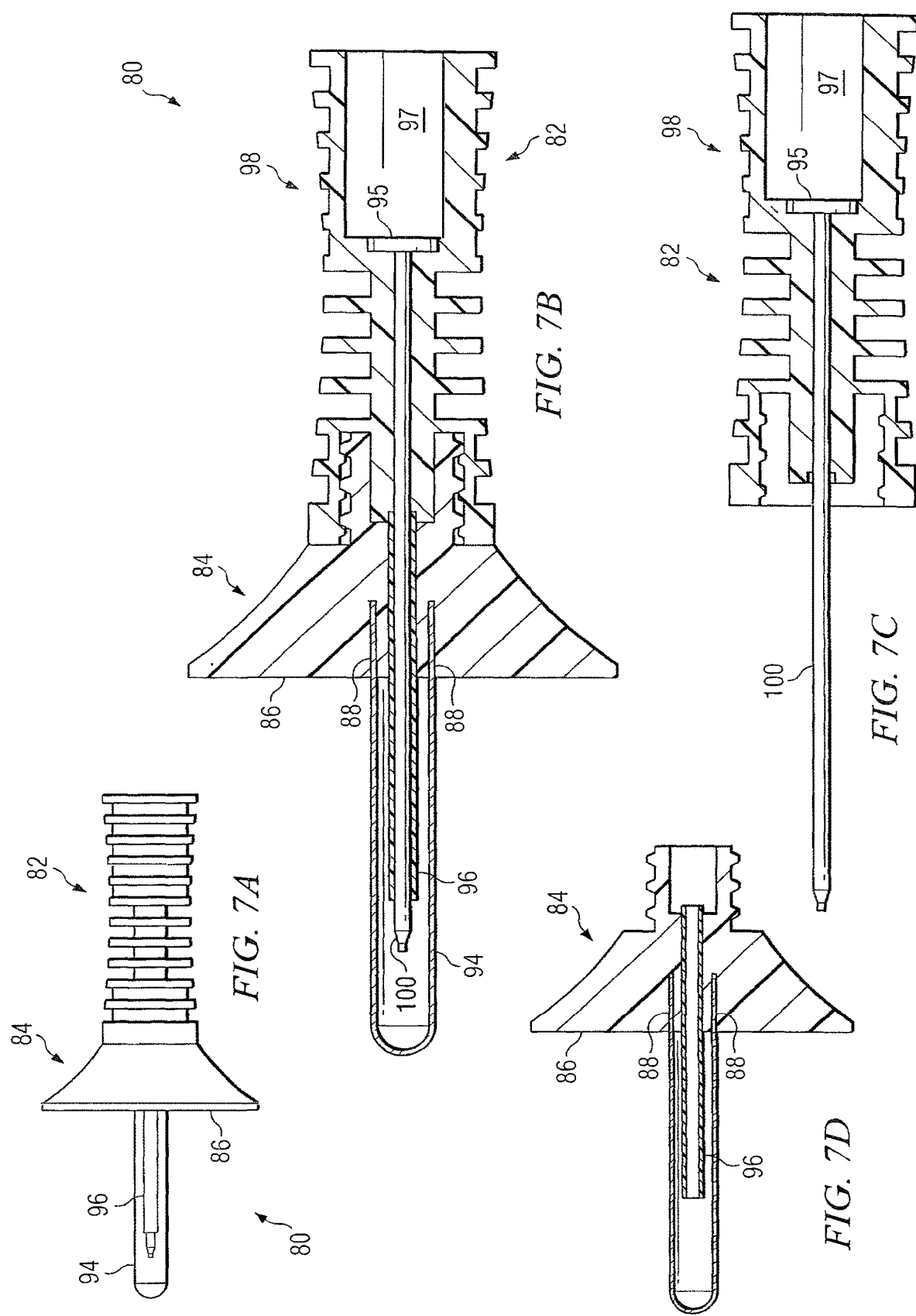

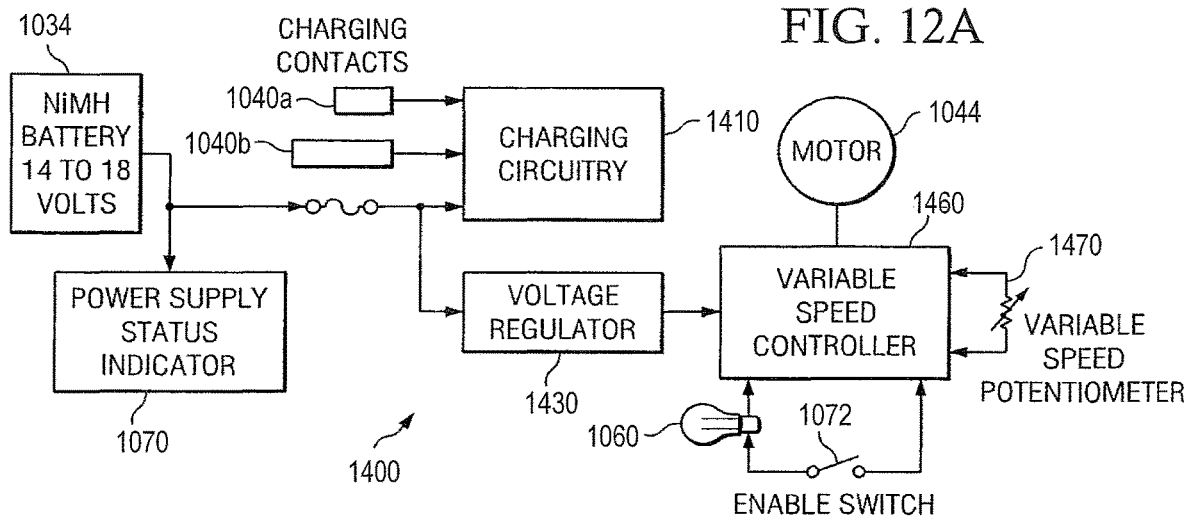
FIG. 12A
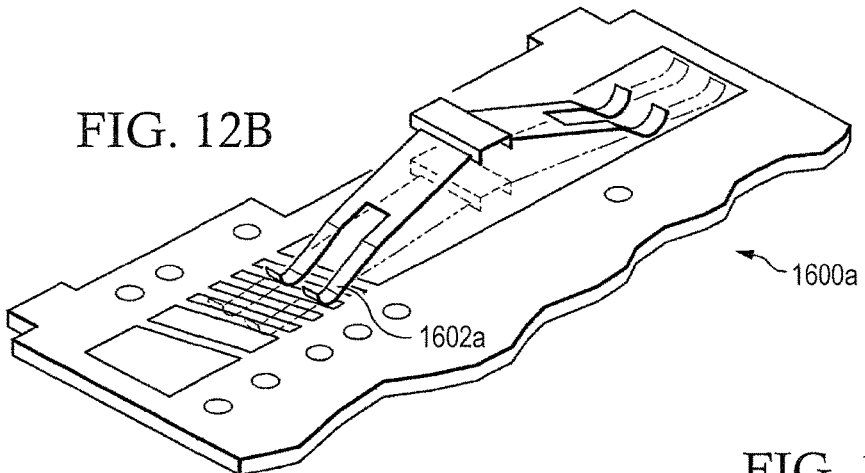
FIG. 12B
FIG. 12C
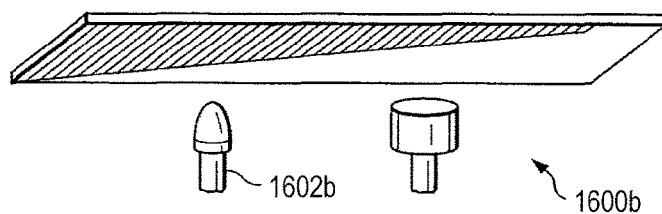
FIG. 12D
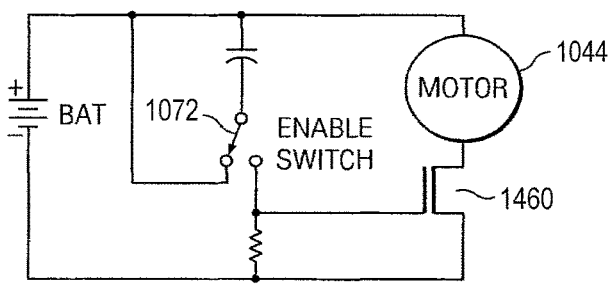

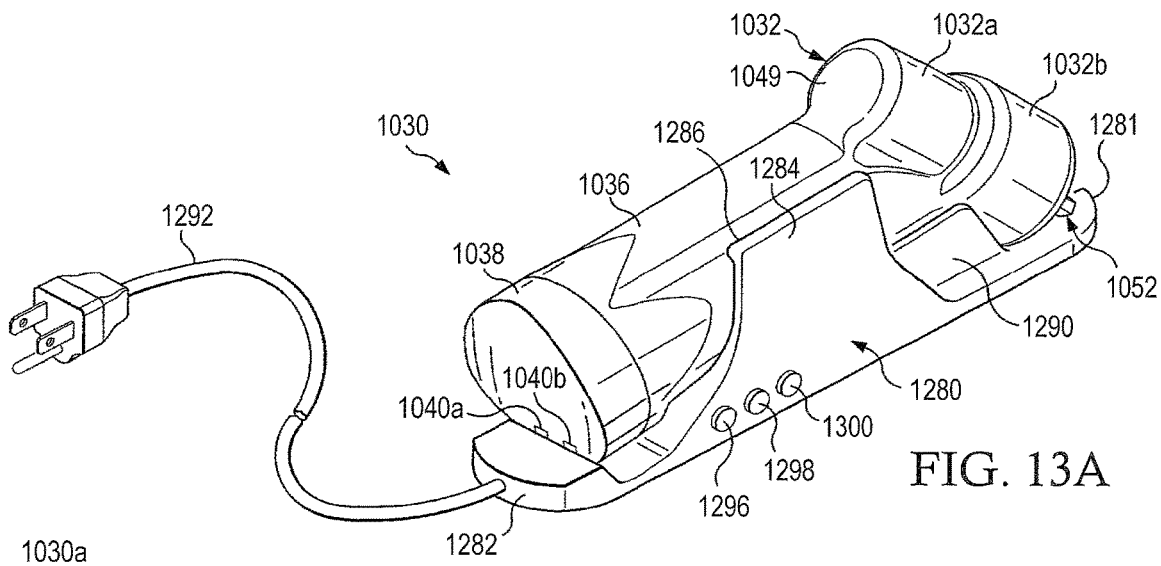
FIG. 13A
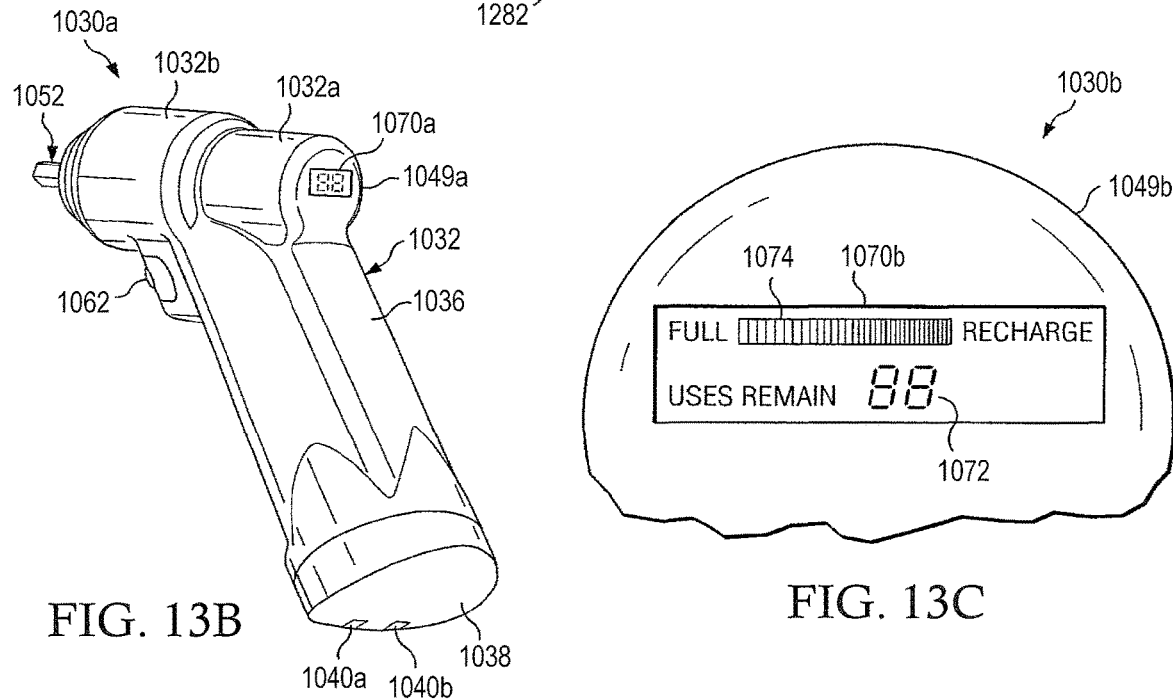
FIG. 13B
FIG. 13C
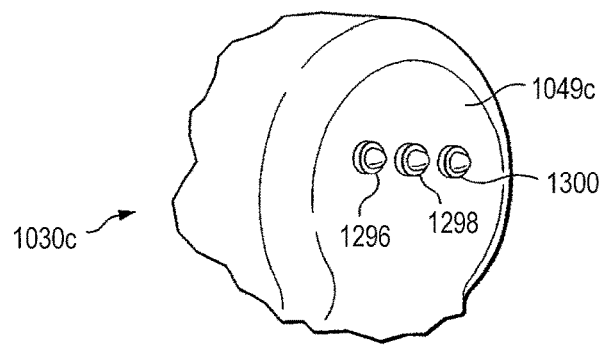
FIG. 13D

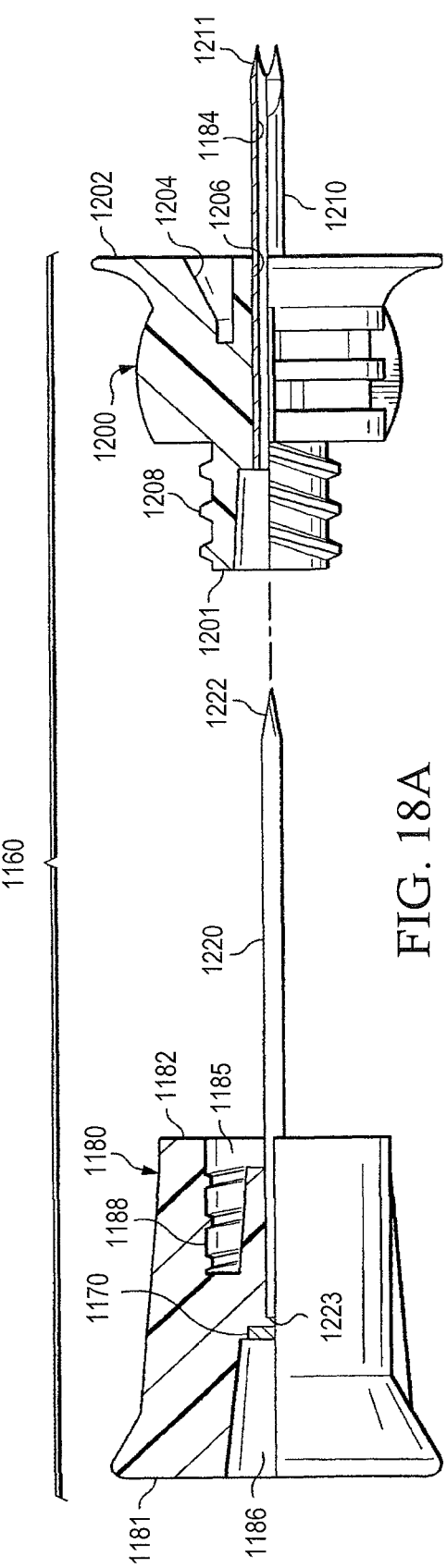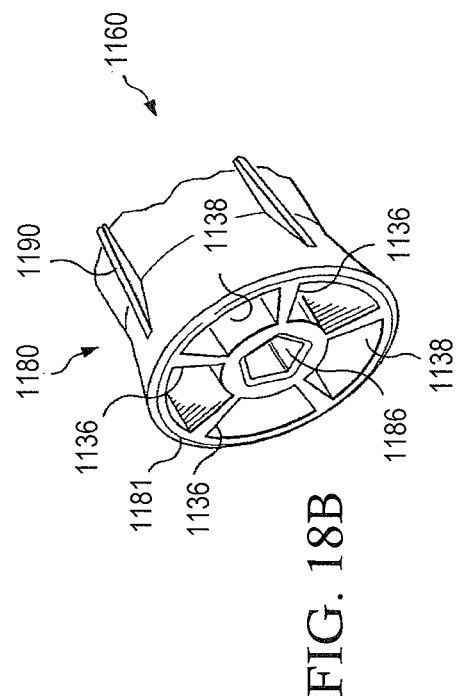
FIG. 18A
FIG. 18B

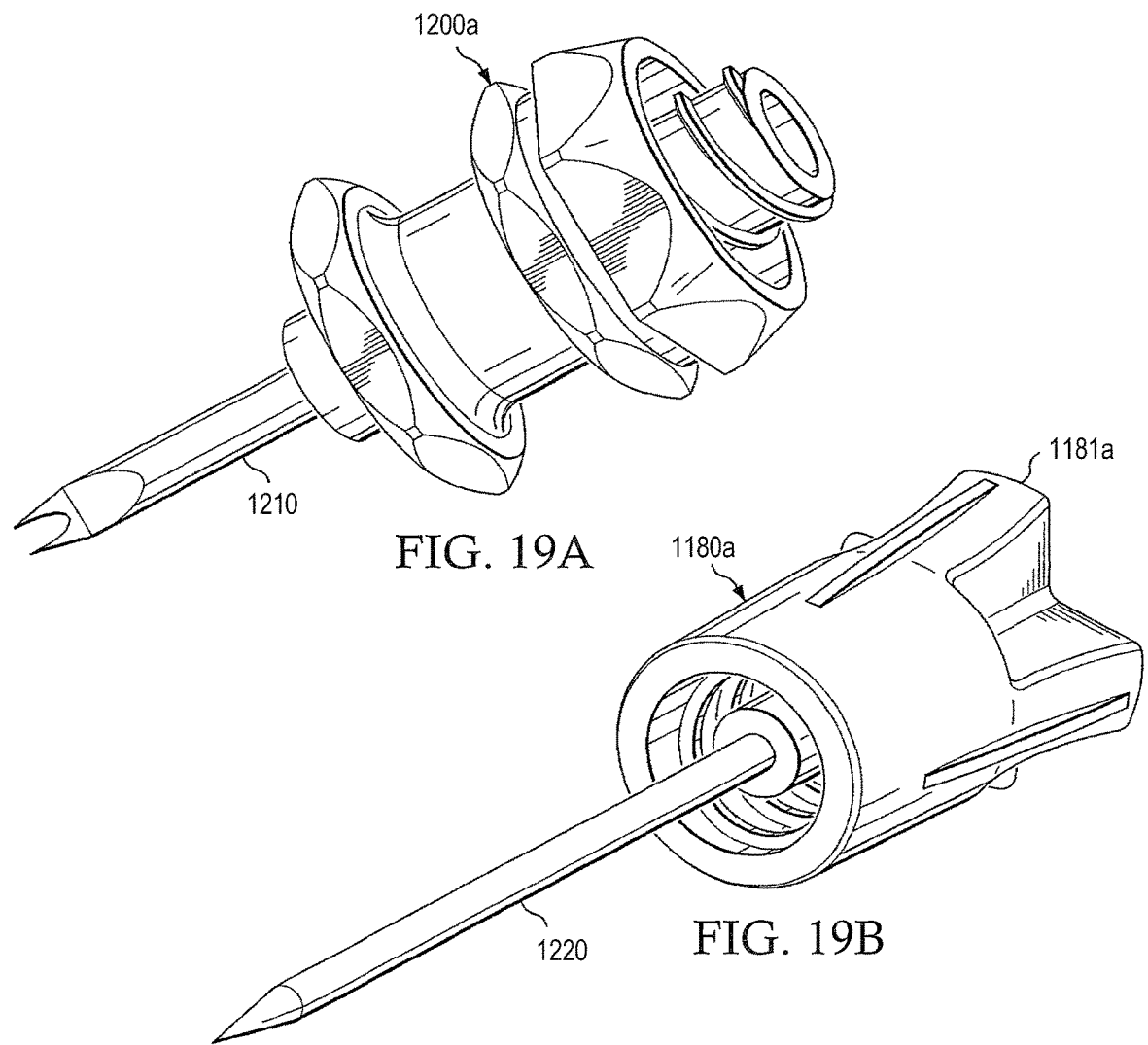
FIG. 19A
FIG. 19B
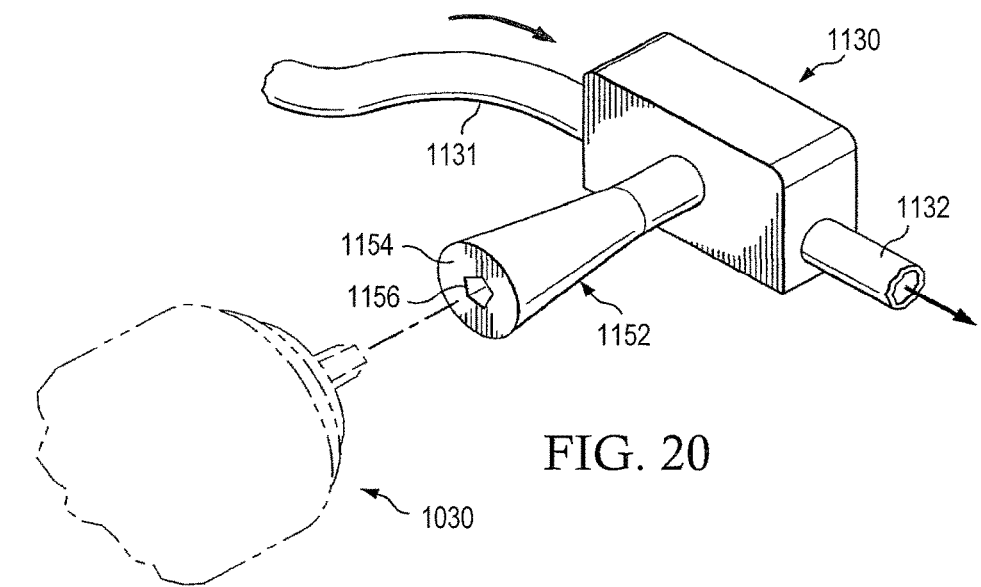
FIG. 20

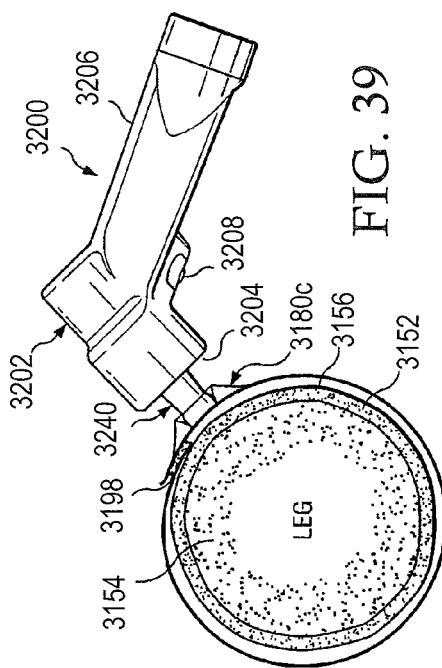
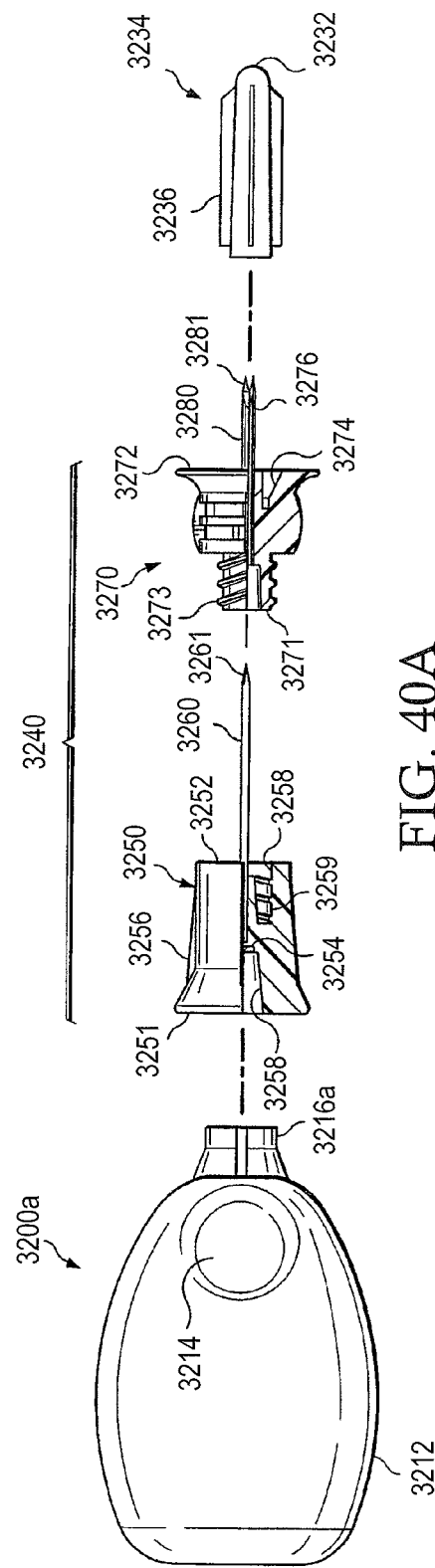
FIG. 39
FIG. 40A

POWERED DRIVERS, INTRAOSSEOUS DEVICES AND METHODS TO ACCESS BONE MARROW

CROSS-REFERENCE TO RELATED APPLICATIONS

The present application is a continuation-in-part of pending U.S. patent application Ser. No. 16/725,939, entitled "Powered Drivers, Intraosseous Devices And Methods To Access Bone Marrow," filed Dec. 23, 2019, now published as U.S. Patent Application Publication No. 2020/0129186, which is a continuation of U.S. patent application Ser. No. 15/272,647, entitled "Powered Drivers, Intraosseous Devices And Methods To Access Bone Marrow," filed Sep. 22, 2016, now U.S. Pat. No. 10,512,474, which is continuation of U.S. patent application Ser. No. 12/061,944, entitled "Powered Drivers, Intraosseous Devices and Methods to Access Bone Marrow," filed on Apr. 3, 2008, now U.S. Pat. No. 9,451,968, which claims priority to U.S. Provisional Patent Application No. 60/910,122, entitled "Powered Drivers, Intraosseous Device and Methods to Access Bone Marrow," filed Apr. 4, 2007; and U.S. patent application Ser. No. 12/061,944 is a continuation-in-part of U.S. patent application Ser. No. 11/253,959, entitled "Method and Apparatus to Access Bone Marrow," filed Oct. 19, 2005, now U.S. Pat. No. 8,506,568, and is a continuation-in-part of U.S. patent application Ser. No. 11/253,467, entitled "Apparatus and Method to Access Bone Marrow," filed Oct. 19, 2005, now U.S. Pat. No. 8,876,826, and is a continuation-in-part of U.S. patent application Ser. No. 10/449,476, entitled "Apparatus and Method to Access Bone Marrow," filed May 30, 2003, now U.S. Pat. No. 7,699,850, which claims priority to U.S. Provisional Patent Application No. 60/384,756, entitled "Apparatus and Method to Provide Access to Bone Marrow," filed May 31, 2002.

The present application is also a continuation-in-part of pending U.S. patent application Ser. No. 15/854,406, entitled "Vascular Access Kits and Methods," filed Dec. 26, 2017, now published as U.S. Patent Application Publication No. 2018/0132894, which is a divisional application of U.S. patent application Ser. No. 14/791,654, entitled "Vascular Access Kits and Methods," filed Jul. 6, 2015, now U.S. Pat. No. 9,872,703, which is a continuation of U.S. patent application Ser. No. 11/380,340, entitled "Vascular Access Kits and Methods," filed Apr. 26, 2006, now U.S. Pat. No. 9,072,543, which claims the benefit of U.S. Provisional Patent Application No. 60/675,246, entitled "Vascular Access Kit," filed Apr. 27, 2005, and which is a continuation-in-part application of U.S. application Ser. No. 10/449,503, entitled "Apparatus And Method To Provide Emergency Access To Bone Marrow," filed May 30, 2003, now U.S. Pat. No. 7,670,328, which claims the benefit of U.S. Provisional Patent Application No. 60/384,756, entitled "Apparatus and Method to Provide Access to Bone Marrow," filed May 31, 2002.

The entire contents of each of the above-referenced applications are incorporated herein by reference in their entirety.

TECHNICAL FIELD

The present disclosure is related in general to medical devices operable to access bone marrow, and more specifically to an apparatus and method for penetrating a bone and associated bone marrow with a powered driver, inserting an intraosseous device into the bone and associated bone marrow, and providing access to the bone, bone marrow, and other portions of a patient's vascular system.

BACKGROUND

Every year, millions of patients are treated for life-threatening emergencies in the United States. Such emergencies include shock, trauma, cardiac arrest, drug overdoses, diabetic ketoacidosis, arrhythmias, burns, and status epilepticus just to name a few. For example, according to the American Heart Association, more than 1,500,000 patients suffer from heart attacks (myocardial infarctions) every year, with over 500,000 of them dying from its devastating complications.

Obtaining satisfactorily vascular access may be a critical problem in approximately five (5%) percent to ten (10%) percent of patients treated in either prehospital or hospital settings. In the U.S. approximately six million patients annually may experience problems with traditional intravenous (IV) access. An essential element for treating all such emergencies is the rapid establishment of an intravenous line in order to administer drugs and fluids directly into the circulatory system. Whether in the ambulance by paramedics, or in the emergency room by emergency specialists, the goal is the same—to start an IV in order to administer life-saving drugs and fluids. To a large degree, the ability to successfully treat such critical emergencies is dependent on the skill and luck of the operator in accomplishing vascular access.

While it is relatively easy to start an IV on some patients, doctors, nurses and paramedics often experience great difficulty establishing IV access in approximately twenty (20%) percent of patients. These patients are probed repeatedly with sharp needles in an attempt to solve this problem and may require an invasive procedure to finally establish an intravenous route. A further complicating factor in achieving IV access occurs "in the field" e.g. at the scene of an accident or during ambulance transport where it is difficult to see the target and excessive motion make accessing the venous system very difficult. The success rate on the battlefield is often much lower where Army medics may only be about twenty-nine (29%) percent successful in starting an IV line during emergency conditions in the field. These patients are probed repeatedly with sharp needles in an attempt to solve this problem and may require an invasive procedure to finally establish an intravenous route.

In the case of some patients (e.g., those with chronic disease or the elderly), the availability of easily-accessible veins may be depleted. Other patients may have no available IV sites due to anatomical scarcity of peripheral veins, obesity, extreme dehydration, and/or previous IV drug use. For these patients, finding a suitable site for administering lifesaving drugs becomes a monumental and frustrating task. While morbidity and mortality statistics are not generally available, it is known that many patients with life-threatening emergencies have died of ensuing complications because access to the vascular system with life-saving IV therapy was delayed or simply not possible. For such patients, an alternative approach is required.

An accepted alternative route to give IV medications and fluids is through bone marrow by providing intraosseous (IO) access. Drugs and other fluids may enter a patient's vascular system just as rapidly via the intraosseous route as when given intravenously. Bone and associated bone marrow may be considered a large non-collapsible vein. The intraosseous route has been used for alternative emergency access in pediatric patients, whose bones are soft enough to permit manual insertion of intraosseous needles.

Powered drivers associated with intraosseous devices typically include a housing with various types of motors and/or gear assemblies disposed therein. A rotatable shaft may be disposed within the housing and connected with a gear assembly. Various types of fittings, connections, connectors and/or connector receptacles may be provided at one end of the rotatable shaft extending from the housing to releasably engage an intraosseous device with the powered driver.

Vascular system access may be essential for treatment of many serious diseases, chronic conditions and acute emergency situations. Yet, many patients experience extreme difficulty obtaining effective treatment because of inability to obtain or maintain IV access. An intraosseous space provides a direct conduit to a patent's vascular system and systemic circulation. Therefore, intraosseous access is generally an effective route to administer a wide variety of drugs, other medications and fluids equivalent to IV access. Rapid intraosseous access offers great promise for almost any serious emergency that requires vascular access to administer life saving drugs, other medications and/or fluids when traditional IV access is difficult or impossible.

Bone marrow typically includes blood, blood forming cells, and connective tissue disposed in an intraosseous space or cavity surrounded by compact bone. Long bones such as the tibia typically have an elongated central cavity filled with yellow bone marrow and adipose or connective tissue. Such cavities may also be referred to as a "medullary cavity," "bone marrow cavity" and/or "intraosseous space."

Compact bone disposed nearer the anterior or dorsal surface shall be referred to as "anterior compact bone" or "anterior bone cortex." Compact bone disposed farther from the dorsal or anterior surface may be referred to as "posterior compact bone" or "posterior bone cortex."

The upper tibia proximate a patient's knee or the humeral head proximate a patient's shoulder may be used as insertion sites for an intraosseous device to establish access with the patient's vascular system. Sternal access may also be used as an insertion site. Availability of multiple intraosseous insertion sites and associated target areas in adjacent bone marrow have proven to be especially important in applications such as emergency treatment of battlefield casualties or other mass casualty situations. Teachings of the present disclosure may be used at a wide variety of insertion sites and target areas. Teachings of the present disclosure are not limited to power drivers and/or intraosseous devices which may be inserted at the proximal tibia, distal tibia, humerus, or sternum.

Intraosseous access may be used as a "bridge" for temporary fluid and/or drug therapy during emergency conditions until conventional IV sites can be found and used. Conventional IV sites often become available because fluids and/or medication provided via intraosseous access may stabilize a patient and expand veins and other portions of a patient's vascular system. Intraosseous devices and associated procedures incorporating teachings of the present disclosure may become standard care for administering medications and fluids in situations when IV access is difficult or not possible.

Intraosseous access may be used as a "routine" procedure with chronic conditions which substantially reduce or eliminate availability of conventional IV sites. Examples of such chronic conditions may include, but are not limited to, dialysis patients, patients in intensive care units and epilepsy patients. Intraosseous devices and associated apparatus incorporating teachings of the present disclosure may be quickly and safely used to provide intraosseous access to a patient's vascular system in difficult cases such as status epilepticus to give medical personnel an opportunity to administer crucial medications and/or fluids. Further examples of such acute and chronic conditions are listed near the end of this written description.

SUMMARY

In accordance with teachings of the present disclosure, apparatus and methods are provided for gaining rapid access to a patient's bone marrow and vascular system.

In one embodiment, an apparatus for penetrating a bone marrow is provided that includes a housing and a penetrator assembly. The penetrator assembly is operable to penetrate the bone marrow, having a removable inner trocar and an outer penetrator. A connector operable to releasably attach the penetrator assembly to a drill shaft is included. The drill shaft is operable to connect the penetrator assembly to a gear assembly. The gear assembly is operable to engage and rotate the drill shaft. A motor operable to engage the gear assembly and drive the penetrator into the bone marrow by rotation of the drill shaft and a power supply and associated circuitry operable to power the motor are also included. The power supply may comprise at least one rechargeable battery.

In another embodiment, an apparatus for penetrating a bone marrow is provided that includes a housing and a penetrator assembly, operable to penetrate the bone marrow. A connector operable to releasably attach the penetrator assembly to a drill shaft, the drill shaft operable to connect the penetrator assembly to a reduction gear assembly is included. A reduction gear assembly operable to engage and rotate the drill shaft and a motor operable to engage the reduction gear assembly and drive the penetrator into the bone marrow by rotation of the drill shaft are also included. A power supply and associated circuitry operable to power the motor are also provided. The power supply may comprise at least one rechargeable battery.

In one embodiment, a penetrator assembly operable to provide access to a bone marrow comprising an outer penetrator and a removable inner trocar operable to penetrate the bone marrow is provided. A connector operable to releasably attach the penetrator assembly to a power drill is also included.

In another embodiment, a penetrator assembly operable to provide access to a bone marrow comprising an outer penetrator and a removable inner trocar operable to penetrate the bone marrow is provided. The inner trocar includes a handle, the handle including a grasping means that allows a user to grasp and manipulate the device. The outer penetrator includes a handle, the handle including a grasping means, and also includes a flange operable to engage an insertion site proximate the bone marrow. A connector operable to releasably attach the penetrator assembly to a power drill is also provided. The inner trocar is operable to releasably engage the connector.

In one embodiment, a method of accessing a bone marrow is provided that includes inserting a penetrator assembly into the bone marrow by means of a powered apparatus, detaching the powered apparatus from the penetrator, removing an inner trocar from an outer penetrator of the assembly and attaching a right angle connector to the outer penetrator.

In another embodiment, a method of accessing a bone marrow is provided that includes inserting a penetrator assembly into the bone marrow by means of a powered apparatus, detaching the powered apparatus from the penetrator, removing an inner trocar from an outer penetrator of the assembly and attaching an adapter suitable to convey medications or fluids to the bone marrow.

In yet another embodiment, a method of manufacturing an apparatus operable to penetrate a bone marrow is provided that includes manufacturing a housing having a connector operable to releasably attach a penetrator assembly to a drill shaft, a drill gear assembly, a gear assembly operable to engage and rotate the drill shaft, a motor operable to engage the gear assembly and drive a penetrator assembly into the bone marrow and a power supply and associated circuitry operable to power the motor and manufacturing a penetrator assembly operable to releasably attach to the connector. The power supply may comprise at least one rechargeable battery.

In a further embodiment, a kit for use in penetrating a bone marrow in an extremity is provided that includes a carrying case, an apparatus for penetrating the bone marrow including a housing and penetrator assemblies operable to penetrate the bone marrow, a removable inner trocar and an outer penetrator forming portions of at least one of the penetrator assemblies, at least one connector operable to releasably attach the penetrator assemblies to a drill shaft, a gear assembly operable to engage and rotate the drill shaft, a motor operable to engage the reduction gear assembly and drive at least one of the penetrator assemblies into the bone marrow and a power supply and associated circuitry to power the motor and a strap operable to immobilize the outer penetrator to a site in an extremity. The power supply may comprise at least one rechargeable battery.

One embodiment may include a powered driver operable to insert an intraosseous device into a patient's bone marrow at a selected target site. The powered driver may include a variable speed mechanism such as a low voltage potentiometer or any other electrical device satisfactory to allow varying the speed of an associated motor.

One embodiment of the present disclosure may provide an apparatus operable to insert an intraosseous device into a bone and associated bone marrow. The apparatus may include a housing, a drive shaft, a motor, a power supply and associated electrical circuit, and a light. The drive shaft may extend from an opening in the housing and may be operable to releasably engage the intraosseous device. The motor may be disposed within the housing and rotatably engaged with the drive shaft. The power supply and associated electrical circuit may be operable to power the motor. The light may extend from the housing and be connected to the power supply and the light may be operable to illuminate an insertion site for the intraosseous device.

Another embodiment of the present disclosure may provide a powered driver operable to insert an intraosseous device into a bone and associated bone marrow. The powered driver may include a housing, a drive shaft extending from the housing, a motor, a power supply, electrical circuits, and a switch connected to the electrical circuits. The drive shaft may be operable to releasably engage the intraosseous device. The motor may be disposed within the housing and rotatably engaged with the drive shaft. The power supply and associated electrical circuit may be operable to power the motor. The switch may be operable to activate the motor to rotate the drive shaft.

Another embodiment of the present disclosure may provide an apparatus operable to insert an intraosseous device into a bone and associated bone marrow and to assist with other medical procedures. The apparatus may include a powered driver, a drive shaft, a motor, a power supply and electrical circuits, a switch, and a suction pump. The powered driver may have a housing with one end of the drive shaft extending therefrom. The one end of the drive shaft may be operable to releasably engage the intraosseous device. The motor may be disposed within the housing and rotatably engaged with the drive shaft. The power supply and electrical circuits may be operable to power the motor. The switch may be operable to activate the motor to rotate the drill shaft. The suction pump may have a connector operable to be releasably engaged with the one end of the drive shaft whereby the powered driver may operate the pump.

The present disclosure also relates to kits, apparatus contained in such kits and associated procedures to obtain access to a patient's vascular system. For some embodiments such kits may include intravenous access devices and intraosseous access devices. Such kits may be used in both emergency situations or more routine procedures associated with treating chronic conditions. The present disclosure may provide apparatus and methods to establish vascular access during treatment of a patient at a wide variety of locations and facilities including, but not limited to, accident sites, emergency rooms, battlefields, emergency medical services (EMS) facilities, oncology treatment centers, chromic disease treatment facilities and veterinary applications.

Technical benefits of some embodiments may include providing portable kits with devices and components for rapid penetration of bone and bone marrow to provide access to a patient's vascular system.

Technical benefits of some embodiments may include devices and components for rapid penetration of bone and associated bone marrow. Such devices and components may be placed in a kit for use in accessing a patient's vascular system.

Technical benefits of some embodiments may include obtaining fast, inexpensive access to a patient's vascular system with minimal risk. Apparatus and methods incorporating teachings of the present disclosure may be used to provide IO and IV access so that drugs and/or fluids can be injected into associated bone marrow.

BRIEF DESCRIPTION OF THE DRAWINGS

A more complete and thorough understanding of the present embodiments and advantages thereof may be acquired by referring to the following description taken in conjunction with the accompanying drawings, in which like reference numbers indicate like features, and wherein:

FIGS. 3A-C illustrate a side and cross-sectional view of one embodiment of the present disclosure.

FIG. 7A illustrates one embodiment of a penetrator assembly of the present disclosure.

FIG. 7B illustrates a cross-sectional view of one embodiment of a penetrator assembly of the present disclosure.

FIG. 7C illustrates one embodiment of an inner trocar in cross section of the present disclosure.

FIG. 7D illustrates one embodiment of an outer penetrator in cross section of the present disclosure.

FIG. 12A is a schematic drawing showing one example of an electrical power circuit incorporating teachings of the present disclosure.

FIG. 12B is a schematic drawing showing an example of one component of a variable speed controller satisfactory for use with a powered driver in accordance with teachings of the present disclosure.

FIG. 12C is an isometric drawing showing an example of another component of a variable speed controller which may be used with a powered driver in accordance with teachings of the present disclosure.

FIG. 12D is a schematic drawing showing an example of an electrical power circuit having an enable switch or safety switch incorporating teachings of the present disclosure.

FIG. 13A is a schematic drawing showing a powered driver disposed in a charging cradle incorporating teachings of the present disclosure.

FIG. 13B is a schematic drawing showing an isometric view of a powered driver having a battery charge indicator incorporating teachings of the present disclosure.

FIG. 13C is a schematic drawing with portions broken away showing another example of a charge indicator for a powered driver incorporating teachings of the present disclosure.

FIG. 13D is a schematic drawing with portions broken away showing still another example of a power supply status indicator for a powered driver incorporating teachings of the present disclosure.

FIG. 18A is a schematic drawing showing one example of an intraosseous needle set which may be inserted into a patient's vascular system using a powered driver.

FIG. 18B is a schematic drawing showing an isometric view with portions broken away of a connector receptacle which may be releasably engaged with a powered driver incorporating teachings of the present disclosure.

FIG. 19A is a schematic drawing showing an isometric view of one embodiment of a hub which may be installed by a powered driver in accordance with teachings of the present disclosure.

FIG. 19B is a schematic drawing showing an isometric view of one embodiment of a connector which may be installed by a powered driver in accordance with teachings of the present disclosure.

FIG. 20 is a schematic drawing showing an isometric view with portions broken away of a pump which may be operated by a powered driver in accordance with teachings of the present disclosure.

FIG. 39 is a schematic drawing showing another example of a powered driver which may be carried in a kit incorporating teachings of the present disclosure along with a strap and supporting structure for an associated intraosseous device.

FIG. 40A is a schematic drawing showing an exploded view of a manual driver and associated intraosseous device which may be carried in a kit in accordance with teachings of the present disclosure.

DETAILED DESCRIPTION

Figure 1A:
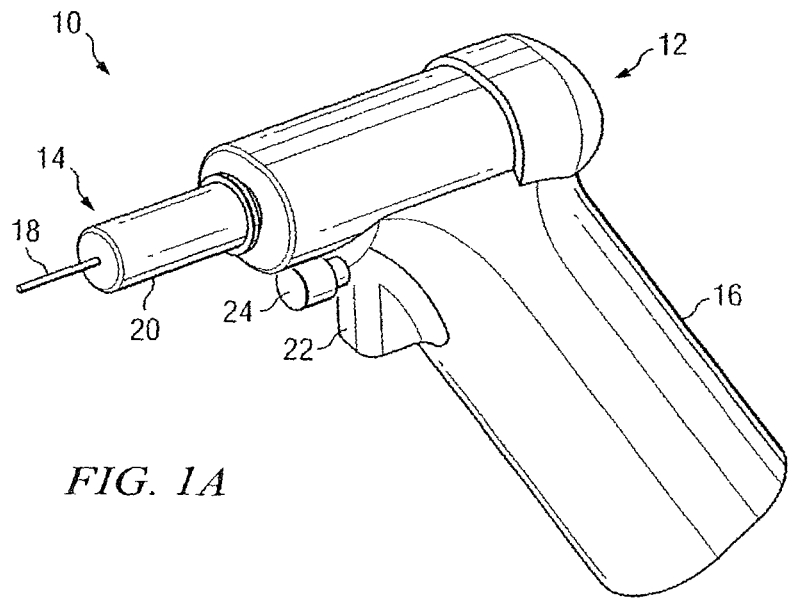
FIG. 1A is a schematic drawing showing an isometric view of one embodiment of the present disclosure.

Preferred embodiments of the invention and its advantages are best understood by reference to FIGS. 1A-41 wherein like numbers refer to same and like parts.

Apparatus and methods incorporating teachings of the present disclosure may be used to provide intraosseous access to a patient's vascular system in the sternum, the proximal humerus (the shoulder area), the proximal tibia (below the knee) and the distal tibia (above the inside of the ankle). The distal tibia may provide easier vascular access to morbidly obese patients. The distal tibia is usually a thinner area of the body. Using the distal tibia as an insertion site may allow emergency medical service personnel to pump medications and fluids into the body of obese patients when regular conventional IV access is difficult. EMS personnel may often not be able to start IVs in obese patients because their size may obscure many of the veins used for conventional IV access. Adipose tissue (fat) around normal IO access sites may be so thick that EMS personnel can't reach adjacent the bone with standard IO needles. Therefore, the distal tibia may provide an IO access site for the overweight population.

One aspect of the present disclosure may include providing a powered driver and respective IO needle sets for safe and controlled vascular access to provide medication and fluids to bone marrow, to remove biopsies of bone and/or bone marrow and to aspirate bone marrow.

Apparatus and methods incorporating teachings of the present disclosure may be used with patients of all ages and weights. For example, one IO needle set may be appropriate for patients within the weight range of 3 kilograms to 39 kilograms. A second IO needle set may be satisfactory for use with patients weighing 40 kilograms or more.

For still other applications, teeth formed on one end of a cannula or catheter may be bent radially outward to reduce the amount of time and the amount of force required to penetrate bone and associated bone marrow using the cannula or catheter. For some applications a powered driver and aspiration needle set formed in accordance with teachings of the present disclosure may provide access to a patient's bone marrow using the same amount of torque. The length of time for penetrating a relatively hard bone may be increased as compared with the length of time required to penetrate a relatively softer bone.

The circuit may limit current supplied to the motor to protect associated batteries and to protect the motor for high current flow. High current flow may correspond with high torque which indicates improper use or operation of the powered driver. High torque may also indicate that the powered driver is not driving into bone. Current flow through the motor may be directly related to torque produced by the drive shaft. For some applications the circuit may indicate when current flow through the motor is typical for penetrating the hard outer layer of a bone (compact bone issue) with an IO device. The circuit may also indicate when current flow through the motor decreases in response to the IO device penetrating associated bone marrow.

For some embodiments the powered driver may include a trigger assembly operable to activate a low speed switch, a high speed switch and/or turn an associated motor off.

For some embodiments the powered driver may include a drive shaft having one end with a generally hexagonal cross section operable to be releasably engaged with intraosseous devices including, but not limited to, biopsy needles and bone marrow aspiration needles.

For some embodiments the powered driver may include a gear assembly rotatably attached to a motor. The gear assembly may have a speed reducing ratio between 60:1 and 80:1. For some applications the gear assembly may reduce speed of rotation of an attached motor at a ratio of approximately 66:1 or 77:1.

Apparatus and methods incorporating teachings of the present disclosure may include using a first IO needle set having a fifteen (15) gage cannula with a length of approximately fifteen (15) millimeters to establish vascular access for patients weighing between approximately three (3) kilograms and thirty nine (39) kilograms. A second IO needle set having a fifteen (15) gage cannula with an approximate length of twenty-five (25) millimeters may be used to establish vascular access for patients weighing forty (40) kilograms and greater.

For some applications intraosseous needles and needle sets incorporating teachings of the present disclosure may be formed from 304-stainless steel. Standard Luer lock catheter connections may be provided on each IO needle. IO needles and needle sets incorporating teachings of the present disclosure may be easily removed from an insertion site without the use of special tooling or equipment. The reduced size and weight of drivers and IO devices incorporating teachings of the present disclosure accommodate use in emergency crash carts and emergency medical vehicles.

The term "driver" as used in this application may include any type of powered driver or manual driver satisfactory for inserting an intraosseous (IO) device including, but not limited to, a penetrator assembly, catheter, IO needle, IO needle set, biopsy needle or aspiration needle into a selected portion of a patient's vascular system. Various techniques may be satisfactorily used to releasably engage or attach an IO device and/or penetrator assembly with a driver incorporating teachings of the present disclosure. A wide variety of connectors and associated connector receptacles, fittings and/or other types of connections with various dimensions and configurations may be satisfactorily used to releasably engage an IO device with a driver. A battery powered driver incorporating teachings of the present disclosure may be used to insert an intraosseous device into a selected target area in ten seconds or less.

The term "intraosseous (IO) device" may be used in this application to include any hollow needle, hollow drive bit, penetrator assembly, bone penetrator, catheter, cannula, trocar, inner penetrator, outer penetrator, IO needle or IO needle set operable to provide access to an intraosseous space or interior portions of a bone.

For some applications an IO needle or IO needle set may include a connector with a trocar or stylet extending from a first end of the connector. A second end of the connector may be operable to be releasably engaged with a powered driver incorporating teachings of the present disclosure. An IO needle or IO needle set may also include a hub with a hollow cannula or catheter extending from a first end of the hub. A second end of the hub may include an opening sized to allow inserting the trocar through the opening and the hollow cannula. The second end of the hub may also be operable to be releasably engaged with the first end of the connector. As previously noted, the second end of the connector may be releasably engaged with a powered driver. A wide variety of connectors and hubs may be used with an IO device incorporating teaching of the present disclosure. The present disclosure is not limited to connector 1180 or hub 1200 as shown in FIGS. 18A and 18B.

Various features and benefits of the present disclosure may be described with respect to a kit having a driver to insert an intraosseous (IO) device into bone marrow of a patient at a selected insertion site. However, a kit with devices and components incorporating teachings of the present disclosure may be satisfactorily used to access various portions of a patient's vascular system. The present disclosure is not limited to IO devices and procedures.

The term "kit" may be used in this application to describe a wide variety of bags, containers, carrying cases and other portable enclosures which may be used to carry and store intraosseous devices and/or intravenous devices along with related components and accessories. Such kits and their contents along with applicable procedures may be used to provide access to a patient's vascular system in accordance with teachings of the present disclosure.

Figure 1B:
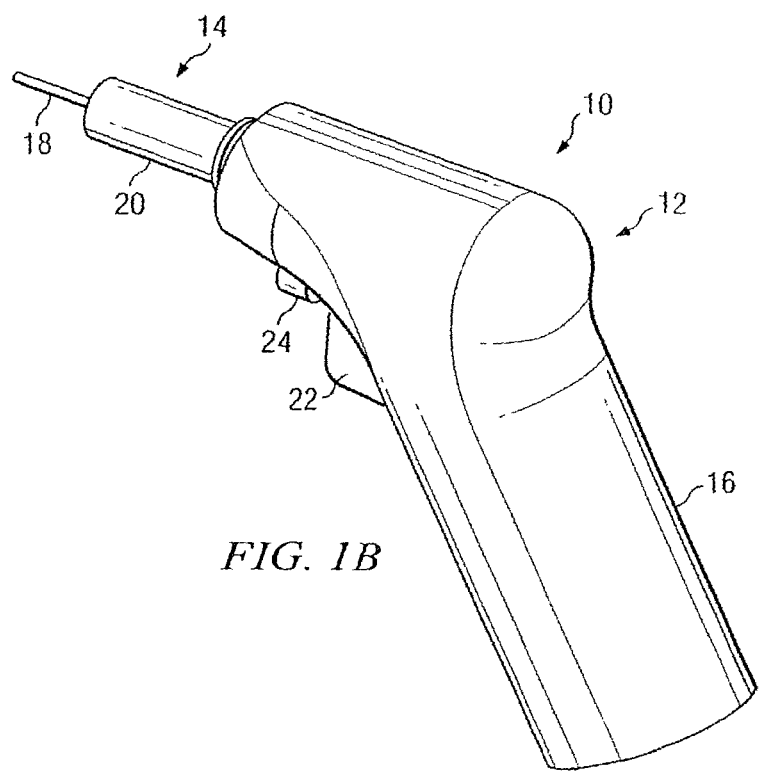
FIG. 1B is a schematic drawing showing an isometric view of one embodiment of the present disclosure.

Various examples of an apparatus operable to access the bone marrow in accordance with the present invention are shown generally in FIGS. 1A and 1B at 10. Apparatus 10 as shown in FIGS. 1A and 1B generally includes housing 12 and penetrator assembly 14. Housing 12 includes handle 16 that is sized and contoured to fit the hand of an operator. Handle 16 may include on/off switch 22 and safety 24. Penetrator assembly 14 includes outer penetrator 18, inner trocar (not expressly shown) and penetrator assembly connector 20.

Figure 2A:
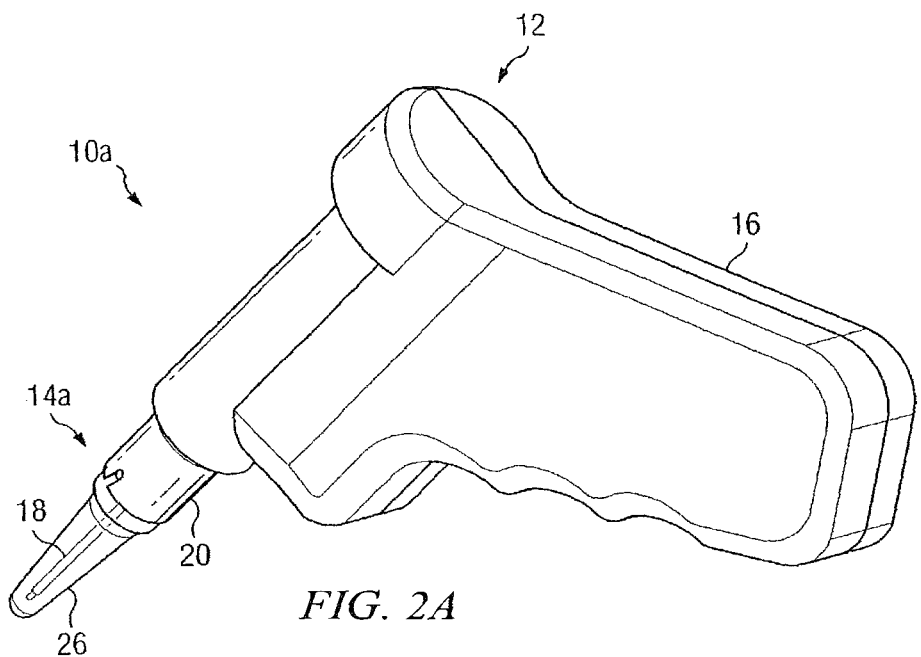
FIG. 2A is a schematic drawing showing an isometric view of one embodiment of the present disclosure.
Figure 2B:
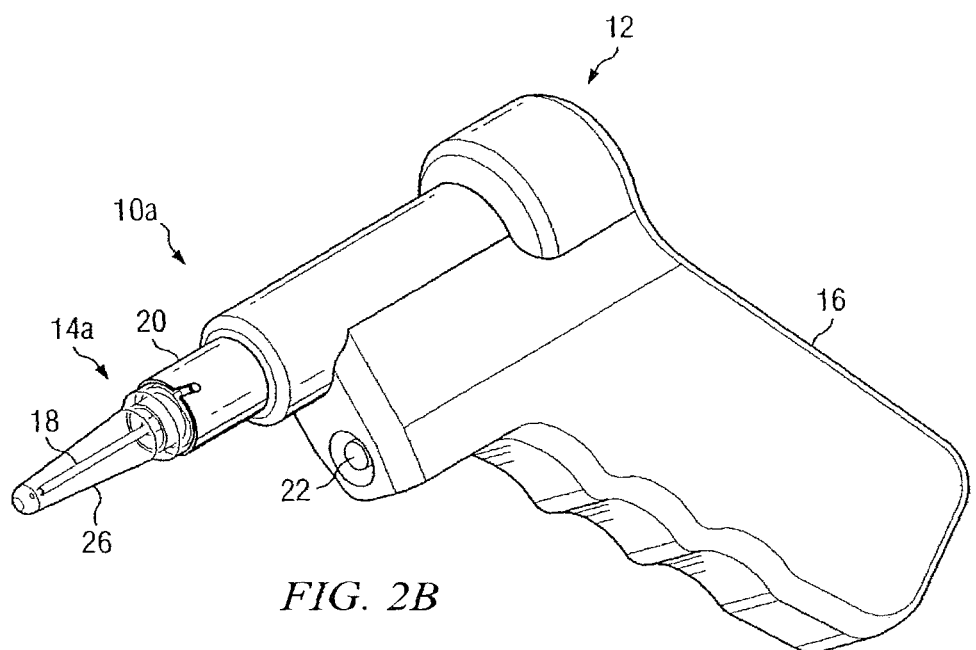
FIG. 2B is a schematic drawing showing an isometric view of one embodiment of the present disclosure.

FIGS. 2A and 2B illustrate an alternate embodiment of the present invention. Apparatus 10*a* generally includes housing 12 and penetrator assembly 14*a*. Housing 12 includes handle 16 that is sized and contoured to fit the hand of an operator. Handle 16 may include an on/off switch 22. Penetrator assembly 14*a* includes outer penetrator 18, inner trocar (not expressly shown) and penetrator assembly connector 20. Penetrator assembly 14*a* may include penetrator shield 26. An outer penetrator may include either a trocar, a needle, a cannula, a hollow tube, a drill bit or a hollow drill bit.

FIGS. 3A and 3B illustrate yet another embodiment of the present invention. Apparatus 10*b* generally includes housing 12 and a penetrator assembly (not expressly shown). Housing 12 includes handle 16 and on/off switch 22. Penetrator assembly may include penetrator (not expressly shown) and a connector, for example a pentagonal connector 20 as shown in FIG. 3A. As shown in FIG. 3B, housing 12 encloses motor 30, power supply 32, for example four or more AA batteries, motor connecting wires 34 between power supply 32 and motor 30 and switch connecting wires 36 between on/off switch 22 and power supply 32. The power supply to the apparatus may be any suitable number of AA batteries or any other type of battery, a source of direct current, a source of alternating current or a source of air or gas power. The motor may be reciprocating or rotational. Thruster bearing 45, for example a washer, may be located adjacent to housing 12 where drill shaft 40 exits housing 12. Thruster bearing 45 prevents the thrust or penetration force of drilling from being placed on gear assembly 38 as penetrator is drilled into bone. FIG. 3C shows one embodiment of the invention where drill shaft 40 may be separated into two interdigitating pieces at 42 in order to allow the two ends of drill shaft 40 to slide in and out as bone is penetrated to avoid applying excessive force to a gear assembly.

In FIG. 3B gear assembly 38 is coupled to motor 30. Gear assembly 38 may be a reduction gear assembly such as that shown in FIG. 3B that functions to reduce the revolutions per minute (RPMs) between the motor and drill shaft 40 and to increase drill shaft torque. Depending on the type of motor employed in the invention, gear assembly may or not be of the reduction type.

Figure 4A:
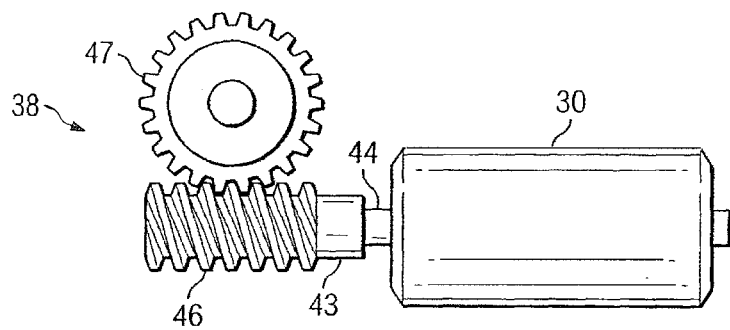
FIGS. 4A-C illustrate various alternate embodiments of a reduction gear mechanism that may be included in an embodiment of the present disclosure.

By way of example and not limitation, a reduction gear assembly, for example a worm gear assembly is shown in more detail in FIG. 4A and may include first connector 43 that connects shaft 44 of motor 30 to worm gear 46. Worm gear 46 may engage spur gear 47. Reduction gear assembly 38 may be used to decrease the RPMs between the motor and penetrator assembly to provide an optimum RPM at the point of insertion of penetrator assembly into bone. Reduction gear assembly 38 may also be used to increase the torque of drill shaft and drilling power.

Figure 4B:
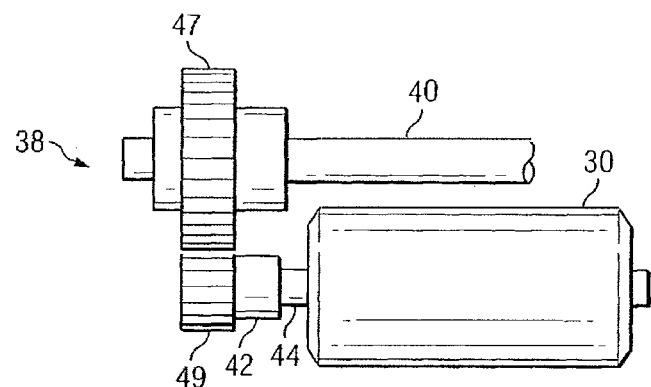
Figure 4C:
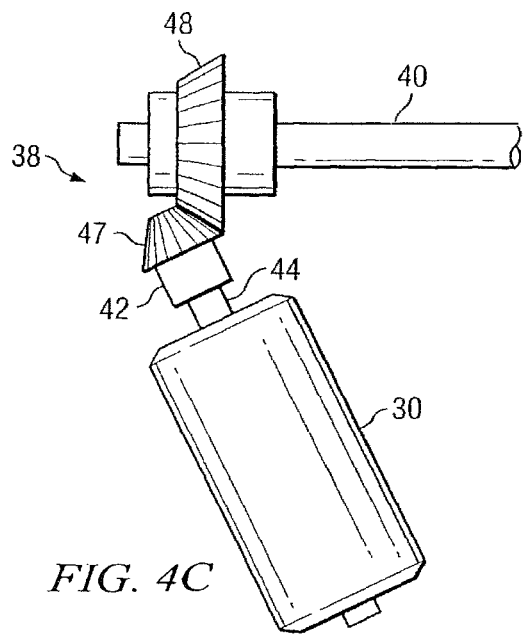

FIG. 4B illustrates one embodiment of reduction gear assembly 38 wherein a first spur gear 47 engages a second spur gear 49. FIG. 4C illustrates an alternate embodiment of reduction gear assembly 38 wherein spur gear 47 is offset from mitered gear 48 that may be preferable in some embodiments of the present invention. Other gears may be used in a reduction gear assembly, for example a planetary gear (not expressly shown) that may be used alone or in combination with a worm gear or a spur gear. In one embodiment of the current invention, gear assembly may be any suitable gear arrangement and is not limited to a reduction gear assembly.

Figure 5A:
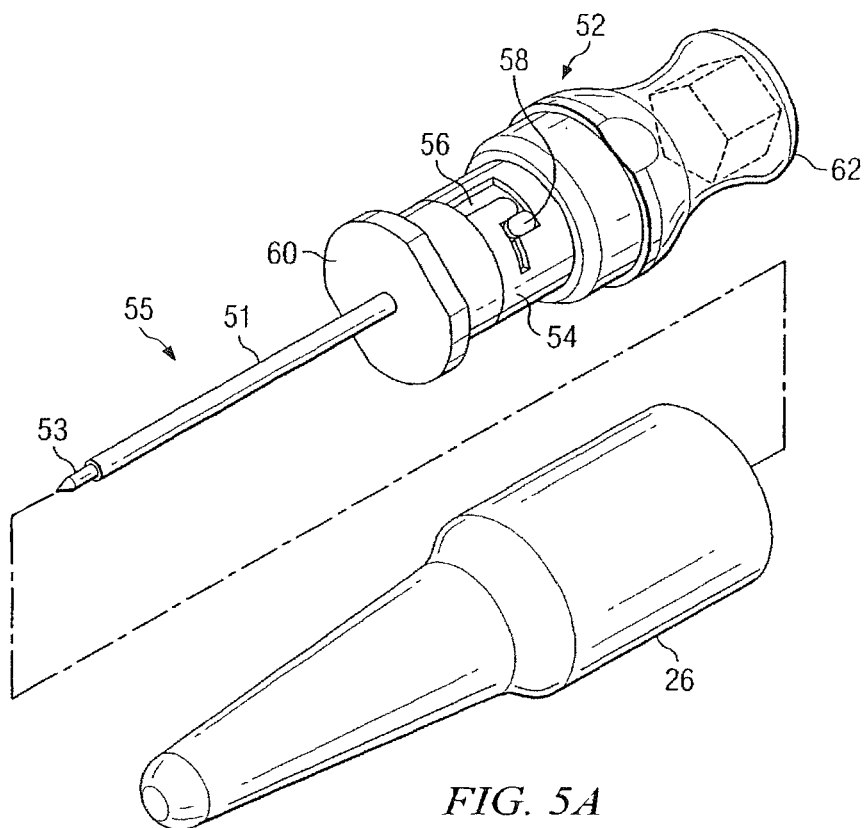
FIGS. 5A-C illustrate one embodiment of a penetrator assembly of the present disclosure.
Figure 5B:
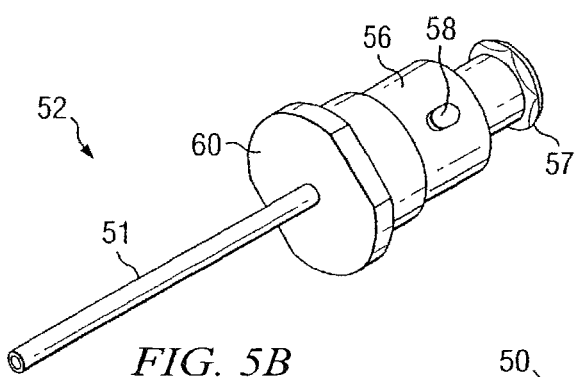
Figure 5C:
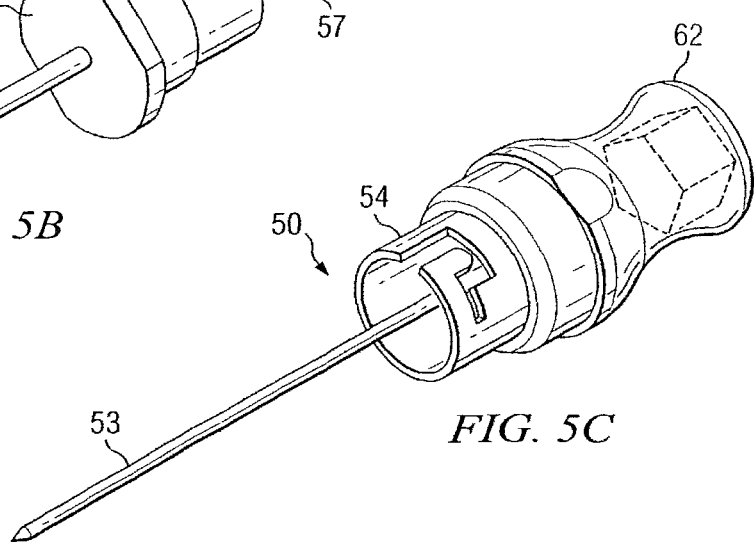

FIGS. 5A-5C illustrate one embodiment of a penetrator assembly 55 operable to penetrate a bone marrow, having a removable inner trocar 50 and an outer penetrator 52. Also shown in FIG. 5A is a penetrator shield 26 that may be used to shield penetrator assembly 55 from inadvertent engagement and also serves to preserve needle sterility. In some embodiments outer penetrator 52 may be a type of needle or cannula. FIG. 5B illustrates outer penetrator 52 may include a male connecting piece 56 operable to engage a complementary female connecting piece 54 of inner trocar 50. Adjacent to male connecting piece 56 is connecting piece locking mechanism 58 that locks into position on female connecting piece 54. Alternatively outer penetrator may include a female connecting piece suitable to engage a complementary male connecting piece of an inner trocar. Luer lock attachment 57 is coupled to male connecting piece 56 for connection to an intravenous tubing or syringe after the outer penetrator is positioned in the bone marrow. Male connecting piece 56 and female connecting piece 54 may also be of the luer-lock type. Inner trocar 50 includes stylet 53 that keeps outer penetrator 52 from getting plugged with debris created during drilling. Stylet 53 acts in combination with cannula portion 51 of outer penetrator. Outer penetrator 52 may include flange 60 that abuts or interfaces the skin of an insertion site and may be used to stabilize a penetrator assembly at the time of insertion. Penetrator assembly 55 may include various types of connectors, such as connector 62 that may be used to connect penetrator assembly 55 to a powered drill. Connector 62 may be pentagonal as shown in FIGS. 5A and 5C.

In one embodiment, the invention may include a specialized connector between the penetrator assembly and a powered drill. The connector performs at least two functions, a connecting function and a releasing function. The connecting function may be performed by various mechanisms such as a pentagonal male-female fitting or various lock-and-key mechanisms such as one that may include a combination or series of grooves and ridges or bars that match and interlock on a connector.

The releasing function may be performed by an O-ring connection, a magnetic connector, a chuck release mechanism, or a ball and detent mechanism with and without a spring. In one embodiment the releasing function may occur by means of a trigger mechanism whereby a trigger comes in contact with a holding mechanism and releases a penetrator or needle. In another embodiment a connecting mechanism may also include a trigger or retractable shield rod that slides up and contacts a holding mechanism or clamp that breaks away and releases a penetrator or needle after contact (not expressly shown).

Figure 6A:
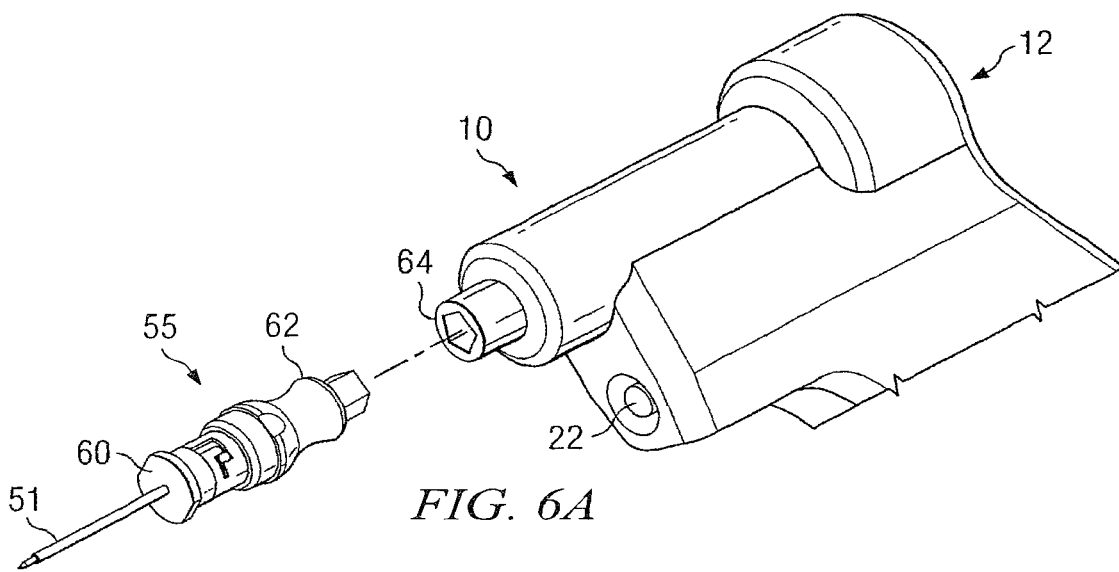
FIGS. 6A-C illustrate various alternate embodiments of a penetrator assembly connector of the present disclosure.
Figure 6B:
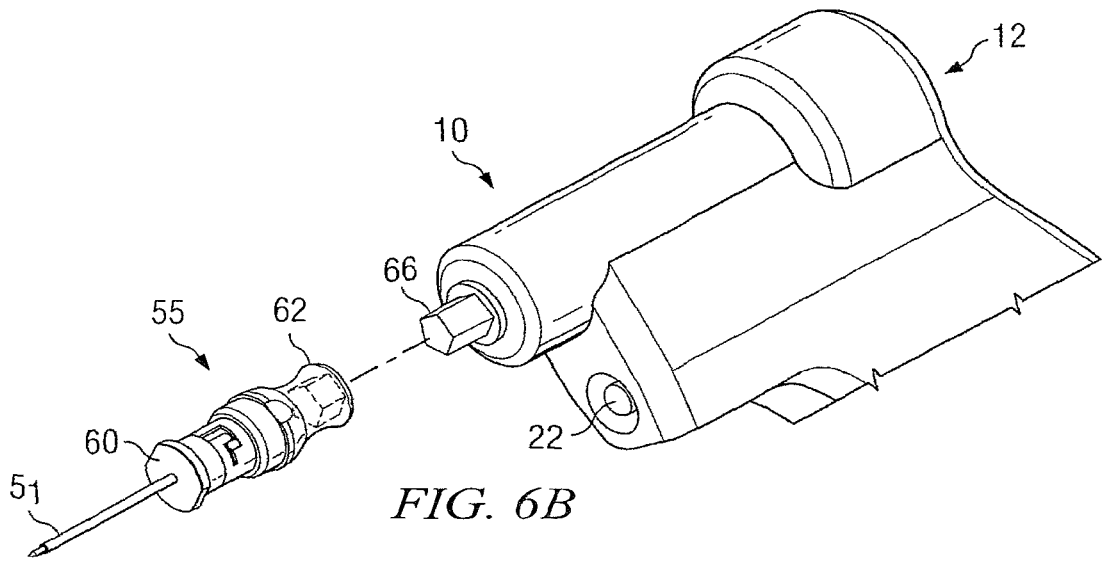
Figure 6C:
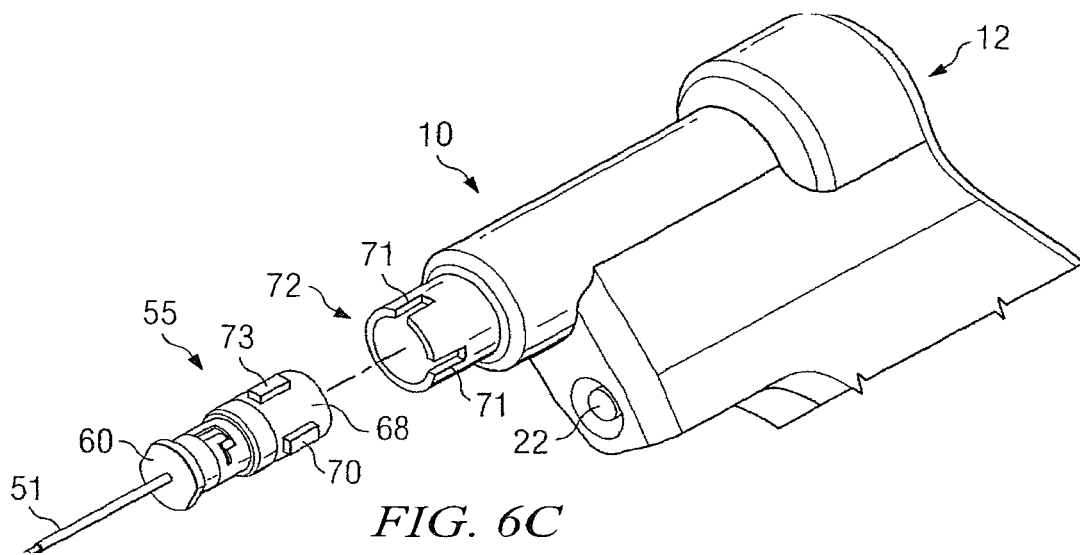

FIGS. 6A-C illustrate alternate embodiments of connectors operable to releasably attach penetrator assembly 55 to powered drill apparatus 10. FIG. 6A illustrates penetrator assembly connector 62 wherein connector 62 is formed to fit into a connector receptacle 64 and releasably lock into place. In this example, connector 62 and connector receptacle 64 are pentagonal shaped. Advantages of this embodiment may be the ease of attachment and removal of penetrator assembly 55 from powered drill apparatus 10. Penetrator assembly connector 62 may be formed from metal or plastic.

FIG. 6B illustrates an alternate embodiment of penetrator assembly connector wherein a female pentagonal receptacle 65 is operable to engage pentagonal connecting piece 66 attached to powered drill apparatus 10. FIG. 6C illustrates a further embodiment of a penetrator assembly connector wherein penetrator assembly connector 68 is a proprietary design having a pattern of ridges or bars 73 that engage a matching pattern of slots 71 on a connecting receptacle 72. Example penetrator assembly connectors may include any type of lock and key design or a pentagonal design. Penetrator assembly connectors of any type may be held in place by either a magnet, an O-ring connector or a ball and detent mechanism with or without a spring (not expressly shown).

In one embodiment, the penetrator assembly may include an outer penetrator such as a cannula, needle or hollow drill bit which may be of various sizes. Needles may be small (for pediatric patients), medium (for adults) and large (for oversized adults). Penetrator, cannulas or needles may be provided in various configurations depending on the clinical purpose for needle insertion. For example, there may be one configuration for administering drugs and fluids and an alternate configuration for sampling bone marrow or for other diagnostic purposes although one needle configuration may be suitable for both purposes. Needle configuration may vary depending on the site chosen for insertion of a needle.

FIGS. 7A-7D illustrate one embodiment of a penetrator assembly 80 that includes a removable inner trocar 82 and an outer penetrator 84. FIG. 7B illustrates a cross-sectional view of one embodiment of a penetrator assembly having a removable inner trocar 82 and an outer penetrator 84. Outer penetrator 84 includes flange 86 and flange groove 88. Flange 86 may be used to stabilize penetrator assembly 80 against the skin of an insertion site. Flange groove 88 is operable to engage plastic penetrator cover 94. The surface of outer penetrator may include a series of discs formed along a longitudinal axis, a series of ridges or some other grasping means. This surface allows an operator to grasp the outer penetrator with two fingers and easily disengage the inner trocar 82 from outer penetrator 84. Outer penetrator 84 includes a penetrator cannula 96 that is hollow when stylet 100 is removed.

In FIG. 7C inner trocar 82 includes handle 98 that may have a surface such as a series of discs formed along a longitudinal axis of the trocar, or a series of ridges or some other grasping means. Handle 98 allows an operator to easily grasp and manipulate inner trocar 82 and disengage it from outer penetrator 84. Inner trocar 82 also includes stylet 100. Stylet 100 exits an end of penetrator cannula 96 when inner trocar 82 is inserted into outer penetrator 84 Stylet 100 includes a cutting tip and is operable to penetrate bone marrow. In one embodiment of the invention, inner trocar 82 may include metal disc 95 to allow a magnetic connection between penetrator assembly and powered drill. Receptacle 97 may also engage a penetrator assembly male-type connector piece operable to connect penetrating assembly to a powered drill, or any other suitable connector.

Figure 7E:
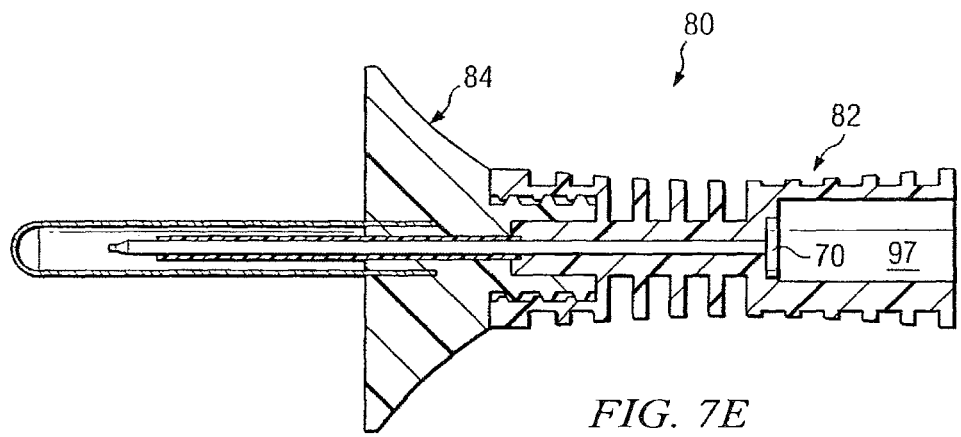
FIGS. 7E-G illustrate examples of release mechanisms of the present disclosure.
Figure 7F:
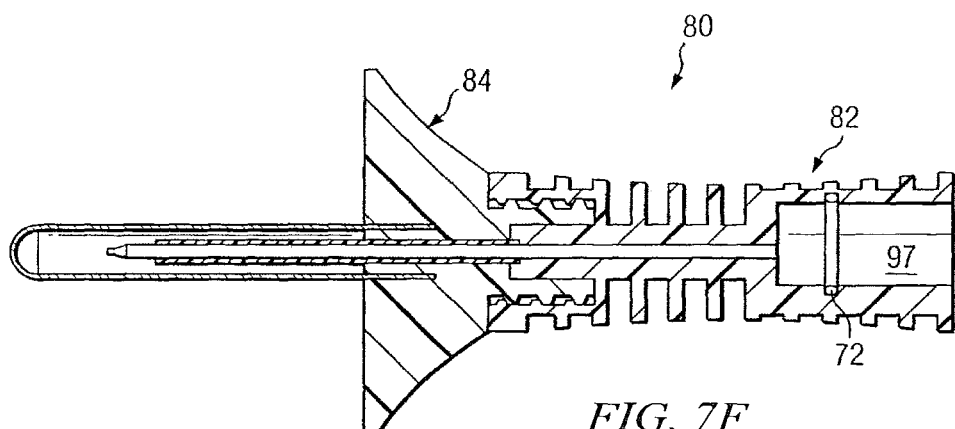
Figure 7G:
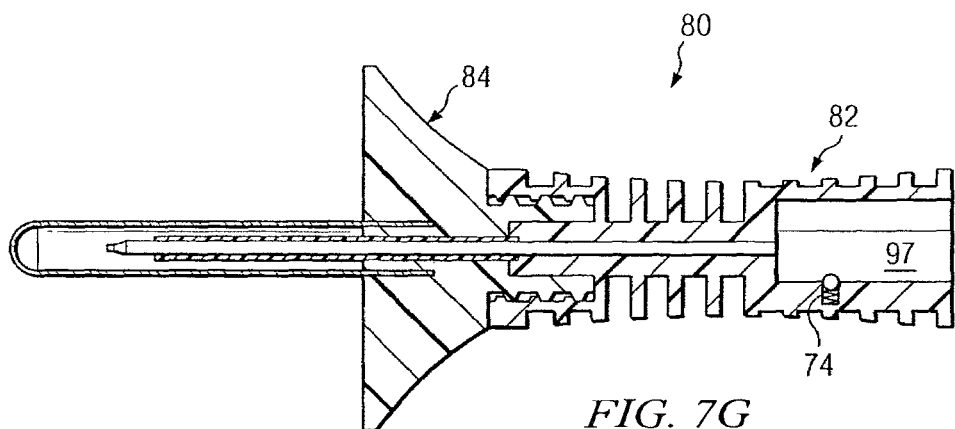

FIGS. 7E-7G illustrate example release mechanisms that may be coupled to a connector and included in penetrator assembly 80. FIG. 7E illustrates one embodiment of a magnetic release mechanism where magnetic disc 70 is included in inner trocar 82. In this embodiment magnetic disc 70 is at the base of open area or receptacle 97. In alternative embodiments a magnetic disc could be included with a pentagonal connector or a lock and key connector or any other suitable connector.

FIG. 7F illustrates another embodiment of a release mechanism where O-ring 72 is included in trocar 98 as part of a connector. In this embodiment O-ring 72 is in the wall of receptacle 97. O-ring 72 is able to engage a lock and key connector, a pentagonal connector or any other suitable connector.

FIG. 7G illustrates yet another embodiment of a release mechanism using ball and detent mechanism 74. In this embodiment ball and detent mechanism 74 is in the wall of receptacle 97. Ball and detent mechanism 74 is able to engage a lock and key connector, a pentagonal connector or any other suitable connector.

Figure 8A:
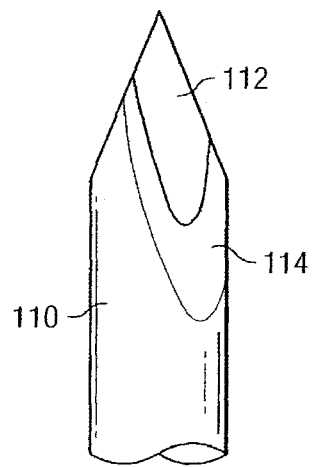
FIG. 8A illustrates one embodiment of a tip of a penetrator assembly of the present disclosure.

FIG. 8A illustrates an embodiment of an outer penetrator needle 110 and inner stylet 112. Cutting tip 114 of outer penetrator needle 110 and tip of inner stylet 112 are operable to penetrate bone marrow. In one embodiment of the invention the outer penetrator needle and the inner stylet are ground together as one unit in the manufacturing process to ensure that the two pieces are an exact fit and act as a single drilling unit.

Figure 8B:
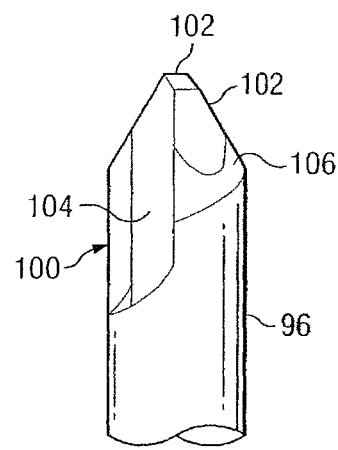
FIG. 8B illustrates one embodiment of a tip of a penetrator assembly of the present disclosure.

FIG. 8B illustrates another embodiment of an outer penetrator needle 96 and an inner stylet 100. Cutting tip 102 of inner stylet 100 is operable to penetrate bone marrow. Inner stylet may also include a longitudinal groove 104 that runs along the side of stylet 100 that allows bone chips and tissue to exit an insertion site as a penetrator assembly is drilled deeper into bone. Outer penetrator or needle 96 includes cutting tip 106 that facilitates insertion of outer penetrator or needle 96 and minimizes damage to outer penetrator or needle 96 as penetrator assembly 55 is inserted into bone marrow. In one embodiment of the invention the outer penetrator needle and the inner stylet are ground together as one unit in the manufacturing process to ensure that the two pieces are an exact fit and act as a single drilling unit.

Figure 9:
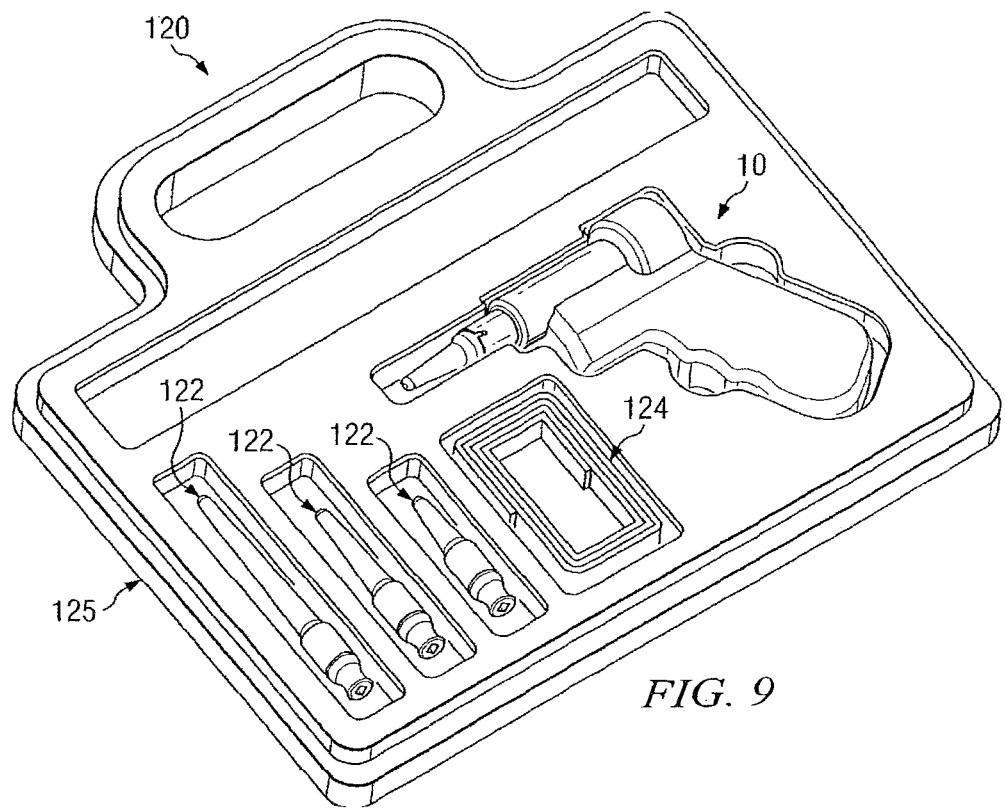
FIG. 9 illustrates one embodiment of a kit to access the bone marrow of the present disclosure.

FIG. 9 illustrates one embodiment of kit 120 to penetrate bone marrow. Kit 120 includes apparatus 10 for penetrating bone marrow, alternative sizes of penetrator assemblies 122, and strap 124 suitable to immobilize an outer penetrator on an extremity during insertion of penetrator assembly 122. Carrying case 125 is also included.

Figure 10:
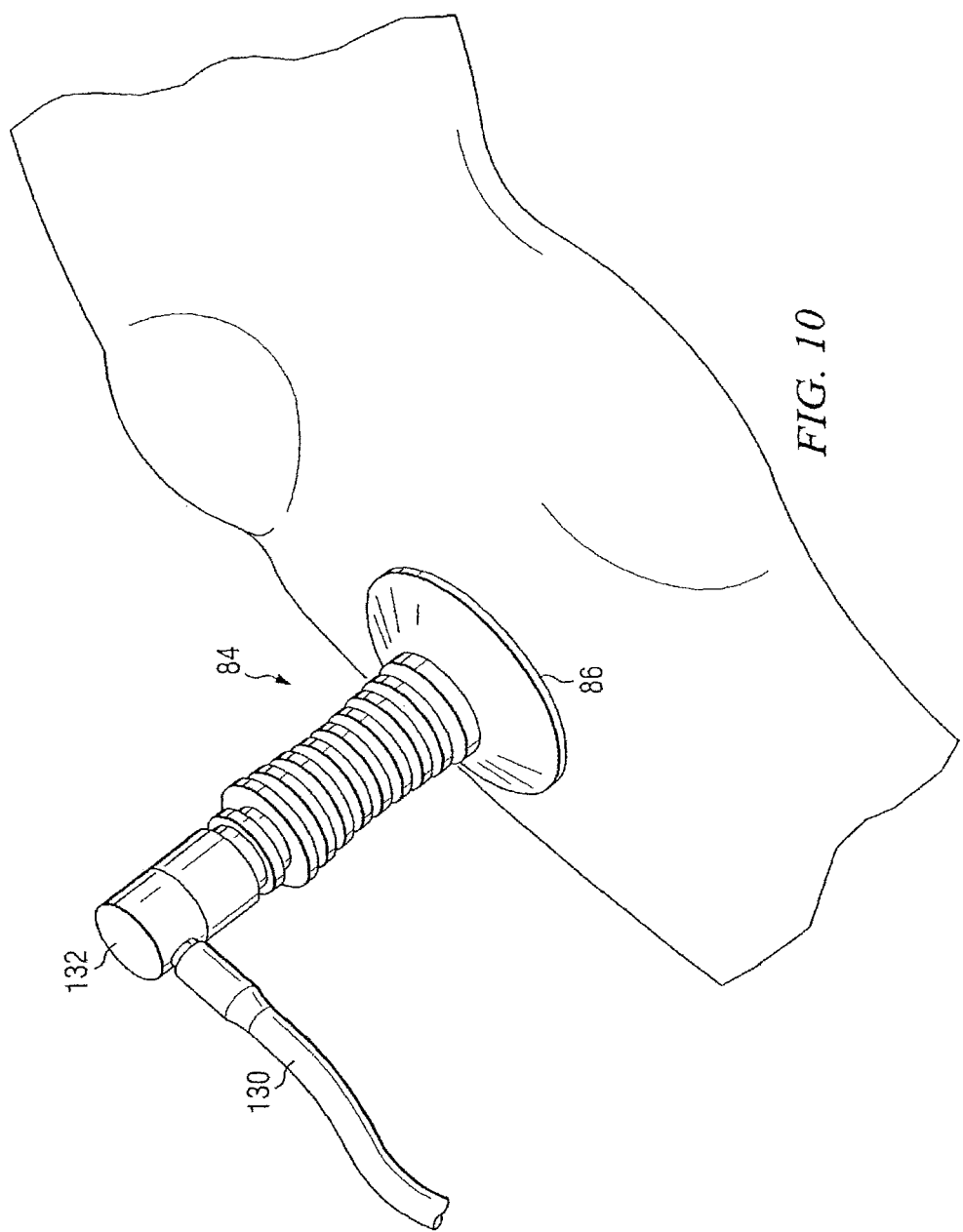
FIG. 10 illustrates one embodiment of a connector to attach to an outer penetrator of the present disclosure.

Once an outer penetrator or needle is inserted into a bone, it may be connected to a source of intravenous fluids or medication. FIG. 10 illustrates an example of a connector that may be used to connect the outer penetrator of a penetrator assembly to tubing 130, for example an intravenous tubing for providing intravenous fluids or medications to a person. Outer penetrator 84 is inserted into the bone marrow of an extremity. Right angle connector 132 is then used to connect intravenous tubing 130 to outer penetrator 84. Right angle connector has the advantage of allowing tubing to be connected to an outer penetrator or needle at an angle that will not kink or pinch off the lumen of the tubing. Other connectors or adapters may also be used to connect an outer penetrator to an intravenous tubing, another kind of tubing or to a syringe for use in providing medication or fluids to a person or for use in withdrawing a sample of blood from the bone marrow.

A method for providing access to the bone marrow includes using a powered drill, capable of reciprocal or rotational motion, to insert a penetrator assembly that includes an outer penetrator and an inner trocar into a bone marrow cavity. The powered drill is then released from the penetrator assembly and the inner trocar is grasped and removed from the outer penetrator. A connector present on the end of the outer penetrator, for example a luer lock connector, is then available for attachment to either an adapter, such as a right angle connector or directly to an intravenous tubing or syringe.

Various features of the present disclosure may also be described with respect to powered drivers 1030 and 1030a-1030f. Various features of the present disclosure may also be described with respect to intraosseous devices such as shown in FIGS. 18A and 18B. However, the present disclosure is not limited to use with intraosseous device 1160 or powered drivers 1030 and 1030a-1030f.

Figure 11A:
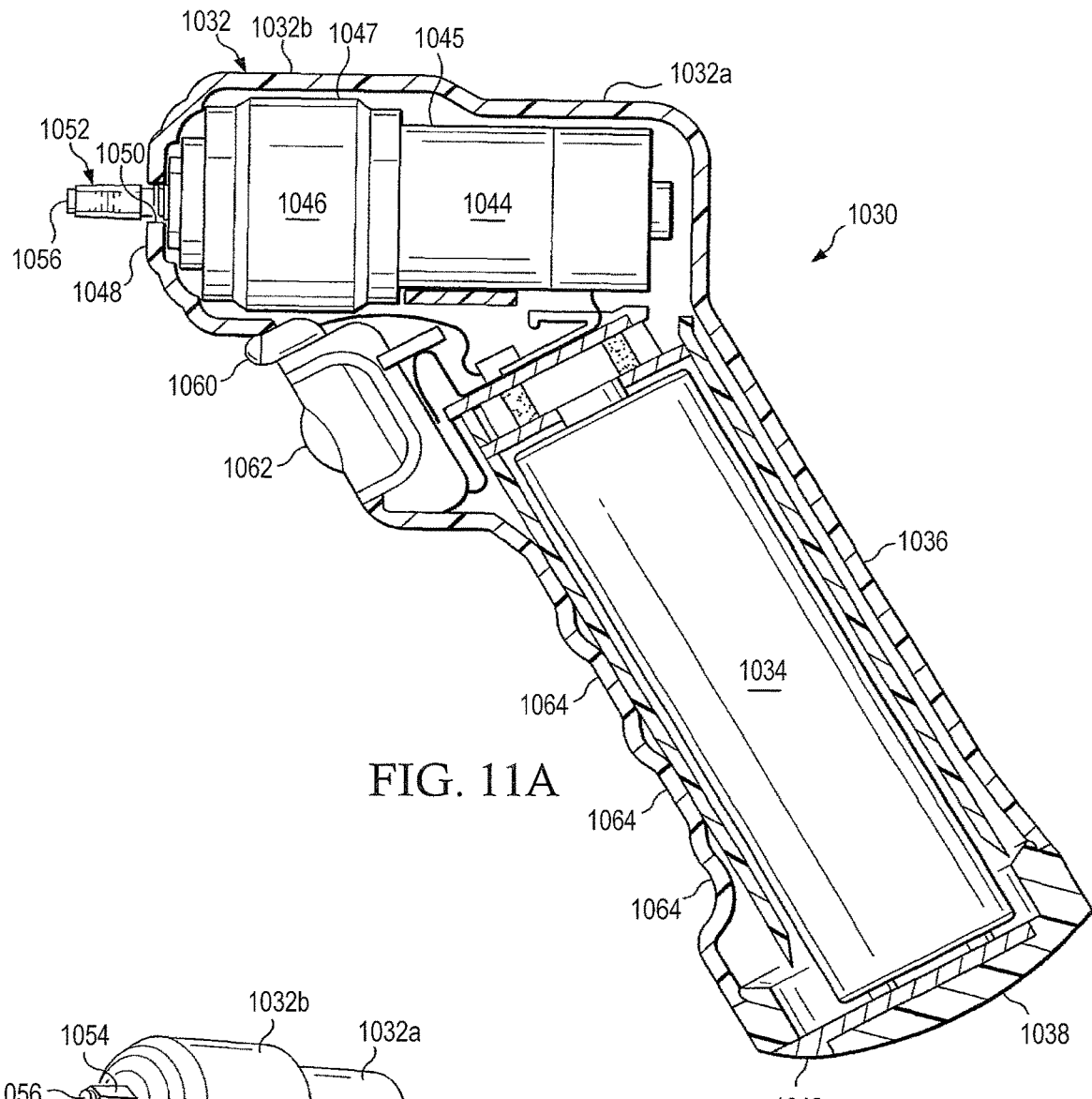
FIG. 11A is a schematic drawing in section showing one embodiment of a rechargeable powered driver incorporating teachings of the present disclosure.
Figure 11B:
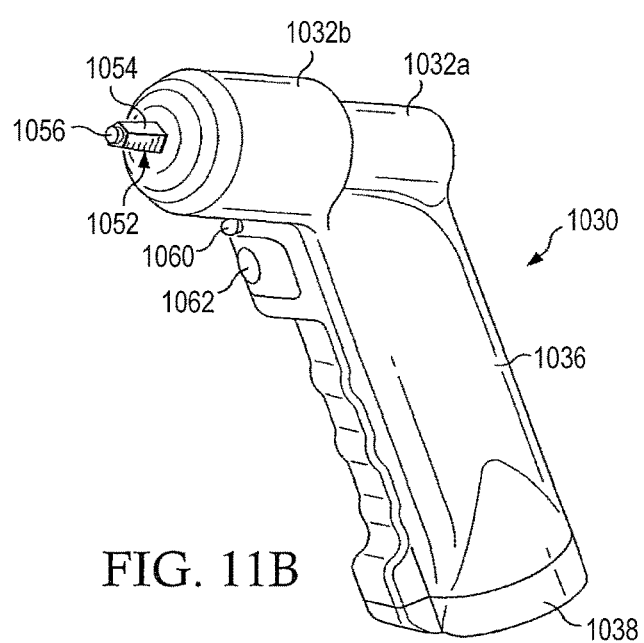
FIG. 11B is a schematic drawing showing an isometric view of the rechargeable powered driver of FIG. 11A.

Powered driver 1030 as shown in FIGS. 11A, 11B and 13A may be satisfactorily used to insert an intraosseous device at a desired insertion site adjacent to a bone and associated bone marrow (not expressly shown). For embodiments such as shown in FIGS. 11A, 11B and 13A powered driver 1030 may include one or more features of the present disclosure including, but not limited to, a light operable to illuminate an insertion site, charging contacts and associated charging circuitry, a power supply status indicator, trigger guard, variable speed controller, safety switch and/or timing circuit. At least one or more of the preceding features and/or additional features of the present disclosure may also be shown with respect to powered drivers 1030-1030f and/or 1330a-1330k.

Various components associated with powered driver 1030 may be disposed within housing 1032. For example a power source such as rechargeable battery pack 1034 may be disposed within handle 1036. Battery pack 1034 may have various configurations and may include multiple batteries disposed within sealed packaging material. For other applications, a non-rechargeable battery pack may also be disposed within handle 1036.

Handle 1036 may be generally described as an elongated, hollow container sized to receive battery pack or power supply 1034. Cap 1038 may be disposed on one end of handle 1036. Cap 1038 may be removed to allow inserting and removing battery pack 1034 therefrom. Handle 1036 may also include finger grips 1064 having generally ergonomic configurations.

For embodiments such as shown in FIGS. 11A, 11B and 13A cap 1038 may include a pair of charging contacts 1040a and 1040b. A portion of each contact 1040a and 1040b may extend from cap 1038 for engagement with an appropriate charging receptacle. See FIG. 13A. For some applications cap 1038 and adjacent portions of handle 1036 may have heavy duty screw on or thread connections (not expressly shown). For some applications cap 1038 may be formed from relatively strong, heavy duty polymeric material.

Motor 1044 and gear assembly 1046 may also be disposed within portions of housing 1032 adjacent to handle 1036. For embodiments represented by powered drivers 1030-1030e and 1330a-1330k, motor 1044 and gear assembly 1046 may be generally aligned with each other. Motor 1044 may be connected with one end of gear assembly 1046. Drive shaft 1052 may be engaged with and extend from another end of gear assembly 1046 opposite from motor 1044.

For some applications both motor 1044 and gear assembly 1046 may have generally cylindrical configurations. Exterior portion 1045 of motor 1044 may correspond with the largest nominal outside diameter associated with motor 1044. Exterior portion 1047 of gear assembly 1046 may correspond with the largest nominal outside diameter associated with gear assembly 1046. For embodiments of the present disclosure represented by powered drivers 1030-1030e and 1330a-1330k, exterior portion 1047 of gear assembly 1046 may represent a nominal outside diameter portion larger than any other outside diameter portion associated with motor 1044. In other embodiments of the present disclosure represented by powered driver 1330i, exterior portion 1047 of gear assembly 1046 may be smaller than outside diameter portions associated with impact device 1044a.

Portions of housing 1032 may have generally similar cylindrical configurations corresponding with exterior portions of motor 1044 and gear assembly 1046. For example, segment 1032a of housing 1032 may have a generally cylindrical, hollow configuration with an inside diameter compatible with exterior portion 1045 of motor 1044. Housing segment 1032b may have a generally cylindrical, hollow configuration with an inside diameter compatible with exterior portion 1047 of gear assembly 1046. Since portions of gear assembly 1046 have an outside diameter that is larger than the outside diameter of motor 1044, housing segment 1032b may have a larger outside diameter than the outside diameter of housing segment 1032a.

Motors and gear assemblies satisfactory for use with a powered driver incorporating teachings of the present disclosure may be obtained from various vendors. Such motor and gear assemblies are typically ordered as "sets" with one end of each motor securely attached to an adjacent end of an associated gear assembly. The gear assemblies may sometimes be referred to as "reduction gears" or "planetary gears".

A drive shaft having desired dimensions and configuration may extend from the gear assembly opposite from the motor. The drive shaft may be provided as part of each motor and gear assembly set. The dimensions and/or configuration of an associated housing may be modified in accordance with teachings of the present disclosure to accommodate various types of motors, gear assemblies and/or drive shafts. For example, powered drivers used with aspiration needles and/or biopsy needles may include gear assemblies with larger dimensions required to accommodate larger speed reduction ratios, for example between 60:1 and 80:1, resulting in slower drive shaft RPM. Powered drivers used to provide intraosseous access during emergency medical procedures may operate at a higher speed and may include gear assemblies having a smaller speed reduction ratio, for example between 10:1 and 30:1, resulting in higher drive shaft RPM. For some applications, the difference in size for gear assemblies may result in increasing the inside diameter of an associated housing by approximately two to three millimeters to accommodate larger gear assemblies associated with powered drivers used to insert biopsy needles and/or aspiration needles.

Distal end or first end 1048 of housing 1032 may include opening 1050 with portions of drive shaft 1052 extending therefrom. For some applications the portion of drive shaft 1052 extending from housing 1032 may have a generally pentagonal shaped cross section with tapered surfaces 1054 disposed thereon. Tapered surfaces 1054 may be disposed at an angle of approximately three (3°) degrees with respect to a longitudinal axis or rotational axis (not expressly shown) associated with drive shaft 1052. Relatively small magnet 1056 disposed on the extreme end of drive shaft 1052 opposite from housing 1032. Fittings and/or connectors with various dimensions and/or configurations other than drive shaft 1052 and/or magnet 1056 may also be satisfactorily used with a powered driver incorporating teachings of the present disclosure.

Intraosseous devices having corresponding tapered openings or connector receptacles may be releasably engaged with portions of drive shaft 1052 extending from housing 1032. For example, portions of drive shaft 1052 extending from distal end 1048 may be releasably engaged with tapered opening 1186 in connector 1180 as shown in FIGS. 18A and 18B or tapered opening 1156 in connector receptacle 1152 as shown in FIGS. 19 and 20.

For embodiments such as shown in FIGS. 11A, 11B and 13A, powered driver 1030 may also include light 1060 disposed adjacent to trigger assembly 1062. Electrical circuits and associated wiring contacts may also be disposed within housing 1032 to supply electrical power to light 1060. Trigger assembly 1062 may be used to activate electrical circuits to provide electricity from rechargeable battery 1034 to motor 1044 and/or light 1060. A block diagram showing one example of such electrical circuits is shown in FIG. 12A.

A block diagram showing one example of electrical circuits and other components which may be satisfactory used with a powered driver incorporating teachings of the present disclosure is shown in FIG. 12A. Various features of the present disclosure may be described with respect to electrical system 1400 as shown in FIG. 12A. Electrical system 1400 may include various components such as power supply or battery pack 1034, charging contacts 1040a and 1040b, motor 1044, light 1060 and/or enable switch 1062. Electrical system 1400 may include a wide variety of electrical circuits and electrical components including, but not limited to, power supply status indicator 1070 and electrical charging circuit 1410, voltage regulator 1430 and variable speed controller 1460. As previously noted, power supply or battery pack 1034 may include one or more rechargeable batteries. Various types of nickel metal hydride (NiMH) batteries may be used (particularly lithium batteries). Battery pack 1034 may supply fourteen (14) to eighteen (18) volts of direct current (DC) power. However, a wide variety of chargeable and non-rechargeable batteries may be satisfactorily used with powered drivers incorporating teachings of the present disclosure.

A wide variety of electrical circuits and/or electronic indicators may be used with power supply status indicator 1070. Additional information concerning such electrical circuits and displays may be described with respect to various power supply status indicators as shown in FIGS. 13B, 13C and 13D.

A wide variety of charging circuits, voltage regulators and variable speed controllers may be satisfactorily used with a powered driver incorporating teachings of the present disclosure. Various examples of such charging circuits, voltage regulators and/or variable speed controllers are shown in FIGS. 12B and 12C. Various types of commercial available charging circuits, voltage regulators and/or variable speed controllers may be satisfactorily used with a powered driver incorporating teachings of the present disclosure. Various examples of commercially available microcontrollers may be satisfactory for use with variable speed controller 1460. Variable resistor 1600a as shown in FIG. 12B and variable resistor 1600b as shown in FIG. 12C represents examples of mechanical devices having slidable contacts which may be used to vary current supplied to motor 1044. A trigger assembly incorporating teachings of the present disclosure may be satisfactory used to move one or more of the electrical contacts 1602*a* or 1602*b*.

Figure 15A:
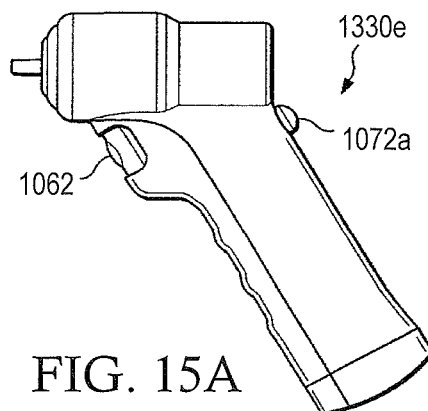
FIG. 15A is a schematic drawing showing an isometric view of a powered driver having a safety switch incorporating teachings of the present disclosure.
Figure 15B:
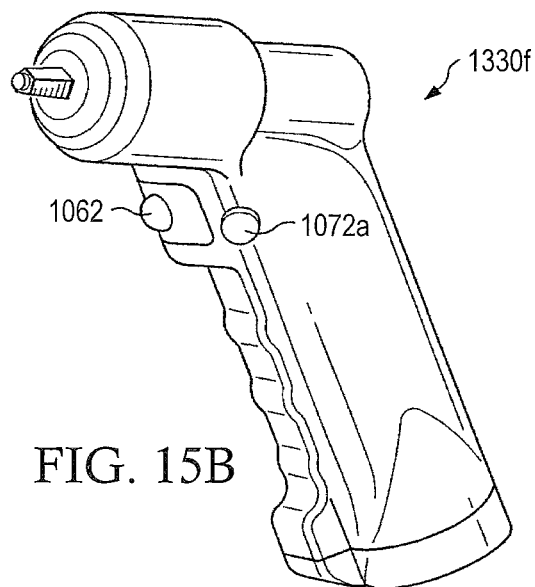
FIG. 15B is a schematic drawing showing an isometric view of another powered driver having an enable switch incorporating teachings of the present disclosure.
Figure 15C:
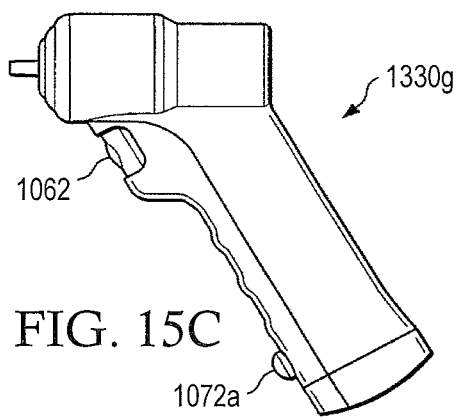
FIG. 15C is a schematic drawing showing an isometric view of still another powered driver having a safety switch incorporating teachings of the present disclosure.

Switch 1062 may be provided to prevent inadvertent or undesired activation of motor 1044. Switch 1062 may prevent discharge of battery 1034 when an associated powered device is carried in a backpack and/or mobile storage container. An associated button 1072*a* may be disposed on exterior portions of a housing to activate the variable speed controller 1460. Button 1072*a* may be located at various positions on the exterior of a housing associated with a powered driver incorporating teachings of the present disclosure as shown in FIGS. 15A-15C. A wide variety of indicators including, but not limited to, light emitting diodes (LED), liquid crystal displays (LCD) and small more conventional light bulbs may be satisfactorily used with a powered driver according to teachings of the present disclosure.

FIG. 13A shows one example of a cradle which may be used to recharge a powered driver in accordance with teachings of the present disclosure. Cradles and/or holders incorporating teachings of the present disclosure may be fabricated from a wide variety of thermoplastic and/or polymeric materials including, but not limited to, polycarbonates. Such materials may be filled with glass fibers or any other fibers satisfactory for use in forming a cradle or holder operable to hold and/or recharge a powered driver in accordance with teachings of the present disclosure. Nylon filled with glass may be used for some applications.

Materials used to form cradle 1280 may be relatively low cost but durable. Such materials may be relatively stiff to secure a powered driver therein and may also flex without breaking to allow inserting and removing a powered driver at least five hundred (500) times.

Cradle 1280 may have a length and width selected to be compatible with exterior portions of housing 1032 and corresponding dimensions of powered driver 1030. For some applications first end 1281 and second end 1282 may have generally rounded configurations. A notch (not expressly shown) may also be formed in first end 1281 to accommodate portions of drive shaft 1052. Various types of holders, clamps or quick release mechanisms may be included as part of cradle 1280. For embodiments such as shown in FIG. 13A, cradle 1280 may include a pair of arms 1284 projecting from respective edges of cradle 1280. Only one arm 1284 is shown in FIG. 13A.

Arms 1284 may be relatively strong with sufficient flexibility to allow inserting and removing portions of powered driver 1030 from engagement with cradle 1280. The height of arms 1284 relative to adjacent longitudinal edges of cradle 1280 may be based at least in part on the corresponding dimensions of handle 1036 and other portions of housing 1032. The spacing or gap formed between arms 1284 may be selected to accommodate the width of handle 1036. Respective rib 1286 may be formed on the end of each arm 1284. The configuration of ribs 1286 may be selected to be compatible with a snug but releasable snap fit with adjacent portions of handle 1036.

For some applications walls or partitions 1290 may be formed adjacent to respective arms 1294. Only one wall 1290 is shown in FIG. 13A. Partitions or walls 1290 may be spaced from each other a sufficient distance to accommodate associated portions of housing 1032 and may be sized to prevent accidental activation of trigger assembly 1062.

End 1282 of cradle 1280 may be modified to include electrical contact (not expressly shown) operable to engage recharging contacts 1040*a* and 1040*b*. Electric power cable 1292 may also extend from end 1282. Electrical power cable 1292 may be inserted into an appropriate electrical outlet for use in recharging powered driver 1030. A plurality of lights 1296, 1298 and 1300 may be provided on exterior portions of cradle 1300 to indicate the status of rechargeable battery 1034. For example light 1296 may indicate red when rechargeable battery 1034 is discharged below a desired level. Light 1298 may be flashing yellow to indicate that rechargeable battery 1034 is being recharged and/or discharged. Light 1300 may be steady green to indicate when rechargeable battery 1034 has been fully recharged. Lights 1296, 1298 and 1300 may also alternately blink or have a steady state condition.

Powered drive 1030*a* as shown in FIG. 13B may include an indicator operable to indicate the status of a power supply disposed within handle 1036. For some embodiments status indicator 1070*a* may be disposed at proximal end or second end 1049*a* of powered driver 1030*a*. A digital display indicating the number of insertions available from a power supply disposed within housing 1032*a* may be provided by indicator 1070 at proximal end 1049*a* of housing 1032*a*. The power supply may be any type of battery or other suitable source of power.

An embodiment of the present disclosure is shown in FIG. 13C which includes status indicator 1070*b* disposed on second end or proximal end 1049*b* of powered driver 1030*b*. Status indicator 1070*b* may include digital indication 1072 showing the number of insertions remaining in an associated power source. In addition variable indicator scale 1074 may be provided to show the status of an associated power source between fully charged and recharge required. For example, variable indicator scale 1074 may include a voltmeter, an amp meter, and/or any other component operable to measure the status of an associated power supply. As another example, variable indicator scale 1074 may be calibrated to display a percentage of full charge and/or a number of insertions remaining.

A further embodiment of the present disclosure is shown in FIG. 13D. For this embodiment lights 1296, 1298 and 1300 may be disposed on proximal end or second end 1049*c* of powered driver 1030*c*. Lights 1296, 1298 and 1300 may function as previously describe with respect to cradle 1280.

Figure 17A:
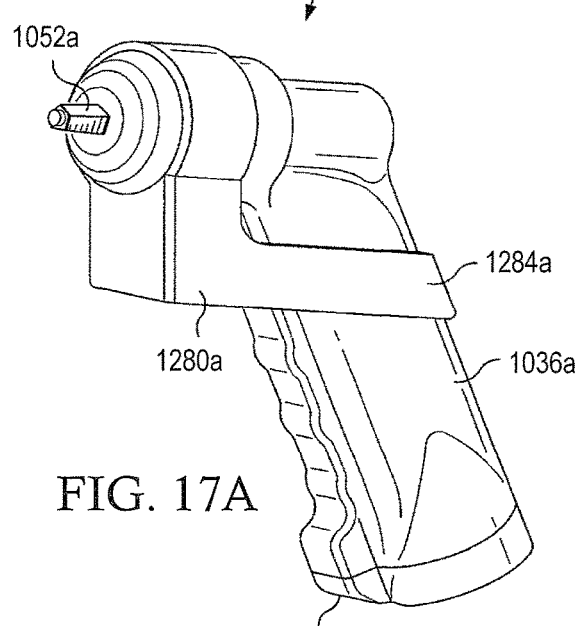
FIG. 17A is a schematic drawing showing a wall mounted cradle for a powered driver incorporating teachings of the present disclosure.
Figure 17B:
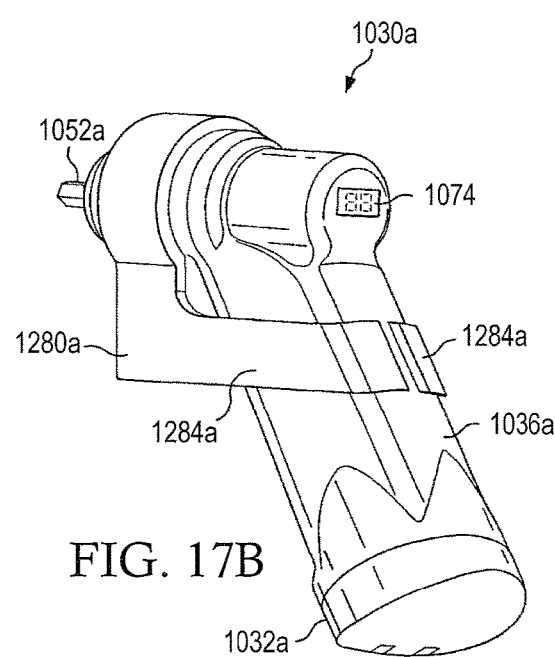
FIG. 17B is a schematic drawing showing another isometric view of a cradle and powered driver of FIG. 17B.

FIGS. 17A and 17B show another embodiment of the present disclosure including powered driver 1330*j* disposed within cradle 1280*a*. Cradle 1280*a* may include arms 1284*a* as described in relation to FIG. 13*b*. Arms 1284*a* may be relatively strong with sufficient flexibility to allow inserting and removing portions of powered driver 1330*j* from engagement with cradle 1280*a*. The height of arms 1284*a* relative to adjacent longitudinal edges of cradle 1280*a* may be based at least in part on the corresponding dimensions of handle 1336 and other portions of housing 1332. The spacing or gap formed between arms 1284 may be selected to accommodate the width of handle 1336.

Figure 14A:
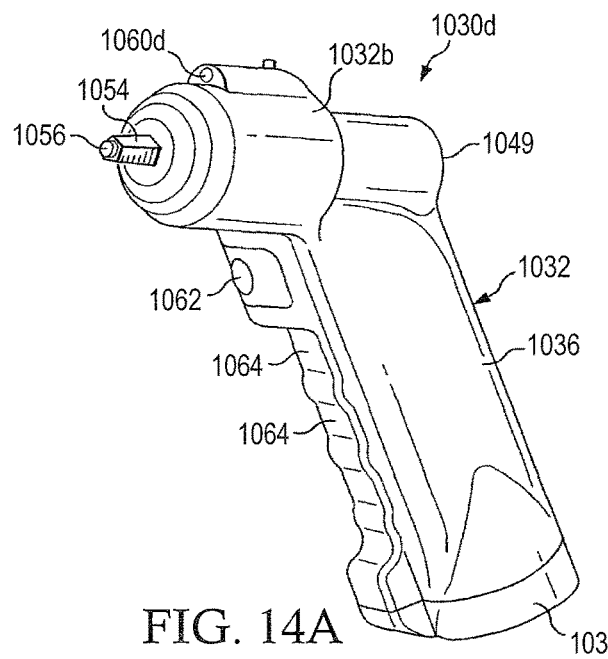
FIG. 14A is a schematic drawing showing an isometric view of a powered driver having a light in accordance with teachings of the present disclosure.
Figure 14B:
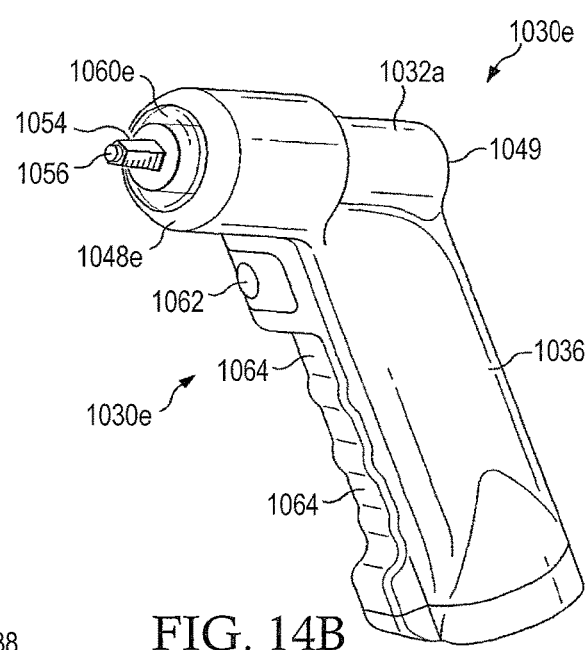
FIG. 14B is a schematic drawing showing an isometric view of another example of a light disposed on a powered driver in accordance with teachings of the present disclosure.

Powered drivers 1030*d* and 1030*e* as shown in FIGS. 14A and 14B show alternative locations for a light disposed on a powered driver in accordance with teachings of the present disclosure. Powered driver 1030*d* may include substantially the same features as powered driver 1030 except light 1060*d* may be disposed on housing segment 1032*b* opposite from trigger assembly 1062. For embodiments such as shown in FIG. 14B light 1060*e* may be disposed on distal end or first end 1048*e* of powered driver 1030*e*. Light 1060*e* may extend approximately three hundred sixty degrees (360°) around the perimeter of associated drive shaft 1054.

Figure 14C:
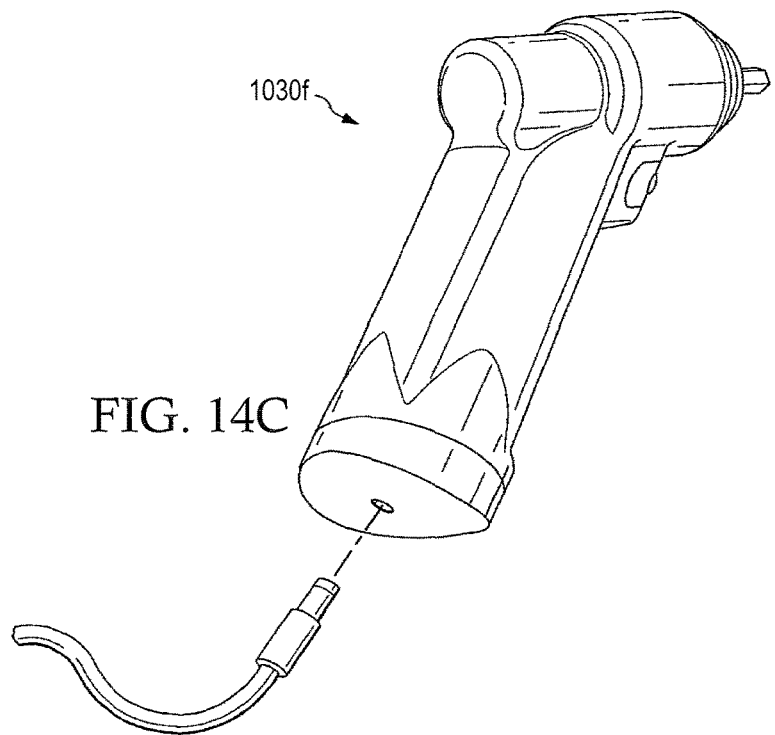
FIG. 14C is a schematic drawing showing another example of a rechargeable powered driver incorporating teachings of the present disclosure.

A further embodiment of a rechargeable powered driver incorporating teachings of the present disclosure is shown in FIG. 14C. For embodiments represented by powered driver 1030*f*, cap 1038*f* may be disposed on one end of handle 1036. Cap 1038 may include opening 1040 sized to receive charging connection 1130 attached to power cable 1132. A wide variety of recharging connectors may be used to provide power to cable 1132.

Figure 16A:
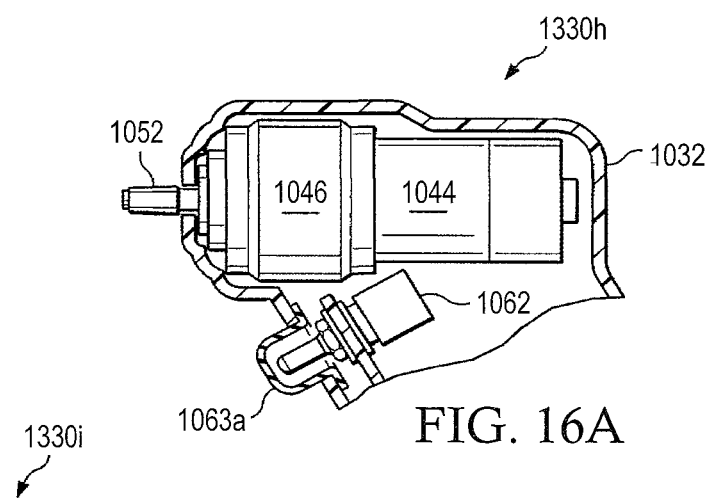
FIG. 16A is a schematic drawing in section with portions broken away showing one example of a protective covering for a trigger assembly or switch assembly of a powered driver incorporating teachings of the present disclosure.
Figure 16B:
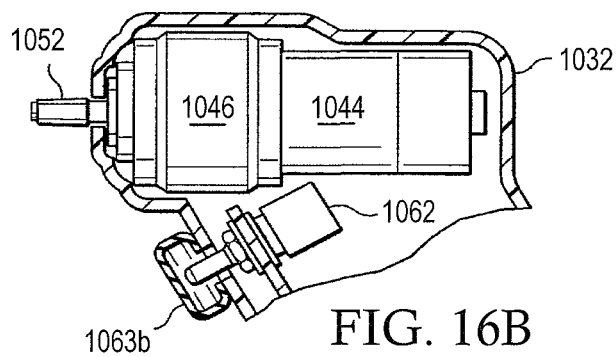
FIG. 16B is a schematic drawing showing another example of a protective cover for a trigger assembly or switch assembly of a powered driver incorporating teachings of the present disclosure.

FIGS. 16A and 16B show examples of a protective covering 1063 for trigger assembly 1062 or switch assembly 1062 of powered driver incorporating teachings of the present disclosure. Housing 1032 may be sealed to prevent blood, other bodily fluids, and/or other contaminants from reaching interior portions of housing 1032 and components disposed therein (e.g., battery 1034, motor 1044, and/or gear assembly 1046). FIGS. 16A and 16B show protective covering 1063*a* and 1063*b* configured to seal with housing 1032. Protective covering 1063*a* and 1063*b* may be formed with an elastomeric material chosen for resistance to wear, electrical current, impermeability, and/or any other characteristic sought as long as it allows operation of switch assembly 1062 by the user.

Figure 16C:
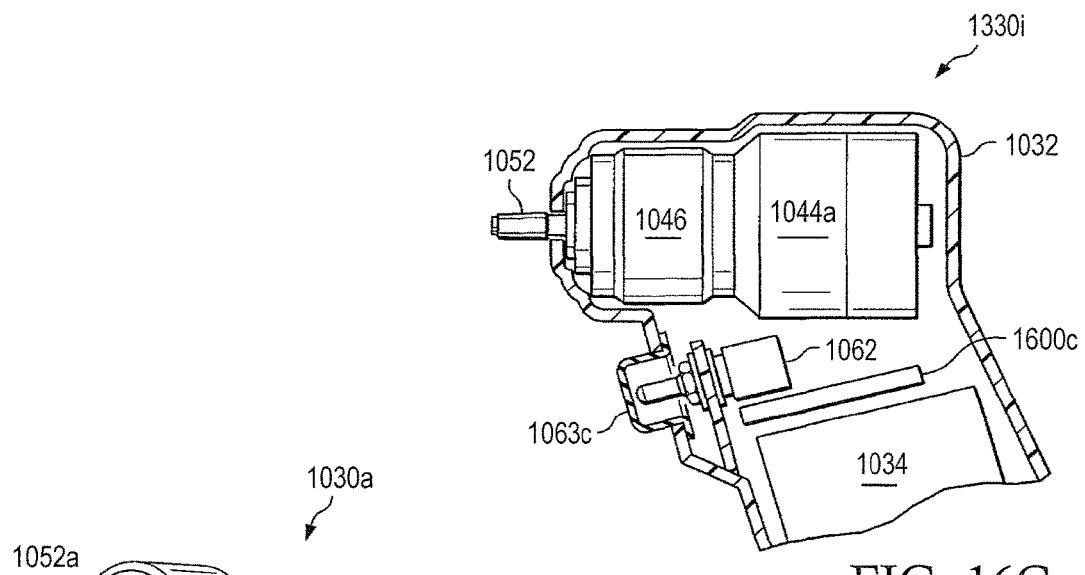
FIG. 16C is an isometric drawing showing a cross-section of a powered driver incorporating teachings of the present disclosure.

FIG. 16C shows powered driver 1330*i* incorporating an impact device 1044*a* associated with gearbox 1046 and power sensor circuit 1600*c*. Impact device 1044*a* may be configured to operate in a similar manner to an impact wrench by storing energy in a rotating mass then delivering it suddenly to gearbox 1046. In some embodiments, impact device 1044*a* will require less total power from power supply 1034.

Power sensor circuit 1600*c* may detect current changes between impact device 1044*a* and power supply 1034. In some applications, current changes between impact device 1044*a* and power supply 1034 may indicate bone penetration is complete. Power sensor circuit 1600*c* may be operable to automatically reduce or cut power from power supply 1034 to impact device 1044*a* once the associated intraosseous device has penetrated the cortex of the bone.

An intraosseous device (IO), sometimes referred to as a penetrator assembly or IO needle set, may include an outer penetrator such as a cannula, needle or hollow drive bit which may be of various sizes. Needles may be small (for pediatric patients), medium (for adults) and large (for oversized adults). Penetrator, cannulas or needles may be provided in various configurations depending on the clinical purpose for needle insertion. For example, there may be one configuration for administering drugs and fluids and an alternate configuration for sampling bone marrow or for other diagnostic purposes although one needle configuration may be suitable for both purposes. Needle configuration may vary depending on the site chosen for insertion of a needle.

A wide variety of trocars, spindles and/or shafts may be disposed within a catheter or cannula during insertion at a selected insertion site. Such trocars, spindles and shafts may also be characterized as inner penetrators. A catheter, cannula, hollow needle or hollow drive bit may sometimes be characterized as an outer penetrator.

For some applications a layer or coating (not expressly shown) of an anticoagulant such as, but not limited to, heparin may be placed on interior and/or exterior portions of a catheter or cannula to prevent thrombotic occlusion of the catheter or cannula. Anticoagulants may reduce platelet adhesion to interior surfaces of the catheter or cannula and may reduce clotting time of blood flowing into and through the catheter or cannula. Placing a layer of an anticoagulant on exterior portions of a catheter or cannula adjacent to an associated tip and/or side ports may be helpful to prevent clotting.

Penetrator assembly 1160 as shown in FIGS. 18A and 18B may include connector 1180, and associated hub 1200, outer penetrator 1210 and inner penetrator 1220. Penetrator assembly 1160 may include an outer penetrator such as a cannula, hollow tube or hollow drive bit and an inner penetrator such as a stylet or trocar. Various types of stylets and/or trocars may be disposed within an outer penetrator. For some applications outer penetrator or cannula 1210 may be described as a generally elongated tube sized to receive inner penetrator or stylet 1220 therein. Portions of inner penetrator 1220 may be disposed within longitudinal passageway 1184 extending through outer penetrator 1210. The outside diameter of inner penetrator 1220 and the inside diameter of longitudinal passageway 1184 may be selected such that inner penetrator 1220 may be slidably disposed within outer penetrator 1210.

Metallic disc 1170 may be disposed within opening 1186 for use in releasably attaching connector 1180 with magnet 1056 disposed on the end of drive shaft 1052. End 1223 of inner penetrator 1220 is preferably spaced from metallic disc 1170 with insulating or electrically nonconductive material disposed therebetween.

Tip 1211 of outer penetrator 1210 and/or tip 1222 of inner penetrator 1220 may be operable to penetrate bone and associated bone marrow. The configuration of tips 1211 and/or 1222 may be selected to penetrate a bone or other body cavities with minimal trauma. First end or tip 1222 of inner penetrator 1220 may be trapezoid shaped and may include one or more cutting surfaces. In one embodiment outer penetrator 1210 and inner penetrator 1220 may be ground together as one unit during an associated manufacturing process. Providing a matching fit allows respective tips 1211 and 1222 to act as a single driving unit which facilitates insertion and minimizes damage as portions of penetrator assembly 1160 are inserted into a bone and associated bone marrow. Outer penetrator 1210 and/or inner penetrator 1220 may be formed from stainless steel, titanium or other materials of suitable strength and durability to penetrate bone.

Hub 1200 may be used to stabilize penetrator assembly 1160 during insertion of an associated penetrator into a patient's skin, soft tissue and adjacent bone at a selected insertion site. First end 1201 of hub 1200 may be operable for releasable engagement or attachment with associated connector 1180. Second end 1202 of hub 1200 may have a size and configuration compatible with an associated insertion site for outer penetrator 1210. The combination of hub 1200 with outer penetrator 1210 may sometimes be referred to as a "penetrator set" or intraosseous needle.

Connector 1180 and attached inner penetrator 1220 may be releasably engaged with each other by Luer type fittings, threaded connections or other suitable fittings formed on first end 1201 of hub 1200. Outer penetrator 1210 extends from second end 1202 of hub 1200.

For some applications connector 1180 may be described as a generally cylindrical tube defined in part by first end 1181 and second end 1182. The exterior of connector 1180 may include an enlarged tapered portion adjacent to end 1181. A plurality of longitudinal ridges 1190 may be formed on the exterior of connector 1180 to allow an operator to grasp associated penetrator assembly 1160 during attachment with a drive shaft. See FIG. 18B. Longitudinal ridges 1190 also allow connector 1180 to be grasped for disengagement from hub 1200 when outer penetrator 1210 has been inserted into a bone and associated bone marrow.

Second end 1182 of connector 1180 may include opening 1185 sized to receive first end 1201 of hub 1200 therein.

Threads 1188 may be formed in opening 1185 adjacent to second end 1182 of connector 1180. Threaded fitting 1188 may be used in releasably attaching connector 1180 with threaded fitting 1208 adjacent to first end 1201 of hub 1200.

First end 1201 of hub 1200 may include a threaded connector 1208 or other suitable fittings formed on the exterior thereof. First end 1201 may have a generally cylindrical pin type configuration compatible with releasably engaging second end or box end 1182 of connector 1180.

For some applications end 1202 of hub 1200 may have the general configuration of a flange. Angular slot or groove 1204 sized to receive one end of protective cover or needle cap 1234 may be formed in end 1202. Slot or groove 1204 may be used to releasable engage a needle cover (not expressly shown) with penetrator assembly 1160.

For some applications a penetrator assembly may include only a single, hollow penetrator. For other applications a penetrator assembly may include an outer penetrator such as a cannula, hollow needle or hollow drive bit and an inner penetrator such as a stylet, trocar or other removable device disposed within the outer penetrator. Penetrator 1210 is one example of a single, hollow penetrator.

The size of a penetrator may vary depending upon the intended application for the associated penetrator assembly. Penetrators may be relatively small for pediatric patients, medium size for adults and large for oversize adults. By way of example, a penetrator may range in length from five (5) mm to thirty (30) mm. The diameter of a penetrator may range from eighteen (18) gauge to ten (10) gauge. The length and diameter of the penetrator used in a particular application may depend on the size of a bone to which the apparatus may be applied. Penetrators may be provided in a wide variety of configurations depending upon intended clinical purposes for insertion of the associated penetrator. For example, there may be one configuration for administering drugs and/or fluids to a patient's bone marrow and an alternative configuration for sampling bone marrow and/or blood from a patient. Other configurations may be appropriate for bone and/or tissue biopsy.

For some applications connector 1180 may be described as having a generally cylindrical configuration defined in part by first end 1181 and second end 1182. See FIG. 18B. Exterior portions of connector 1180 may include an enlarged tapered portion adjacent to end 1181. A plurality of longitudinal ridges 1190 may be formed on the exterior of connector 1180 to allow an operator to grasp associated penetrator assembly 1160 during attachment with a drive shaft. Longitudinal ridges 1190 also allow connector 1180 to be grasped for disengagement from hub 1200 when outer penetrator 1210 has been inserted into a bone and associated bone marrow.

First end 1181 of connector of 1180 may include opening 1186 sized to receive portions drive shaft 1052 therein. A plurality of webs 1136 may extend radially outward from connector receptacle 1186. Webs 1136 cooperate with each other to form a plurality of openings 1138 adjacent to first end 1181. Opening 1186 and openings 1138 cooperate with each other to form portions of a connector receptacle operable to receive respective portions of connector 1030 therein. FIGS. 19A and 19B show isometric views of embodiments of connector 1180a and hub 1200a.

A wide variety of accessory tools and devices are frequently carried by emergency medical service personnel and/or first responders. Pump assembly 1130 as shown in FIG. 20 represents an example of an accessory tool which may be operated by a powered driver incorporating teachings of the present disclosure. Pump assembly 1130 may include housing 1134 with connector receptacle 1152 extending therefrom. Various components of pump assembly 1130 (not expressly shown) may be disposed within housing 1134 and rotatably attached with connector receptacle 1152. Inlet tubing 1131 may be provided to communicate fluids with interior portions of pump housing 1134. Outlet tubing 1132 may be provided to direct fluids exiting from pump assembly 1130. Such fluids may be various types of liquids associated with medical procedures. Such fluids may include small particulate matter. Pump assembly 1130 may sometimes function as a vacuum or suction pump for such procedures.

First end 1154 of connector receptacle 1152 may include opening 1156 similar to opening 1186 as described with respect to connector 1180. End 1252 extending from power driver 1230a may be disposed within opening 1156 to rotate connector receptacle 1152 and attached components of pump assembly 1130a. As a result, powered driver 1230a may be used to pump fluids from inlet 1131 through pump assembly 1130a and outwardly from outlet 1132.

One embodiment of the device calls for it being disposable. Another embodiment is designed for the body (driver) to be reusable and the needle to be disposable. This is made possible by providing a chuck that mates with a proprietary shaft attached to the needle's Luer lock. The needles must maintain sterility during storage and mounting of the needle while the driver does not have to be sterile. The driver will be rugged in design and the battery (or other power source) will be rechargeable or the battery will be easy to replace with off-the-shelf batteries.

Figures 21, 22:
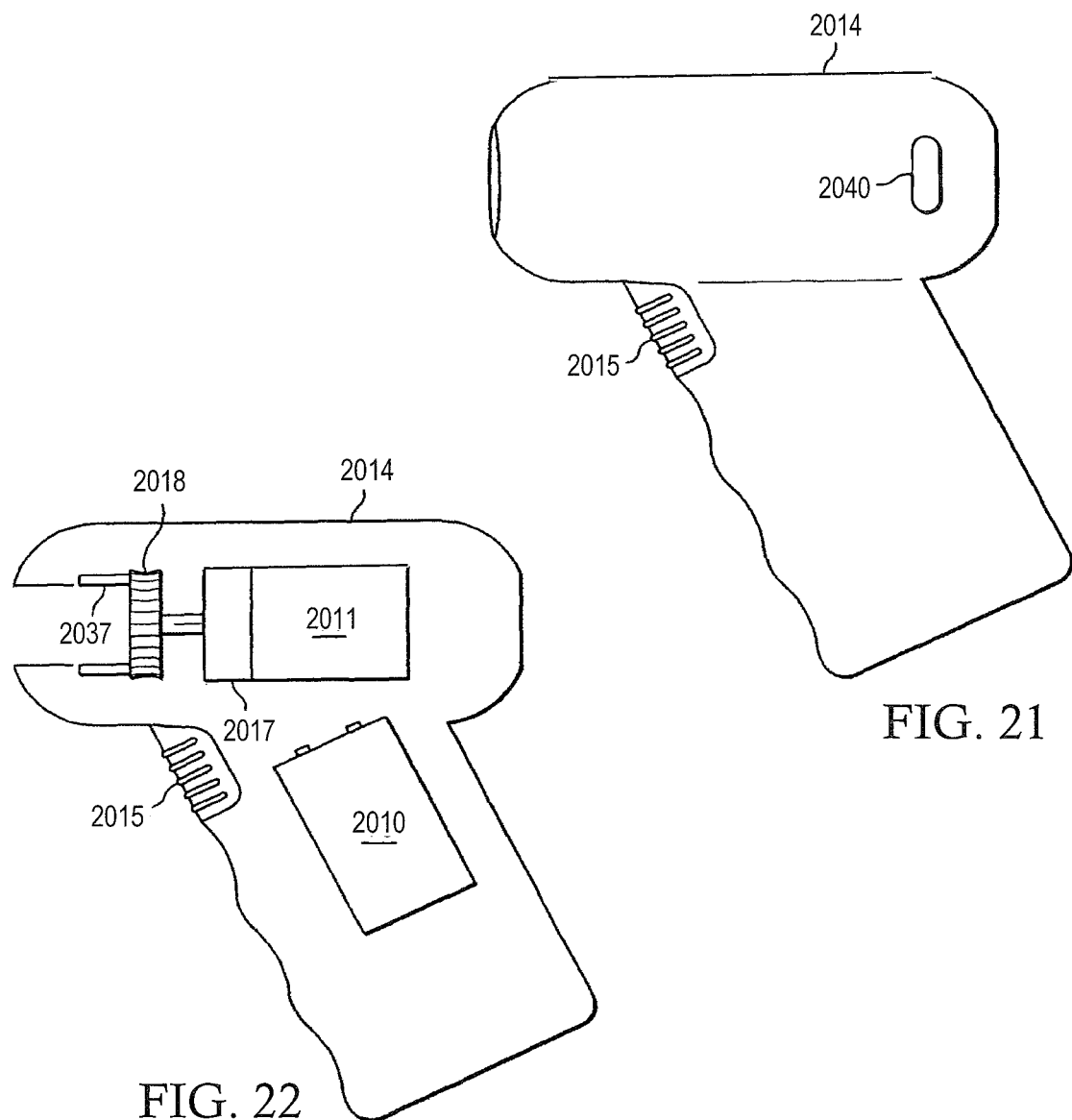
FIG. 21 illustrates a powered driver including a battery indicator according to another aspect of the present disclosure.
FIG. 22 illustrates a powered driver including a rechargeable battery according to another aspect of the present disclosure.

FIG. 21 shows the configuration of a driver without a needle inserted. A housing 2014 and a trigger 2015 are shown. A battery indicator 2040 is also shown.

FIG. 22 shows the motor 2011, gearbox 2017, gear 2018, and battery 2010 of the reusable driver. It also shows the chuck 2037, which is designed to accept the keyed needle or "unit dose" ampule. It is important in the reusable design to have a rechargeable battery or the ability to easily change off-the-shelf batteries i.e. a 9-volt battery. It may also incorporate a battery level indicator or other battery reserve indicator (not expressly shown).

The present disclosure includes a wide variety of kits, devices and associated components which may be used to obtain vascular access to a patient. In some embodiments, such kits may include apparatus operable to access a patient's bone marrow using a driver, an intraosseous needle and one or more connectors to communicate fluids with the patient's bone marrow. Such kits may also include apparatus which allows monitoring a patient.

Kits incorporating teachings of the present disclosure may be rigid, semi-rigid or soft-sided. Such kits may provide a convenient way to carry various components and devices operable to achieve vascular access in an organized and systematic fashion. Such kits may present EMS first responders and other medical personnel with a well organized collection of components and devices to achieve vascular access by placement of peripheral intravenous (IV) catheters and/or intraosseous (IO) catheters. For some embodiments, a kit incorporating teachings of the present disclosure may be combination an IV kit, an IO kit and/or a unit dose kit in one convenient bag. Examples of various types of devices and components which may be carried in a kit in accordance with teachings of the present disclosure are shown in FIGS. 29A-41.

Securing devices incorporating teachings of the present disclosure may be provided in kits to allow easy removal and replacement of associated drivers. Such securing devices may include a wide variety of cradles and other types of holder's with relatively rugged snap-in features to prevent undesired release of a driver from an associated securing device. Securing devices may be formed from plastic and/or glass composite materials to provide durability for repeated replacement and use of an associated driver. Such securing devices may releasably hold an associated driver in place within a kit so that the driver does not interfere with other devices and components disposed in the kit. A securing device may be positioned in a kit to clearly present an associated driver to a user during consideration of alternate vascular access routes.

Securing devices incorporating teachings of the present disclosure may make it easy for a user to extract an associated driver from a kit using only one hand. Other components such as penetrator assemblies and IO needles may be conveniently located in the kit to further minimize time and manipulations required for a user to attach an IO needle and insert the IO needle at a desired site in a patient. Such securing devices may also provide an easy site to return the driver to the kit after use. The associated driver may snap into place to securely protect the driver against accidental deployment until required for use in presiding another IO access.

Kits incorporating teachings of the present disclosure may be used in locations where ruggedness and durability are of paramount importance. Such kits may be washable, water proof, temperature resistant, and/or crush proof. Such kits may have a wide variety of different shapes and colors. Kits incorporating teachings of the present disclosure may be any size as required to contain selected IO devices and IV devices which may be used to obtain vascular access. In some embodiment kits may be approximately ten inches in length by six to eight inches in width.

For some applications kits incorporating teachings of the present disclosure may be designed for use in military applications. Such kit may be as compact as feasible with components disposed in one or more compartments as necessary for an efficient use of space. Such kits may also include a manual intraosseous driver and related intraosseous components to access a patient's vascular system. Such kits may include intraosseous catheters, intravenous catheters, containers with sterile normal saline, tourniquets and IO/IV securing devices. Various components may be configured for particular branches of the military, e.g., Army, Navy, Air Force, Coast Guard and Special Forces.

Another benefit of the present disclosure may include forming a kit with one or more dividers having components and devices arranged in order on page one and page two corresponding with steps of a procedure such as treating a patient with an emergency condition or treating a patient for a chronic condition. The pages in a kit may be arranged to accommodate a wide variety of procedures. For example, if a kit will be used in an oncology related application or for treatment of other chronic conditions, the "pages" in the kit may be arranged based on the steps required to provide access to a patient's vascular system and to carry out a planned treatment.

Various techniques and procedures may be used to position and securely engage a supporting structure for an IO device at an insertion site. For some applications, various types of straps may be used. See FIGS. 30 and 33-39. Alternatively, various types of medical grade tape and adhesive materials (not expressly shown) may be used. Also, Velcro strips may be used (see FIGS. 37 and 38).

Figure 28:
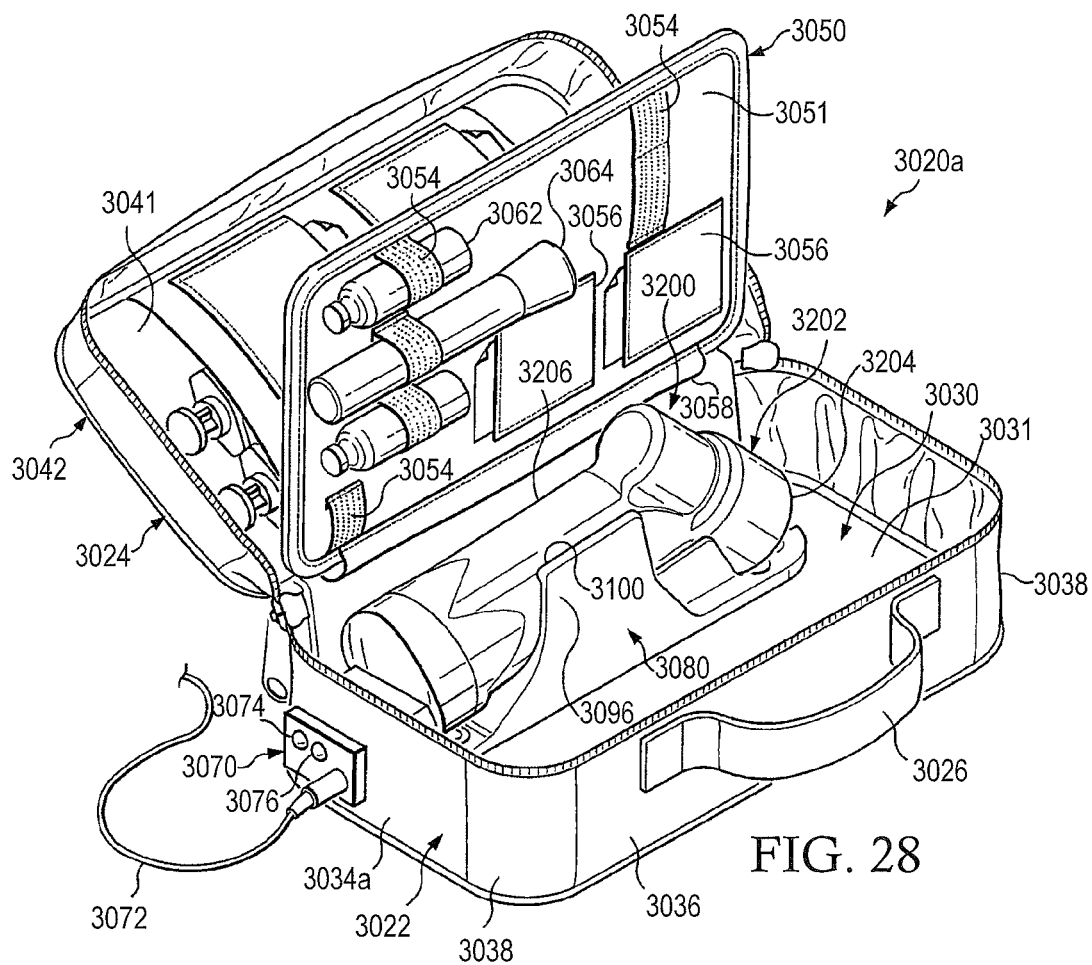
FIG. 28 is a schematic drawing showing an isometric view of one example of a kit in a second, open position with a powered driver installed in a securing device operable to recharge a battery carried within the powered driver in accordance with teachings of the present disclosure.
Figure 29A:
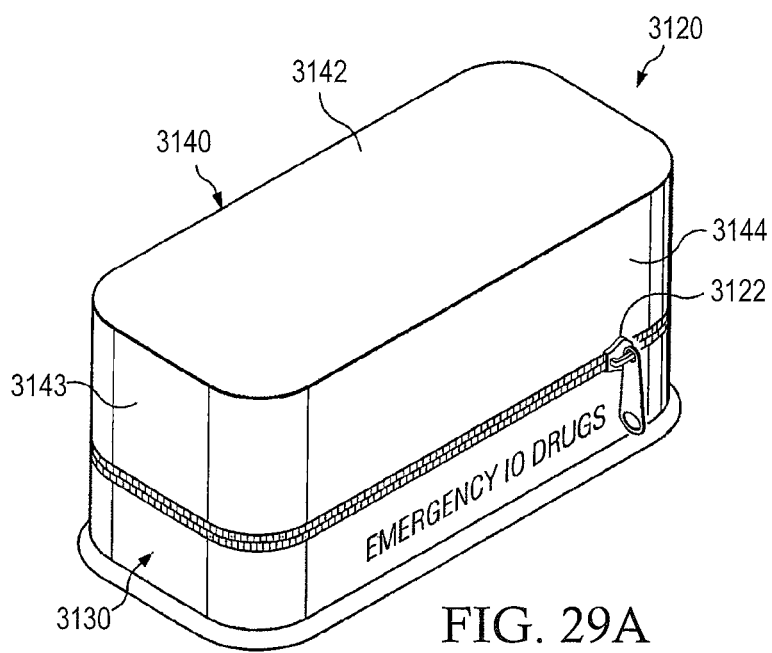
FIG. 29A is a schematic drawing showing another example of a kit in a first, closed position incorporating teachings of the present disclosure.
Figure 29B:
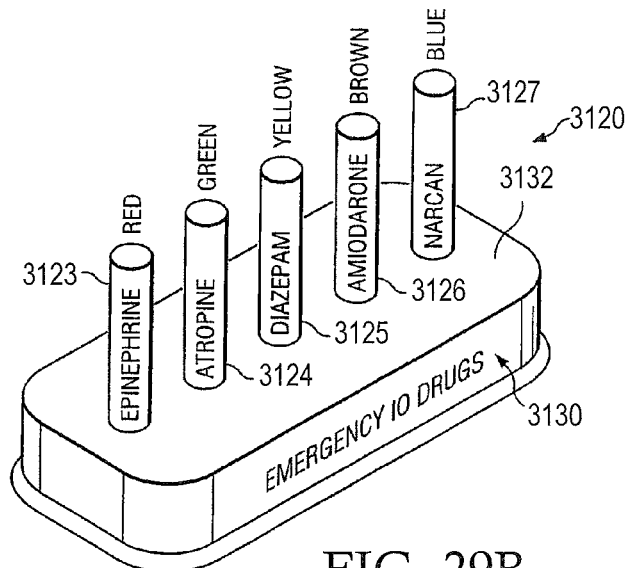
FIG. 29B is a schematic drawing showing an isometric view of the kit of FIG. 29A in a second, open position.

Some features and benefits of the present disclosure may be described with respect to kit 3020 (See FIGS. 23A, 23B, 24A) and kit 3020a (See FIG. 28) and kit 3120 (See FIGS. 29A and 29B). However, the present disclosure is not limited to kits with designs, features and/or contents as shown in FIGS. 23A-41.

For some applications kits 3020, 3020a and/or 3120 may be semi-rigid or soft, sided. Kits 3020, 3020a and 3120 may be formed from a wide variety of materials including, but not limited to, nylon, corduroy type materials, various types of polymeric and plastic materials. For some applications kits 3020, 3020a and/or 3120 may be formed from relatively soft materials such as canvas, polyesters and similar materials. For other applications kits incorporating teachings of the present disclosure may be relatively rigid and formed from materials such as lightweight aluminum alloys and similar hard materials.

For embodiments such as shown in FIGS. 23A-24A and 28, kits 3020 and 3020a may be formed using compression molded techniques. For other applications, kits 3020 and 3020a may be formed with a foam liner having desired configuration and dimensions with an outer layer of sewn fabric. Such foam liners may be designed to protect the contents carried in the resulting kit from being damaged or crushed. Other alternative low-cost, and reliable manufacturing techniques may be satisfactorily used to form kits in accordance with teachings of the present disclosure.

For some applications, kits 3020 or 3020a may be generally described as a two part molded case formed at least in part by compression molding ethylene vinyl acetate (EVA) foam. EVA may be generally described as a polymeric material with some of the characteristics of elastomeric materials and some characteristics of thermal plastic materials. However kits incorporating teachings of the present disclosure may be formed from a wide variety of polymeric materials, elastomeric materials and/or thermoplastic materials.

Kits 3020 and/or 3020a may have a nominal wall thickness of approximately 0.19 inches. Exterior surfaces of kits 3020 and/or 3020a may be covered by a durable layer of heavy linear polyester or other suitable material. Interior portions of kits 3020 and/or 3020a may be formed in part by relatively smooth layers of urethane or relatively smooth layers of polyvinyl chloride (PVC). Such materials allow interior portions of kits 3020 and/or 3020a to be more easily cleaned, particularly after use during an emergency at a field location.

Kits 3020 and/or 3020a may have two segments or enclosures 3022 and 3024 with generally hollow, rectangular configurations and compatible dimensions. As a result first segment 3022 and second segment 3024 may be releasably engaged with each other to form an enclosure having desired dimensions and configurations to efficiently carry IO and IV devices and components associated with kits 3020 and 3020a. For some applications, first segment 3022 and second segment 3024 may have approximately the same dimensions and configurations such that each segment 3022 and 3024 may form approximately one-half of the resulting kit. For applications such as shown in FIGS. 23A-24A and 28, first segment 3022 may have a greater height or depth as compared with second segment 3024. Interior portions of first segment 3022 may be sized to contain intravenous fluid bags, intravenous tubing and extension tubing, various types of connectors, syringes and Lidocaine or other anesthetizing agents.

For purposes of describing various features of the present disclosure, first segment 3022 may be described as having generally rectangular bottom layer or base 3030 with respective pairs of walls 3034 and 3036 extending therefrom. Base 3030 may also include first surface or interior surface 3031 (See FIGS. 24A and 28) and a second, exterior surface (not expressly shown). One wall 3034a of kit 3020a may be modified as compared to corresponding wall 3034 of kit 3020. Wall 3034a will be discussed later in more detail. Generally rounded corners 3038 may be formed between adjacent walls 3034 and 3036.

Second segment 3024 may be defined in part by top layer or cover 3040. Sometimes top layer 3040 may also be referred to as a lid. Top layer 3040 may include first surface or interior surface 3041 (See FIGS. 24A and 28) and second surface or exterior surface 3042 (See FIG. 23A). Respective pairs of walls 3044 and 3046 may extend from top layer 3040. Respective rounded corners 48 may be formed between adjacent walls 3044 and 3046.

For some applications, a pair of zippers 3028 and 3029 may be used to releasably engage second segment 3024 with first segment 3022 when associated kits 3020 or 3020a is in their respective first, closed position. (See FIG. 23A). For other applications a single zipper may be satisfactorily used. For some applications a fluid seal (not expressly shown) may be formed when the perimeter of first enclosure 3022 is engaged with the perimeter of second enclosure 3024 when kits 3020 and/or 3020a are in their first, closed position.

First segment 3022 and second segment 3024 may be hinged with each other along one side of respective kits 3020 and 3020a. Fabric type hinge 3058 or other suitable low cost, reliable hinge mechanism may be used to allow movement of second segment 3024 relative to first segment 3022 to open and close the associated kit 3020 or 3020a. Handle 3026 may be attached with exterior portion of kits 3020 and 3020a opposite from the hinge 3058 located on interiors of kits 3020 and 3020a. Handle 3026 may be formed from lightweight, durable web type material or any other suitable material.

Zippers 3028 and 3029 may be moved around the three edges of contact between first enclosure 3022 and second enclosure 3024 to engage and disengage adjacent portions of enclosures 3022 and 3024. Zippers 3028 and 3029 and associated zipper mechanisms may be formed from durable, rustproof material and extend along three edges of contact between first enclosure 3022 and second enclosure 3024.

After kits 3020 and/or 3020a have been used at a field location or at a medical facility, the used kit may be returned to a central location for cleaning and replacement of any missing components or devices. For some applications breakable seal 3023 (See FIG. 23B) may be engaged with zippers 3028 and 3029 to indicate that the associated kit 3020 or 3020a has been cleaned, inspected, any missing components or devices replaced and is now ready to be used to provide access to a patient's vascular system.

One or more panels or dividers may be disposed within kits incorporating teachings of the present disclosure. The dividers may also be referred to as "boards." For embodiments represented by kits 3020 and 3020a one edge of each divider 3050 may be engaged with associated hinge 3058 to allow rotating movement of each divider 3050 relative to hinge 3058 when associated kit 3020 or 3020a is in its first, open position.

Dividers 3050 may be formed from polyvinyl chloride (PVC) or other suitable materials. Each divider 3050 may have a generally rectangular configuration with dimensions compatible with nesting each divider within segments 3022 and 3024 when associated kit 3020 or 3020a is in its first, closed position. For some applications dividers 3050 may be about 0.050 to 0.060 inches thick. The width and other characteristics of hinge 3058 may also be selected to accommodate nesting of each divider 3050 within segments 3022 and 3024 when associated kit 3020 or 3020a is in its first closed position.

Figure 24A:
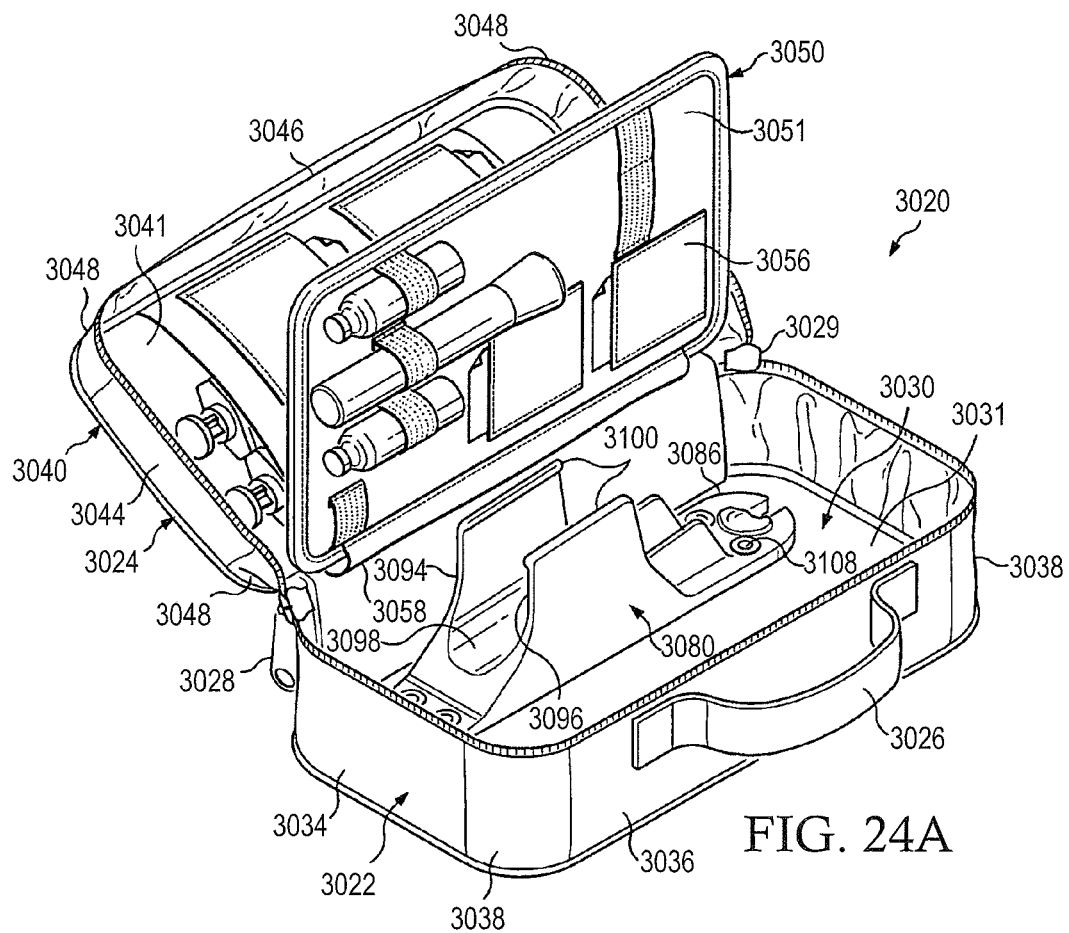
FIG. 24A is a schematic drawing showing an isometric view of the kit in FIG. 23A in an open position along with examples of intraosseous and intravenous devices and components disposed therein.
Figure 24B:
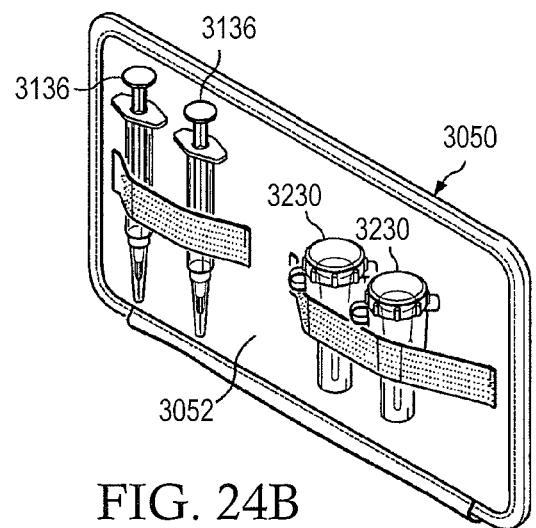
FIG. 24B is a schematic drawing showing one side of a divider or panel which may be disposed in the kit of FIG. 24A along with examples of intraosseous and intravenous devices and components attached thereto.

Each divider 3050 may also include first surface 3051 and a second surface 3052. Surfaces 3051 and 3052 may sometimes be referred to as "pages." For embodiments such as shown in FIGS. 24A, 24B and 28, first surface 3051 or page 1 and second surface 3052 or page 2 may include a plurality of holders such as elastic straps or bands 3054 and pockets 3056. Velcro type straps, holders and elastic bands may also be used.

For example, "page one" or first surface 3051 of divider 3050 may present EMS personnel with devices, components and instructions used to select and clean a site for vascular access. Such components and devices may include containers 3062 with cleaning fluids, alcohol wipes or other prep materials, flashlight 3064 and a tourniquet (not expressly shown). Written instructions for selecting an insertion site and/or locating a vein may be provided in pockets 3056 on page one.

"Page Two" or second surface 3052 of divider 3050 may include devices and components that allow EMS personnel to access a patient's vascular system via a peripheral vein or an intraosseous route. Such components may include intravenous catheters, intraosseous needles and other components that may be used to access a patient's vascular system. As shown in FIG. 24B, one or more containers 3230 with respective IO devices disposed therein may be releasably engaged with second surface 3052 or page two of divider 3050. One or more IV devices such as IV needle sets 3136 may also be releasably engaged with second surface 3052. Each IV needle set 3136 may include a syringe, IV needle and cover for the IV needle.

For some applications, interior surface 3041 of cover 3040 may also function as page three with additional devices, components and instructions attached thereto. For example, when kits 3020 and/or 3021a are used in an emergency environment to provide IO access to a patient, interior surface 3041 or page three may include devices and components used to secure and intraosseous device and/or an IV device at the insertion site and to further prepare the patient for movement to an EMS treatment facility. Components and devices such as tape, dressing materials, an arm-board or splint and other components operable to secure a catheter or an intraosseous line may be provided on page three. Various types of straps and supporting structures for IO devices may be releasably attached to page three or interior surface 3041. See some examples in FIGS. 30-39.

Outside pocket 3060 formed from mesh type material may be attached to exterior surface 3042 of cover 3040. Outside pocket 3060 may hold printed reference materials such as quick reference cards. For some applications elastic cords (not expressly shown) may also be provided on exterior portion of kits 3020 and 3020a to hold such materials.

Velcro or elastic strips or loops or any other fastening device may be used to position components on dividers 3050. In lieu of dividers 3050, IO and IV devices and related components may be configured in some other arrangement or organizing mechanism such as compartments or smaller containers carried in a kit.

A device for accessing an intraosseous space such as a powered driver (See FIG. 26) or a manual driver (See FIGS. 40A and 41) may be carried in first segment 3022. For some applications a securing device such as shown in FIGS. 24A, 25, 27 and 28 may be disposed within first segment 3022 to releasably hold a driver. For other applications a powered driver and/or manual driver may be placed in a collapsible bag or pouch and placed within first segment 3022 or other portions of kit 3020 and/or 3020a. For still other applications a powered driver and/or manual driver may be carried in a bag or pouch attached to exterior portions (not expressly shown) of kit 3020 and/or 3020a.

Powered driver 3200 may include housing 3202 with various types of motors and/or gear assemblies disposed therein (not expressly shown). A rotatable shaft (not expressly shown) may be disposed within housing 3202 and connected with a gear assembly. Various types of fittings and/or connectors may be disposed proximate one end of the rotatable shaft extending from end 3204 of housing 3202. For some applications a pin type fitting or connector such as drive shaft 3216 may be used. A matching box type fitting or connector receptacle may be provided on an intraosseous device such that power driver 3200 may be releasably engaged with the intraosseous device. For some applications, drive shaft 3236 may have a pentagonal shaped cross section with tapered surfaces formed on the exterior thereof. Fittings and/or connections with various dimensions and configurations may be satisfactorily used to releasably engage an intraosseous device with a powered driver.

Figure 40B:
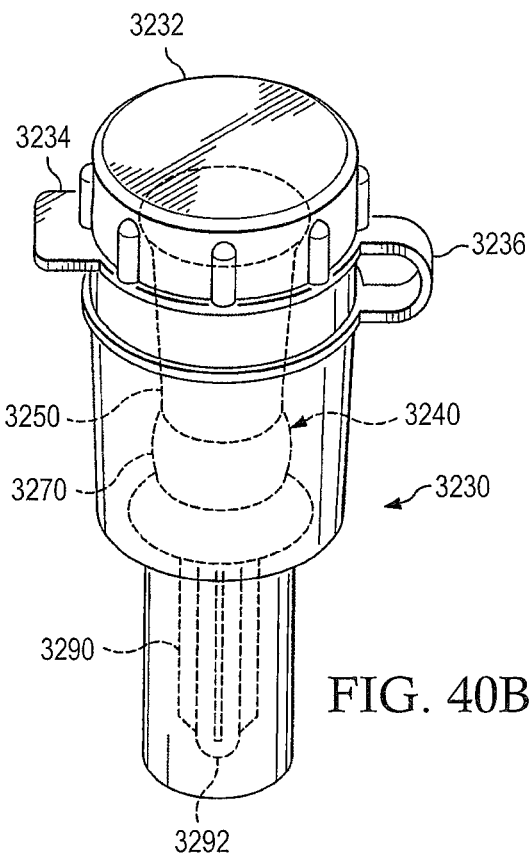
FIG. 40B is a schematic drawing showing an isometric view of a container with one example of an intraosseous device disposed therein.

Container 3230 as shown in FIGS. 24B and 40B may include lid 3232 along with associated tab 3234. Tab 3234 may be configured to be flipped open with one or more digits of an operator's hand. With lid 3232 open, an operator may releasably engage a driver with an IO device disposed in container 3230. For example, drive shaft 3216 of powered driver 3200 may be releasably engaged with box type connector or receptacle 3258 of penetrator assembly 3240. See FIGS. 26 and 40A. Flexible strap 3236 may be used to retain lid 3232 with container 3230 after lid 3232 has been opened.

Handle 3206 may include a battery (not expressly shown) or other power source. Handle 3205 may also include trigger assembly 3208 for use in activating powered driver 3200. Examples of powered drivers are shown in U.S. patent application Ser. No. 10/449,503, filed May 30, 2003, entitled "Apparatus and Method to Provide Emergency Access To Bone Marrow," now U.S. Pat. No. 7,670,328; U.S. patent application Ser. No. 10/449,476, filed May 30, 2003, entitled "Apparatus and Method to Access Bone Marrow," now U.S. Pat. No. 7,699,850; and U.S. patent application Ser. No. 11/042,912, filed Jan. 25, 2005, entitled "Manual Intraosseous Device," now U.S. Pat. No. 8,641,715.

Various types of intraosseous devices, intraosseous needles and/or penetrator assemblies may be carried in a kit incorporating teachings of the present disclosure. See for example FIG. 24B. Intraosseous devices 3160 and 3160a which are shown in FIGS. 30, 33, 34 and 35 may be carried in a kit along with powered driver 3200 and inserted into a patient's bone marrow in accordance with teachings of the present disclosure.

For some applications a securing device designed to accommodate one or more specific types of drivers may be disposed within first segment 3022. For other applications more generic types of holders or cradles may be placed within first segment 3022. For embodiments such as shown in FIGS. 24A, 25, 27 and 28, securing device or cradle 3080 may be designed to accommodate powered drivers such as powered driver 3200. Cradles and holders incorporating teachings of the present disclosure may be fabricated from a wide variety of thermoplastic and/or polymeric materials filled with glass fibers.

Length 3082 and width 3084 of cradle 3080 may be selected to be compatible with interior dimensions of first enclosure 3022 and similar dimensions associated with a driver that will be releasably engaged with cradle 3080. For some applications first end 3086 and second end 3088 may have generally rounded configurations. Notch 3090 may be formed in first end 3086 to accommodate drive shaft 3216 extending from end 3204 of power driver 3200.

First longitudinal edge 3091 and second longitudinal edge 3092 may be spaced from each other and extend generally parallel with each other between first end 3086 and second end 3088. For some applications, ends 3086, 3088 and longitudinal edges 3091, 3092 may fit flush with interior surface 3031 of bottom layer 3030. Maintaining close contact between interior surface 3031 and adjacent portions of cradle 3080 may substantially reduce or minimize problems associated with cleaning an associated kit after use, particularly after used during an emergency at a field location.

Various types of holders, clamps and/or quick release mechanisms may be provided on a cradle incorporating teachings of the present disclosure. For embodiments represented by cradle 3080 a pair of arms 3094 and 3096 may project from respective longitudinal edges 3091 and 3092. Arms 3094 and 3096 may be relatively strong with sufficient flexibility to allow inserting and removing portions driver 3200 from engagement with cradle 3080. The height of arms 3094 and 3096 relative to longitudinal edges 3091 and 3092 may be based at least in part on the height or depth of first enclosure 3022 and corresponding dimensions of driver 3200. Support surface 3098 may be disposed between arms 3094 and 3096 in an elevated position relative to longitudinal edges 3091 and 3092. The location of support surface 3098 may be selected to accommodate corresponding dimensions of driver 3200 and particularly handle 3206.

The spacing or gap formed between first arm 3094 and second arm 3096 may be selected to accommodate the width of handle 3206 of driver 3200. Respective ribs 3100 may be formed approximate the end of each arm 3094 and 3096 opposite from longitudinal edges 3091 and 3092. Ribs 3100 preferably extend inwardly relative to associated arm 3094 and 3096. The dimensions of arms 3094 and 3096, the gap formed therebetween, and associated ribs 3100 may be selected to be compatible with forming a snug but releasable snap type fit with adjacent portions of handle 3206 of driver 3200.

Figure 25:
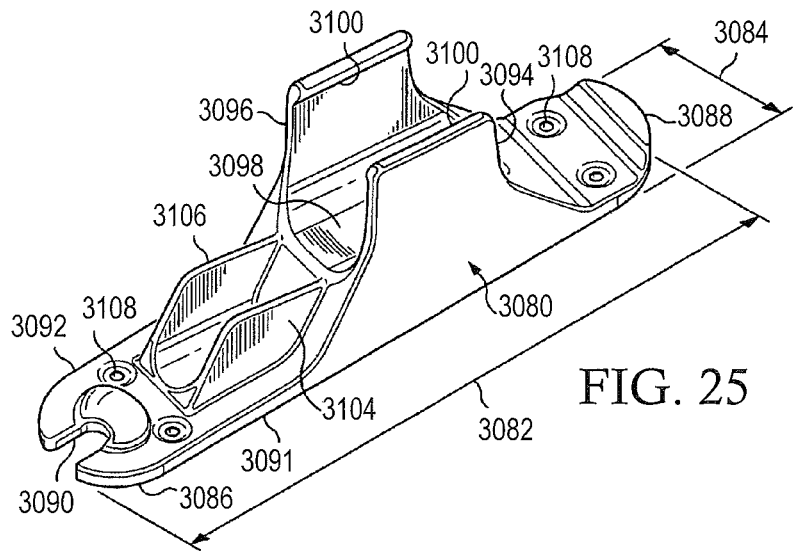
FIG. 25 is a schematic drawing showing an isometric view of one example of a securing device which may be installed in a kit to releasably hold a drive in accordance with teachings of the present disclosure.
Figure 26:
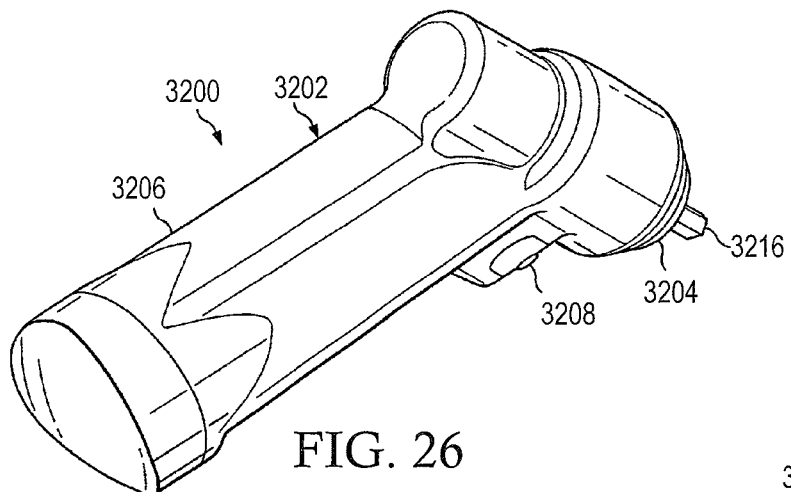
FIG. 26 is a schematic drawing showing one example of a powered driver and penetrator assembly which may be included in a kit in accordance with teachings of the present disclosure.
Figure 27:
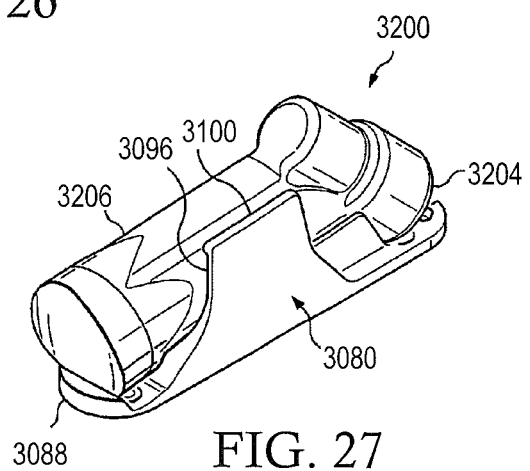
FIG. 27 is a schematic drawing showing an isometric view of one example of a powered driver and securing device releasably engaged with each other in accordance with teachings of the present disclosure.

For some applications first wall 3104 and second wall 3106 may be disposed between first end 3086 and supporting surface 3098 such as shown in FIG. 25. The spacing between first wall 3104 and second wall 3106 may be selected to correspond with corresponding dimensions of handle 3206 of driver 3200 and particularly dimensions associated with trigger assembly 3208. Walls 3104 and 3106 may cooperate with each other to provide a "trigger guard" to prevent accidental activation of driver 3200 when kit 3020 and/or 3020a are in their first, closed position.

One or more holes 3108 may be formed in cradle 3080 approximate first end 3086 and second end 3088. Holes 3108 may be sized to receive various types of fasteners such as rivets and/or screws (not expressly shown). Such fasteners may be used to secure cradle 3080 at a desired location within first enclosure 3022.

Materials used to form cradle 3080 may be relatively low cost but must also have sufficient durability for repeated insertion and removal of an associated driver. For some applications arms 3094 and 3096 may be designed to allow insertion and removal of an associated driver at least five hundred times. Arms 3094 and 3096 may also have sufficient stiffness and strength to allow associated driver 3200 to snap into place. The stiffness of arms 3094 and 3096 may be selected such that driver 3200 will not be inadvertently released from cradle 3080 if kit 3020 or 3020*a* should be dropped or otherwise mishandled.

For embodiments such as shown in FIG. 28, second end 3088 (not expressly shown) of cradle 3080*a* may be modified to include electrical contacts used to charge a battery or other power source disposed in handle 3206 of driver 3200. Electrical connector assembly 3070 may be disposed on exterior portions of wall 3034*a* to accommodate inserting charging cable 3072 extending from an appropriate charger (not expressly shown). Lights 3074 and 3076 may be provided as part of electrical connector assembly 3070 to indicate the status of a battery or other power source disposed in handle 3206 after each use of powered driver 3200 and to indicate the status of recharging powered driver 3200.

Various types of indicator lights may be used. For some applications light 3074 may be yellow to indicate that a battery (not expressly shown) in power driver 3200 needs to be recharged. Light 3076 may be green to indicate that the charging is not required or that charging of associated powered driver 3200 has been satisfactorily completed. For some applications, kit 3020*a* will preferably be in its first, open position during charging of powered driver 3200.

Prehospital and combat situations are often ideally suited to use "unit dose" containers of various types of medications. Emergency medical personnel often need only a one-time dose of medication, such as an antidote for poison or epinephrine to stabilize the patient. Unit dose ampules are widely used by paramedics to give a predetermined amount of medication for a particular indication. A limited number of drugs may satisfactorily fill such needs.

Kit 3120 as shown in FIGS. 29A and 29B represents one example of a kit containing unit doses in accordance with teachings of the present disclosure. For some applications, kit 3120 may be carried separate from previously discussed kits 3020 and 3020*a*. For other applications kit 3120 may be disposed within kits 3020 and/or 3020*a*. Kit 3120 is shown in FIG. 29B in its second, open position with cover 3140 removed to provide access to ampules 3123-3127 containing respective unit doses of medication.

Figure 23A:
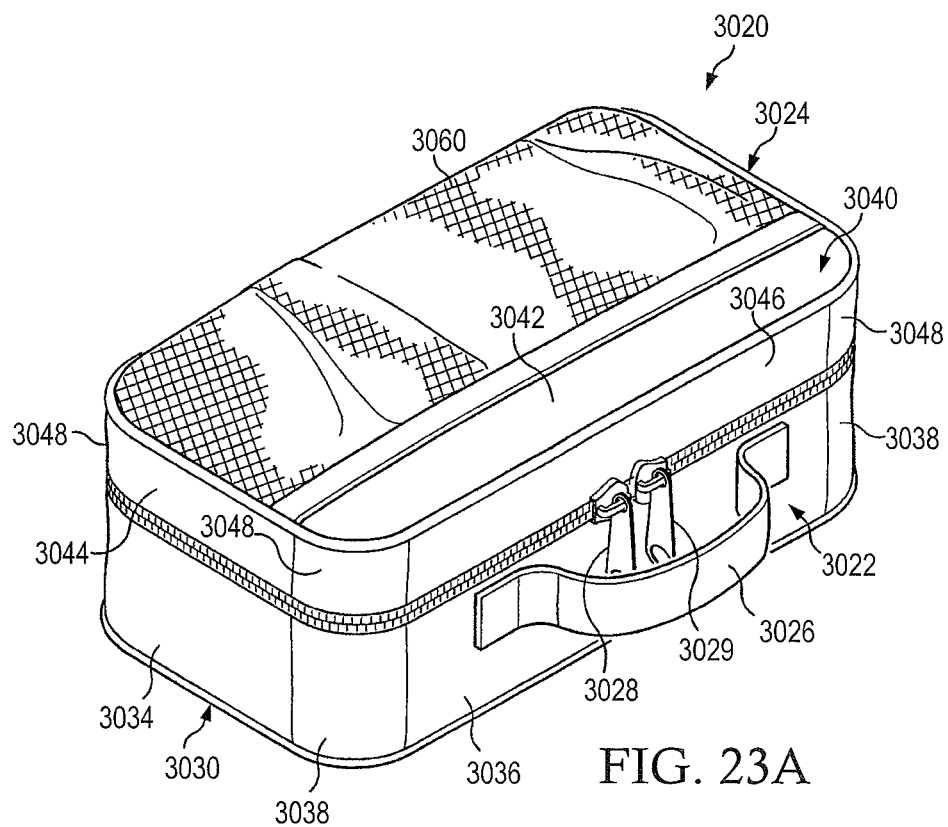
FIG. 23A is a schematic drawing showing an isometric view of one example of a kit which may be used to obtain access to a patient's vascular system in a first, closed position.
Figure 23B:
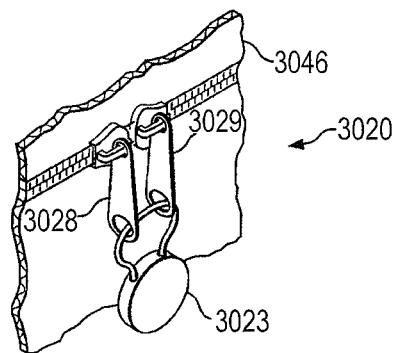
FIG. 23B is a schematic, drawing with portions broken away showing one example of a breakable seal which may be used to indicate status of the kit of FIG. 23A.

Kit 3120 may include base portion 3130 and cover 3140. Zipper 3122 or other types of closures may be satisfactorily used to releasably engage cover 3140 with base portion 3130. For some applications a pair of zippers and a breakable seal such as shown in FIG. 23B may be used with kit 3120. Kit 3120 is shown in FIG. 29A in its first, closed position with cover 3140 releasably engaged with base portion 3130.

For embodiments such as shown in FIGS. 29A and 29B, kit 3120 may be described as having a generally rectangular configuration with rounded corners. Cover 3140 may be generally described as a hollow enclosure defined in part by top layer 142 with four (4) walls extending therefrom. Walls 3143 and 3144 are shown in FIG. 29A. Interior portions of cover 3140 are preferably open to accommodate storage of ampules 3123-3127.

Base 3130 may be formed from a relatively thick layer of material satisfactory for use. A plurality of holes may be formed in interior surface 3032 of base 3130 satisfactory to accommodate releasably storing each ampule 3123-3127 in a respective hole. The exterior configurations of base 3130 may also be defined in part by walls and rounded corners which are preferably compatible with the walls and rounded corners associated with cover 3140.

Base portion 3130 as shown in FIG. 29B may function as a rack releasably holding a plurality of single use (unit dose) ampules which may meet many (if not most) of an emergency medical service provider's immediate needs. For example, ampule 3123 may contain epinephrine for cardiac arrest and life threatening allergies. Ampule 3124 may contain atropine for cardiac arrest and chemical exposures. Ampule 3125 may contain diazepam for seizures and emergency sedation. Ampule 3126 may contain amiodarone for cardiac arrhythmias. Ampule 3127 may contain narcan for drug overdose. Each ampule 3123-3127 may be clearly labeled so that an appropriate drug may be quickly and accurately selected in an emergency. As shown in FIGS. 29A and 29B, kit 3120 may contain medications in an easy to carry and maintain rack or stand such as base 3130. Kit 3120 may include zip lock cover 3140 which is easy to remove in an emergency.

The ability to satisfactorily insert an IO device such as an IO needle at a desired insertion site may be problematic when a patient is moving or has the potential to move. Inserting an IO device in the wrong place may expose a patient to potential harm. Patient movement may be of special concern for patients suffering from status epilepticus or violent patients (drug overdoses or mental status changes) that need to be controlled for their safety and treatment. Epileptic patients may shake violently for prolonged periods which makes starting a conventional IV nearly impossible. Likewise, it may be difficult to accurately place an IO device at a desired insertion site in these patients. Although target areas for successful IO placement such as a patient's tibia and humerus are often larger than target areas for placement of an IV device, problems with inserting an IO device at a desired insertion site may be minimized by using stabilization devices and supporting structures incorporating teachings of the present disclosure. Such devices and supporting structures may be easy to apply, even in difficult field environments.

FIGS. 30, 33, 34, 35, 36 and 39 show various examples of an intraosseous device inserted into a patient's bone marrow to provide vascular access in accordance with teachings of the present disclosure. Bone 3152 and associated bone marrow 3154, shown in FIGS. 30, 33, 34, 35, 36 and 39, may be representative of the tibia in a patient's leg. The upper tibia proximate a patient's knee may often be used as an insertion site for IO access to a patient's vascular system. A humerus may also be used as an insertion site for IO access to a patient's vascular system.

Figure 30:
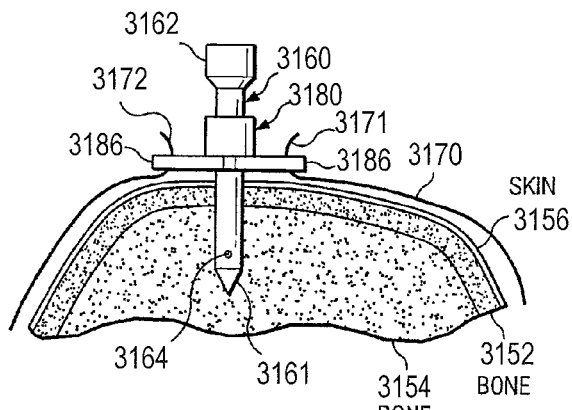
FIG. 30 is a schematic drawing in section showing an intraosseous device inserted into bone marrow of a patient after using various devices and components carried in a kit in accordance with the teachings of the present disclosure.

FIG. 30 shows one example of an intraosseous device which may have been inserted into a patient's bone marrow using a kit containing various devices and components in accordance with teachings of the present disclosure. For this example, intraosseous device 3160 may be generally described as intraosseous (IO) needle 3160 having a hollow, longitudinal bore extending therethrough (not expressly shown). IO devices 3160 may be releasably attached to page 2 of kits 3020 and/or 3020*a*.

First end or tip 3161 of IO needle 3160 may be designed to drill or cut through bone 3152 and penetrate associated bone marrow 3154. Tip 3161 may be open to allow communication of fluids with bone marrow 3154. Also, one or more side ports 3164 may be formed in IO needle 3160 to allow communication of fluids therethrough. Second end 3162 of IO needle 3160 may have various types of connections including, but not limited to, a conventional Luer lock connection (not expressly shown) associated with supplying IV fluids and medications to a patient.

Figure 31:
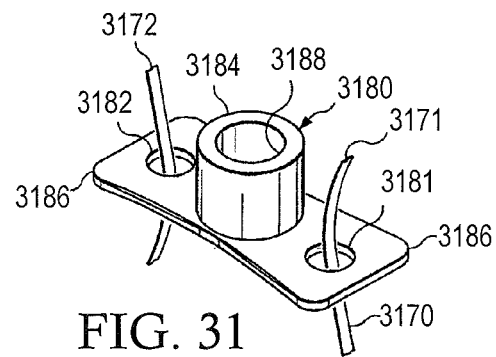
FIG. 31 is a schematic drawing in elevation with portions broken away showing one example of a strap and supporting structure which may be carried in a kit and used to position an intraosseous device at a selected insertion site.

Strap 3170 and supporting structure 3180 such as shown in FIGS. 30 and 31 may be carried in a kit in accordance with teachings of the present disclosure. Strap 3170 may be formed from various types of elastomeric and/or nonelastomeric materials compatible with contacting skin 3156 and other soft tissue covering a patient's bone at a selected insertion sight. The dimensions and configuration of strap 3170 may be selected to form satisfactory engagement with adjacent portions of leg 3150, an arm, or other desired sites for providing IO access to a patient's vascular system.

Strap 3170 may include first end 3171 and second end 3172 sized to be inserted through holes 3181 and 3182 of supporting structure 3180. Strap 3170 and supporting structure 3180 cooperate with each other to prevent accidental removal or withdrawal of IO needle 3160 from an insertion site. Strap 3170 and supporting structure 3180 also cooperate with each other to prevent excessive movement or rocking of IO needle 3160 relative to the insertion site.

Supporting structure 3180 may include relatively short, hollow cylinder 3184 with a pair of flanges or wings 3186 extending therefrom. Holes 3181 and 3182 may respectively be formed in each wing or flange 3186. Wings 3186 may be formed from relatively flexible material which will conform with adjacent portions of a patient's skin, soft tissue and bone. Hollow cylinder 3184 may be formed from relatively rigid material to prevent undesired movement of associated 3010 needle 3160. Interior dimensions of hollow cylinder 3184 may correspond approximately with the exterior dimensions of IO needle 3160 to provide a relatively snug fit therebetween.

Figure 32:
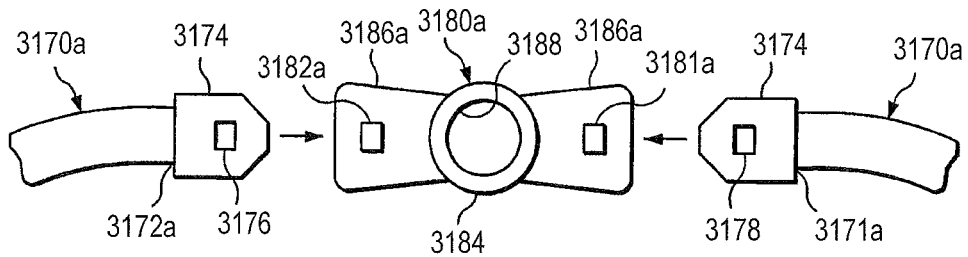
FIG. 32 is a schematic drawing showing a plan view with portions broken away of another example of a strap and supporting structure which may be carried in a kit and used to position an intraosseous device at a selected insertion site.

For embodiments such as shown in FIG. 32, supporting structure 3180a may include wings or tabs 3186a which have been modified to include respective projections 3181a and 3182a extending there from. Strap 3170a may be modified as compared with strap 3170 by attaching respective buckles 3174 with first end 3171a and second end 3172a. Each buckle 3174 may include respective hole 3176 sized to receive associated projection 3181a and 3182a formed on tabs 3186a.

Supporting structure 3180a may be placed at an IO insertion site. Buckle 3174a at first end 3171a of strap 3170a may be releasably engaged with corresponding projection 3181a. Strap 3170a may then be extended around patient's leg or other bone to allow engaging buckle 3174a at second end 3172a with associated projection 3182a. For such applications, strap 3170a may be formed from elastomeric material.

For some applications supporting structure 3180 may be placed at an insertion site prior to installing IO device 3160. IO device 3160 may then be inserted through the longitudinal bore of supporting structure 3180. For other applications an IO device with exterior dimensions and exterior configuration of the IO device may be compatible with interior dimensions 3188 of supporting structure 3180 may first be installed at a desired insertion site. Supporting structure 3180 may then be fitted over the installed IO device (not expressly shown) by placing the IO device through the longitudinal bore of supporting structure 3180. Strap 3170a may then be engaged with respective projections 3181 and 3182.

Figure 33:
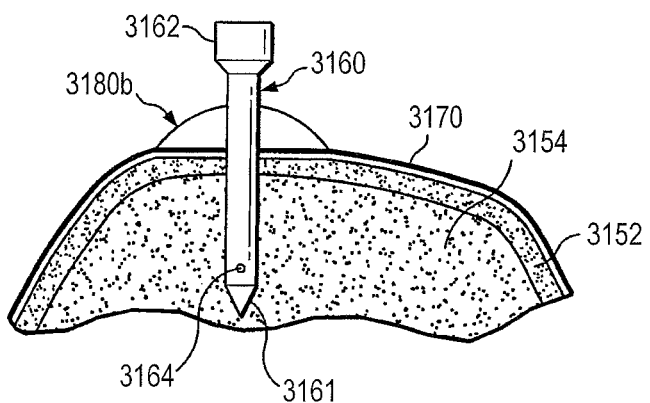
FIG. 33 is a schematic drawing in section and in elevation showing an intraosseous device inserted into bone marrow of a patient along with another example of a strap and supporting structure which may be carried in a kit in accordance, with teachings of the present disclosure.
Figure 36:
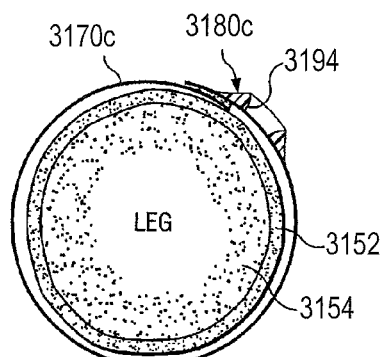
FIG. 36 is a schematic drawing in section showing another example of a strap and supporting structure which may be satisfactorily used to position an intraosseous device at a selected insertion site.
Figure 37:
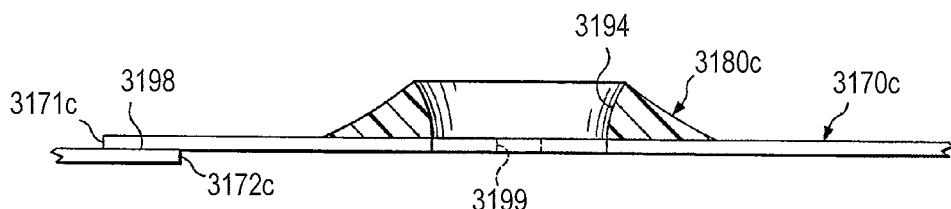
FIG. 37 is a schematic drawing in section with portions broken away of the strap and supporting structure of FIG. 36.

FIG. 33 shows IO needle 3160 inserted into bone marrow 3154. Supporting structure 3180b may be used to stabilize IO needle 3160 and limit excessive movement relative to bone 3152. Supporting structure 3180b may be generally described as having a domed shape configuration. The dimensions of supporting structure 3180b may be selected to be compatible with a desired insertion site. A longitudinal bore or a longitudinal opening (not expressly shown) may extend through supporting structure 3180b. The longitudinal bore may have dimensions compatible with exterior dimensions of IO needle 3160. Supporting structure 3180b may be formed from various types of semi-rigid silicone based materials and/or materials satisfactory for providing required support. A pair of holes (not expressly shown) may be provided in supporting structure 3180b to accommodate the use of strap 3170. However, other straps such as shown in FIGS. 32, 36 and 37 and/or adhesive materials (not expressly shown) may be satisfactory used to position supporting structure 3180 at a desired insertion site.

Figure 34:
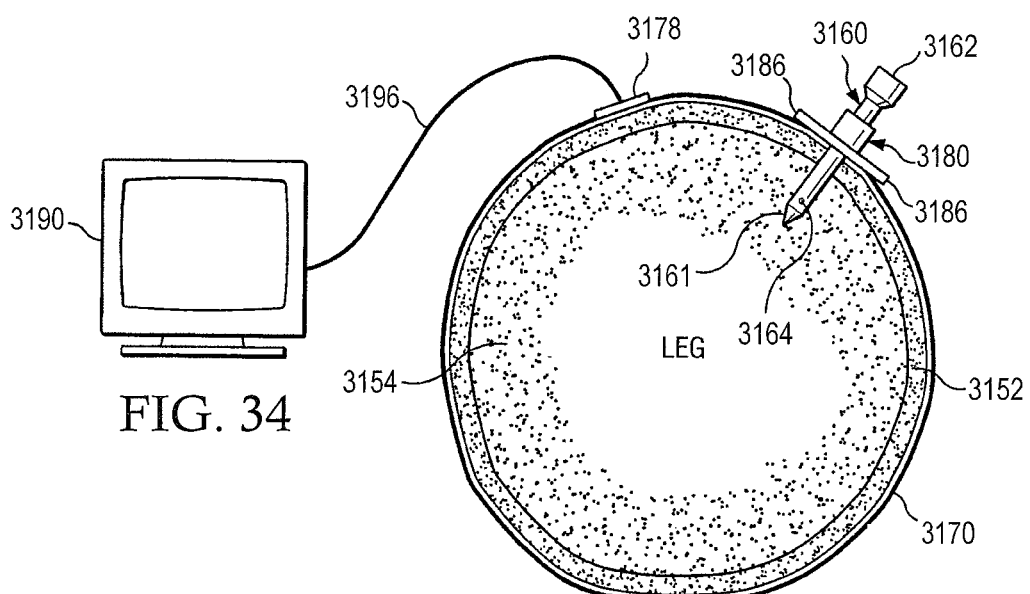
FIG. 34 is a schematic drawing in section showing an intraosseous device inserted into bone marrow of a patient along with another example of a strap and supporting structure which may be carried in a kit in accordance with teachings of the present disclosure.

FIG. 34 shows IO 3160 inserted into bone 3152 and associated bone marrow 3154. Strap 3170 may be placed around bone 3152 and attached to supporting structure 3180 as previously described. Sensor 3178 may be attached to strap 3170 for use in measuring various parameters associated with providing fluids and/or medications through IO device 3160 to bone marrow 3154. Such parameters may include, but are not limited to, pressure and/or changes in the size of a patient's leg, temperature and/or pulse rate. When sensor 3178 detects a preset value for one or more of these parameters, an alarm may be sounded. For some applications sensor 3178 may be coupled with monitor 3190 and/or a general purpose computer (not expressly shown). The general purpose computer may include one or more programs operable to stop infusion of fluids and/or medication through associated IO device 3160 in the event one or more parameters exceeds preset limits.

Figure 35:
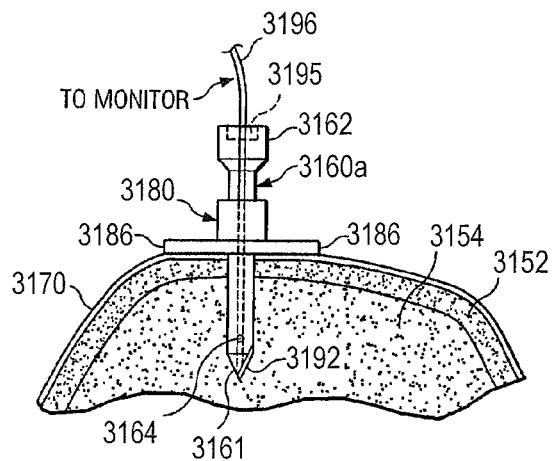
FIG. 35 is a schematic drawing in section showing an intraosseous device inserted into bone marrow of a patient along with another example of a strap and supporting structure which may be carried in a kit in accordance with teachings of the present disclosure.

FIG. 35 shows IO device 3160a inserted into bone 3152 and associated bone marrow 3154. IO device 3160a may be equipped with pressure transducer 3192 proximate tip 3161 to measure intraosseous pressure. For some applications, a similar needle (not expressly shown) may be placed in a leg muscle to measure intra-compartment pressure.

Seal assembly 3195 may be used to isolate transducer wire 3196 so that infusions of fluids may proceed while, at the same time, measuring intravenous pressure at tip 3161. Measurements from sensor 3192 may be analyzed by a computer (not expressly shown) to manage changes in a patient's condition by initiating pre-set increases in infusion pressure, controlling the rate of infusion or stopping infusion all together and alarming the patient and/or medical personnel if pressure limits are exceeded.

Figure 38:
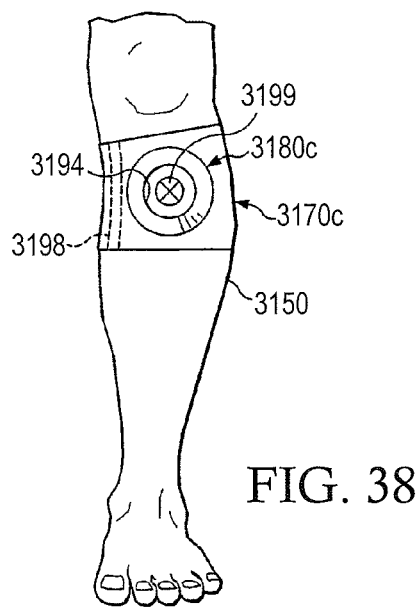
FIG. 38 is a schematic drawing showing an isometric view with portions broken away of the strap and supporting structure of FIGS. 36 and 37 releasably attached to the leg of a patient proximate the tibia.

FIGS. 36, 37 and 38 show one example of a supporting structure or guide which may be disposed at a desired insertion site such as the upper tibia proximate a patient's knee. Supporting structure or guide 3180c may be generally described as having a dome shaped configuration with cavity or recess 3194 formed therein and sized to receive an intraosseous device. For example, recess 3194 may be sized to accommodate an intraosseous device such as penetrator assembly 3240. See for example FIG. 39.

Supporting structure or guide 3180c may be formed from various polymeric and/or thermoplastic materials having desired rigidity and strength to direct insertion of an intraosseous device at a desired insertion site. Supporting structure 3180c may also be formed from various types of elastomeric and/or nonelastomeric materials satisfactory for use in forming a guide or supporting structure to direct insertion of an intraosseous device at a desired insertion site.

For some applications strap 3170c may include one or more strips of hook and loop type material 3198 (sometimes referred to as Velcro® strips) disposed proximate first end 3171c and second end 3172c of strap 3170c. The configuration, size and dimensions of Velcro® strips 3198 may be modified to allow strap 3170c to releasably attach supporting structure 3180c with a leg or other portions of a patient's body having various dimensions. For some applications supporting structure 3180c may include target 3199 disposed within recess 3194 for use by an operator to more precisely direct insertion of an associated IO device at a desired insertion site.

FIG. 39 shows powered driver 3200 being used to insert penetrator assembly 3240 at an insertion site identified by guide or supporting structure 3180c. Powered driver 3200 may be further stabilized with various types of straps and/or medical grade tape (not expressly shown) prior to inserting penetrator assembly 3240.

Figure 41:
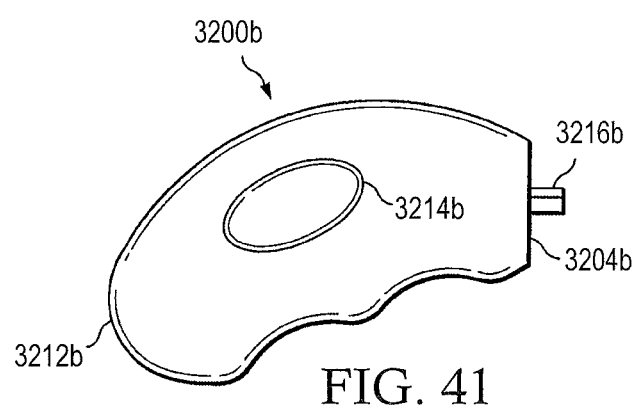
FIG. 41 is a schematic drawing showing another example of a manual driver which may be carried in a kit in accordance with teachings of the present disclosure.

FIGS. 40A and 41 show examples of manual drivers which may be carried in a kit in accordance with teachings of the present disclosure. For some applications, a kit may contain only a powered driver or only a manual driver. For other applications, a kit incorporating teachings of the present disclosure may include both a powered driver and a manual driver. Examples of manual drivers are shown in U.S. patent application Ser. No. 10/449,503, filed May 30, 2003, entitled "Apparatus and Method to Provide Emergency Access To Bone Marrow," now U.S. Pat. No. 7,670,328; and U.S. patent application Ser. No. 11/042,912, filed Jan. 25, 2005, entitled "Manual Intraosseous Device," now U.S. Pat. No. 8,641,715.

Manual driver 3200a may include handle 3212 with drive shaft 216 extending therefrom. Manual driver 3200a may also include an optional ratchet mechanism (not expressly shown). Handle 3212 may be formed in a variety of shapes, such as with finger grips 3214. Handle 3212 may be formed from materials satisfactory for multiple uses or may be formed from materials satisfactory for one time or disposable use. Handle 3212 may have an ergonomically designed shape suitable for grasping with a hand and/or fingers during manual insertion of an IO device into bone and associated bone marrow.

FIG. 40A shows an exploded view of manual driver 3200a and penetrator assembly 3240. Penetrator assembly 3240 may include an outer penetrator such as a cannula, hollow tube or hollow drill bit and an inner penetrator such as a stylet or trocar. Various types of outer penetrators may be used to form a portion of penetrator assembly 3240. Various types of stylets and/or trocars may be disposed within an outer penetrator.

For some applications penetrator assembly 3240 may include connector 3250 with inner penetrator or trocar 3260 extending therefrom and hub 3270 with outer penetrator or cannula 3280 extending therefrom. Connector 3250 and hub 3270 may be releasably engaged with each other using Luer type fittings, threaded connections or other suitable fittings formed on second end 3252 of connector 3250 and first end 3271 of hub 3270. Outer penetrator 3280 may extend from second end 3272 of hub 3270.

For some applications outer penetrator or cannula 3280 may be described as a generally elongated tube sized to receive inner penetrator or stylet 3260 therein. Portions of inner penetrator 3260 may be disposed within a longitudinal passageway 3276 extending through outer penetrator 3280. The outside diameter of inner penetrator 3260 and the inside diameter of longitudinal passageway 3276 may be selected so that inner penetrator 3260 may be slidably disposed within outer penetrator 3280. Outer penetrator 3280 may be formed from stainless steel, titanium or other materials of suitable strength and durability to penetrate bone and magnetic characteristics to allow releasable engagement with disc 3254.

Tip 3281 of outer penetrator 3280 and/or tip 3261 of inner penetrator 3260 may be operable to penetrate bone and associated bone marrow. The configuration of tips 3261 and/or 3281 may be selected to penetrate a bone or other body cavities with minimal trauma. First end or tip 3261 of inner penetrator 3260 may be trapezoid shaped and may include one or more cutting surfaces. In one embodiment outer penetrator 3280 and inner penetrator 3260 may be ground together as one unit during an associated manufacturing process. Inner penetrator 3260 may also include a longitudinal groove (not expressly shown) that runs along the side of inner penetrator 3260 to allow bone chips and/or tissues to exit an insertion site as penetrator assembly 3240 is drilled deeper into an associated bone.

Hub 3270 may be used to stabilize penetrator assembly 3240 during insertion of outer penetrator 3280 into a patient's skin, soft tissue and adjacent bone at a selected insertion site. First end 3271 of hub 3270 may be operable for releasable engagement or attachment with associated connector 3250. Second end 3272 of hub 3270 may have a size and configuration compatible with an associated insertion site. The combination of hub 3270 with outer penetrator 3280 may sometimes be referred to as a penetrator set or an intraosseous needle.

For some applications connector 3250 may be described as a generally cylindrical tube defined in part by first end 3251 and second end 3252. The exterior of connector 3250 may include an enlarged tapered portion adjacent to end 3251. A plurality of longitudinal ridges 3256 may be formed on the exterior of connector 3250 to allow an operator to grasp associated penetrator assembly 3240 during attachment with drive shaft 3216. Longitudinal ridges 3256 also allow connector 3250 to be grasped for disengagement from hub 3270 after outer penetrator 3280 has been inserted into a bone and associated bone marrow. Disc 3254 may be disposed within receptacle or opening 3256 for use in releasably attaching connector 3250 with drive shaft 3216.

For some applications disc 3254 may be a magnet. For such applications drive shaft 3216 may be formed from various types of metallic materials with magnetic characteristics compatible with releasable engagement of drive shaft 3216 with the magnetic disc 3254 disposed in penetrator assembly 3240. For other applications a magnet (not expressly shown) may be formed on the end of drive shaft 3216. For such applications disc 3254 may be formed from various types of metallic material with characteristics compatible with releasably engaging penetrator assembly 3240 with the magnet formed on the end of drive shaft 3216.

First end 3271 may have a generally cylindrical pin type configuration compatible with releasably engaging hub 3270 with second end or box end 3252 of connector 3250. Second end 3252 of connector 3250 may include opening 3258 sized to receive first end 3271 of hub 3270 therein. Threads 3259 may be formed in opening 3258 adjacent to second end 3252 of connector 3250. Threads 3273 may be formed proximate end 3271 of hub 3270. Threads 3259 and 3273 may be used to releasably attach connector 3250 with first end 3271 of hub 3270.

For some applications end 3272 of hub 3270 may have the general configuration of flange. Angular slot or groove 3274 sized to receive one end of protective cover or needle cap 3290 may be formed in end 3272. Slot or groove 3274 may be used to releasable engage cover 3290 with penetrator assembly 3240. For some applications cover 3290 may be described as a generally hollow tube having rounded end 3292. Cover 3290 may be disposed within associated slot 3274 to protect portions of outer penetrator 3280 and inner penetrator 3260 prior to attachment with a driver. Cover 3290 may include a plurality of longitudinal ridges 3294 formed on the exterior thereof. Longitudinal ridges 3294 cooperate with each other to allow installing and removing cover or needle cap 3290 without contaminating portions of an associated penetrator. Cover 3290 may be formed from various plastics and/or metals.

FIG. 40B shows container 3230 with penetrator assembly 3240 disposed therein. One of the benefits of the present disclosure includes providing a kit which allows an operator to remove a driver from a holder contained within the kit using one hand. The other hand of the operator may remove container 3230 from page two of divider 3050 and open lid 3232 of container 3230 using one hand. Drive shaft 3216 may be releasably engaged with receptacle 3258 in end 3251 of connector 3250.

FIG. 41 shows another example of a manual driver which may be used to insert an IO device into bone marrow in accordance with teachings of the present disclosure. Manual driver 3200b may include pistol grip type handle 3212b with drive shaft 3216 extending therefrom. Manual driver 3200b may also include an optional ratchet mechanism (not expressly shown). Manual driver 3200b may be releasably engaged with penetrator assembly 3240 or any other IO device incorporating teachings of the present disclosure.

Examples of acute and chronic conditions which may be treated using powered drivers, intraosseous devices, kits, and procedures incorporating teachings of the present disclosure include, but are not limited to, the following:

Anaphylaxis (epinephrine, steroids, antihistamines, fluids, and life support)

Arrhythmia (anti-arrhythmics, electrolyte balance, life support);

Burns (fluid replacement, antibiotics, morphine for pain control);

Cardiac arrest (epinephrine, atropine, amiodarone, calcium, xylocaine, magnesium);

Congestive heart failure (life support, diuretics, morphine, nitroglycerin);

Dehydration (emergency port for life support, antibiotics, blood, electrolytes);

Diabetic Ketoacidosis (life support, electrolyte control, fluid replacement);

Dialysis (emergency port for life support, antibiotics, blood, electrolytes);

Drug overdose (naloxone, life support, electrolyte correction);

Emphysema (life support, beta adrenergics, steroids);

Hemophiliacs (life support, blood, fibrin products, analgesics);

Osteomyelitis (antibiotics directly into the site of infection, analgesics);

Pediatric applications (shock, dehydration, nutrition, electrolyte correction);

Renal Failure (both acute and chronic kidney failure, inability to purify blood);

Seizures (anti-seizure medications, life support, fluid balance);

Shock (life support fluids, pressor agents, antibiotics, steroids);

Sickle cell crisis (fluid, morphine for pain, blood, antibiotics); and

Trauma (emergency port for life support fluids, antibiotics, blood, electrolytes).

More than 35,000 Advanced Cardiac Life Support (ACLS) ambulances are in service in the U.S. Each is equipped with emergency drugs and devices. Most are required to carry intraosseous needles and paramedics are trained in their use for pediatric emergencies. Kits incorporating teachings of the present disclosure may be used to administer medications and treats before permanent damage to a patient occurs.

More than 4,000 emergency rooms in the U.S. are required to treat life-threatening emergencies like shock trauma and cardiac arrest. ERs are stocked with the latest devices and equipment to help patients receive state-of-the-art treatment. However, there is no more exasperating situation for the physician or potentially catastrophic condition for the critical patient, than the inability to establish intravenous access. Kits with IO devices incorporating teachings of the present disclosure may provide a simple and straightforward solution for extremely difficult clinical problems.

Hospitals are required to provide crash carts on every patient ward. It is estimated that 6,000 U.S. hospitals stock more than 60,000 crash carts. These crash carts are stocked with defibrillators, IV access devices, including central venous catheters, IV fluids and drugs for common emergencies. Nurses and other healthcare workers using these crash carts are often inexperienced in such emergencies and have difficulty establishing IV access. A kit with IO devices incorporating teachings of the present disclosure may provide the long sought IV alternative for difficult patients.

Automatic injectors are widely used in the military. During Desert Storm, combat soldiers carried an atropine auto-injector for nerve gas poisoning. Current auto-injectors are limited to intramuscular injections. The Kits with IO devices may vastly expand the scope of treatment to include intravenous drugs, without having to be skilled in the technique of intravenous insertion.

Most acute care hospitals in the U.S. operate Intensive Care Units (ICUs) for seriously ill patients. Establishing and maintaining venous access in these patients is often a challenge. IO access may be a welcome procedure for administration of drugs and fluids to these critical patients.

Ten percent of the population experience a major seizure in their lifetime and more than 2,500,000 people in the United States have epilepsy. Grand mal seizures represent one of the most dramatic events in medicine. During the seizure, which usually lasts 60 to 90 seconds, patients typically fall to the ground, become rigid with trunk and extremities extended, and shake violently. The most dreaded progression of seizures is status epilepticus, a condition defined as a continuous seizure lasting more than 30 minutes or two or more seizures that occur without full conscious recovery between attacks. Convulsive status epilepticus requires urgent, immediate treatment. Patients are at risk for serious injury, hypoxemia, circulatory collapse, permanent brain damage and death. The overall mortality of convulsive status epilepticus is up to 35 percent.

Intravenous access with a large bore needle/catheter must be established to administer anticonvulsant medications. These include a benzodiazepine followed by phenytoin and/or phenobarbitol for immediate seizure control and prevention of further seizures. There are no satisfactory oral, rectal, or intramuscular medications that will control status epilepticus.

The problem facing clinicians and paramedics treating patients with status epilepticus is the difficulty establishing venous access. Without adequate venous lines none of the effective anticonvulsants can be given. During seizures the violent shaking makes accessing a satisfactory vein difficult. Often after the line is established, further shaking dislodges the IV or causes it to infiltrate.

Further, caregivers are at great risk of puncturing themselves with a needle when attempting to establish venous access in a patient during a seizure. Through no fault of their own, seizing patients, by jerking and thrashing around, turn the safest procedure into a terrifying venture. Doctors, nurses, and paramedics work in mortal fear of contracting AIDS and hepatitis through an inadvertent puncture with a contaminated needle.

In an attempt to solve the venous access problem, emergency physicians and intensivists have turned to establishing a central line (intravenous catheter placed in a large central vein such as the subclavian or femoral vein). However, with this method, even under ideal conditions, there is an increased incidence of serious side effects such as pneumothorax, hemothorax, inadvertent puncture of a major artery, infection, venous thrombosis, and embolus. In the case of a patient with status epilepticus, this method becomes increasingly difficult and dangerous for all of the above-mentioned reasons. Therefore, most doctors are reluctant to even attempt a central line until seizures have ceased.

Dialysis patients who often come to the emergency room in life threatening situations such as pulmonary edema (water on the lungs) or high potassium leading to cardiac arrest. These patients typically have troublesome or non-existent veins. The IO access may give these patients hope for a better quality of live and decrease their mortality.

Drug overdose victims, often comatose, generally require immediate IV access to give antidotes and life saving medications such as Narcan. These patients usually have difficult venous access due to long term abuse of their veins. IO access may give these patients an alternate route for delivery of medications and fluids while improving the safety of the healthcare workers.

Trauma victims and attempted suicide patients, often in shock due to blood loss, may also require swift replacement of fluids to save vital organs. Because of the shock condition (decreased blood pressure), veins collapse and are often impossible to find. IO access may save precious minutes for paramedics and trauma surgeons responsible for their care.

Although the present invention and its advantages have been described in detail, it should be understood that various changes, substitutions and alternations can be made herein without departing from the spirit and scope of the invention as defined by the following claims.

What is claimed is:

1. An apparatus for penetrating bone and accessing bone marrow, the apparatus comprising:
    a penetrator assembly operable to penetrate bone and bone marrow, the penetrator assembly comprising:
        a trocar including a stylet and a first connector forming a female connecting piece at a first end of the first connector, and
        a penetrator assembly connector at a second end of the first connector opposite to the first end of the first connector; and
        an outer penetrator including a hollow cannula and a second connector, the second connector forming a male connecting piece complementary to the female connecting piece on the first connector of the trocar, the hollow cannula configured to receive the stylet of the trocar, and the female connecting piece of the trocar configured to engage the male connecting piece of the outer penetrator; and
    a powered drill having a housing defining a handle configured to be sized and contoured to fit the hand of an operator of the apparatus, the housing enclosing a motor and a power supply and associated circuitry to power the motor, the housing further including an on/off switch connected to the power supply and operable to activate the motor to rotate the penetrator assembly when said penetrator assembly is releasably attached to the powered drill;
    the powered drill further comprising a connector receptacle, the connector receptacle configured to receive the penetrator assembly connector of the penetrator assembly, and the connector receptacle further configured to releasably lock the penetrator assembly connector into place with the powered drill;
    wherein the outer penetrator further comprises a luer lock attachment on the second connector of the outer penetrator;
    wherein the power supply comprises a battery disposed within the housing and configured to supply power to the motor; and
    the powered drill further including a battery indicator operable to indicate a level of the battery.

2. The apparatus according to claim 1, wherein the battery is a rechargeable battery, and wherein the handle further comprises a charging contact and associated charging circuitry operable to charge the rechargeable battery.

3. The apparatus according to claim 2, wherein the battery indicator further comprises a plurality of lights operable to indicate a status of the rechargeable battery.

4. The apparatus according to claim 1, wherein the battery indicator further comprises a plurality of lights operable to indicate a status of the battery.

5. The apparatus according to claim 1, wherein the hollow cannula comprises a cutting tip, and the cutting tip of the hollow cannula and a tip of the stylet are operable to penetrate bone marrow as a single drilling unit.

6. The apparatus according to claim 5, further comprising a magnetic connection to releasably lock the penetrator assembly connector into place with the powered drill.

7. The apparatus according to claim 5, wherein the outer penetrator and the stylet are ground together as one unit during a manufacturing process.

8. The apparatus according to claim 5, wherein the battery is a rechargeable battery, and the handle further comprises a charging contact and associated charging circuitry operable to charge the rechargeable battery.

9. The apparatus according to claim 8, wherein the battery indicator further comprises a plurality of lights operable to indicate a status of the rechargeable battery.

10. The apparatus according to claim 5, wherein the battery indicator further comprises a plurality of lights operable to indicate a status of the battery.

11. The apparatus according to claim 1, further comprising a magnetic connection to releasably lock the penetrator assembly connector into place with the powered drill.

12. The apparatus according to claim 11, wherein the outer penetrator further comprises a flange operable to abut skin of a patient during an insertion procedure for stabilizing the penetrator assembly.

13. The apparatus according to claim 1, wherein the outer penetrator further comprises a flange operable to abut skin of a patient during an insertion procedure for stabilizing the penetrator assembly.

14. The apparatus according to claim 1, wherein the battery is a rechargeable battery, and the handle further comprises a charging contact and associated charging circuitry operable to charge the rechargeable battery,
    wherein the battery indicator further comprises a plurality of lights operable to indicate a status of the rechargeable battery, wherein the hollow cannula comprises a cutting tip, and the cutting tip of the hollow cannula and a tip of the stylet are operable to penetrate bone marrow as a single drilling unit, and wherein the outer penetrator further comprises a flange operable to abut skin of a patient during an insertion procedure for stabilizing the penetrator assembly.

15. The apparatus according to claim 1, wherein the battery is a rechargeable battery, and the handle further comprises a charging contact and associated charging circuitry operable to charge the rechargeable battery, wherein the battery indicator further comprises a plurality of lights operable to indicate a status of the rechargeable battery, wherein the hollow cannula comprises a cutting tip and the cutting tip of the hollow cannula and a tip of the stylet are operable to penetrate bone marrow as a single drilling unit, and further comprising a magnetic connection to releasably lock the penetrator assembly connector into place with the powered drill.

16. The apparatus according to claim 1, wherein the male connecting piece comprises a connecting piece locking mechanism configured to lock into position on the female connecting piece.

17. The apparatus according to claim 1, wherein the on/off switch is disposed on an outer surface of the housing and proximate to a first end of the housing on which the connector receptacle is provided.

* * * * *